United States Patent
Beight et al.

(10) Patent No.: US 6,974,831 B2
(45) Date of Patent: Dec. 13, 2005

(54) SPLA$_2$ INHIBITORS

(75) Inventors: Douglas Wade Beight, Frankfort, IN (US); Michael Dean Kinnick, Indianapolis, IN (US); Ho-Shen Lin, Indianapolis, IN (US); John Michael Morin, Brownsburg, IN (US); Michael Enrico Richett, Indianapolis, IN (US); Daniel Jon Sall, Greenwood, IN (US); Jason Scott Sawyer, Indianapolis, IN (US); Edward C R Smith, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 331 days.

(21) Appl. No.: 10/450,741

(22) PCT Filed: Dec. 6, 2001

(86) PCT No.: PCT/US01/43187

§ 371 (c)(1),
(2), (4) Date: Jun. 16, 2003

(87) PCT Pub. No.: WO02/50030

PCT Pub. Date: Jun. 27, 2002

(65) Prior Publication Data

US 2004/0077704 A1 Apr. 22, 2004

Related U.S. Application Data

(60) Provisional application No. 60/256,397, filed on Dec. 18, 2000.

(51) Int. Cl.$^7$ .................. A61K 31/404; C07D 209/56
(52) U.S. Cl. ............................. 514/411; 548/427
(58) Field of Search ...................... 548/427; 514/411

(56) References Cited

U.S. PATENT DOCUMENTS

| | | | | |
|---|---|---|---|---|
| 5,639,778 A | * | 6/1997 | Andersson et al. | ......... 514/411 |
| 5,684,034 A | | 11/1997 | Bach et al. | |
| 6,831,095 B1 | * | 12/2004 | Harper et al. | ............... 514/419 |

FOREIGN PATENT DOCUMENTS

| | | |
|---|---|---|
| EP | 0 620 214 | 10/1994 |
| WO | WO 94/21608 | 9/1994 |
| WO | WO 00/10568 | 3/2000 |
| WO | WO 00/69818 | 11/2000 |

* cited by examiner

*Primary Examiner*—Golam M. M. Shameem
(74) *Attorney, Agent, or Firm*—Francis O. Ginah

(57) ABSTRACT

A novel class of cycloalkyl fused indole compounds is disclosed together with the use of such compounds for inhibiting sPLA2 mediated release of fatty acids for treatment of Inflammatory Diseases such as septic shock.

17 Claims, No Drawings

SPLA$_2$ INHIBITORS

This application claims the benefit of provisional application Ser. No. 60/256,397 filed Dec. 18, 2000.

FIELD OF THE INVENTION

This invention relates to novel cycloalkylfused indole compounds useful for Inflammatory Diseases.

BACKGROUND OF THE INVENTION

The structure and physical properties of human non-pancreatic secretory phospholipase A$_2$ (hereinafter called, "sPLA$_2$") has been thoroughly described in two articles, namely, "Cloning and Recombinant Expression of Phospholipase A$_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase A$_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

It is believed that sPLA$_2$ is a rate limiting enzyme in the arachidonic acid cascade which hydrolyzes membrane phospholipids. Thus, it is important to develop compounds, which inhibit sPLA$_2$ mediated release of fatty acids (e.g., arachidonic acid). Such compounds would be of value in the general treatment of conditions induced and/or maintained by overproduction of sPLA$_2$; such as sepsis or rheumatoid arthritis.

It is desirable to develop new compounds and treatments for sPLA$_2$ induced diseases.

SUMMARY OF THE INVENTION

The present invention relates to a cyclofused indole compound of formula (I), or pharmaceutically acceptable salt, solvate or prodrug thereof:

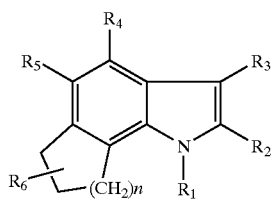

(I)

Wherein;

n is 1, 2 or 3;

R$_1$ is selected from group (a), (b), or (c) wherein;
(a) is C$_2$–C$_{20}$ alkyl, C$_2$–C$_{20}$ haloalkyl, C$_2$–C$_{20}$ alkenyl, C$_2$–C$_{20}$ alkynyl, carbocyclic radical, or heterocyclic radical, or
(b) is a member of (a) substituted with one or more independently selected non-interfering substituents;
(c) is the group -(L)-R$_{80}$; where, -(L)- is a divalent linking group of 1 to 12 atoms selected from carbon, hydrogen, oxygen, nitrogen, and sulfur; wherein the combination of atoms in -(L)- are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where R$_{80}$ is a group selected from (a) or (b);

R$_2$ is hydrogen, or a group containing 1 to 10 non-hydrogen atoms plus any required hydrogen atoms;

R$_3$ is -(L$_3$)-Z, where -(L$_3$)- is a divalent linker group selected from a bond or a divalent group selected from:

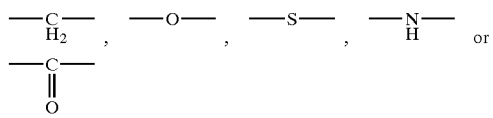

and Z is selected from an oxime amide or oxime thioamide group represented by the formulae,

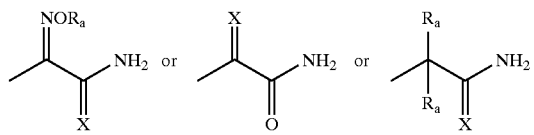

wherein X is oxygen or sulfur, R$_a$ is independently selected from hydrogen, C$_1$–C$_8$ alkyl, aryl, C$_1$–C$_8$ alkaryl, C$_1$–C$_8$ alkoxy, aralkyl and —CN;

R$_4$ is the group, hydrogen, CONH$_2$, CONHR$^{4b}$ or -(La)-(acidic group) wherein -(L$_a$)-, is an acid linker having an acid linker length of 1 to 8;

or the group -(L$_h$)-(N-hydroxyfunctional amide group); wherein -(L$_h$)-, is an N-hydroxyfunctional amide linker having a N-hydroxyfunctional amide linker length of 1 to 8; and wherein a N-hydroxyfunctional amide group is represented by the formula:

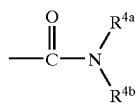

wherein R$^{4a}$ is selected from the group consisting of OH, (C$_1$–C$_6$)alkoxy, and aryloxy; and
wherein R$^{4b}$ is hydrogen or an organic substituent selected from the group consisting of (C$_1$–C$_8$)alkyl, aryl, (C$_7$–C$_{14}$) aralkyl, (C$_7$–C$_{14}$)alkaryl, (C$_3$–C$_8$)cycloalkyl, (C$_1$–C$_8$) alkoxyalkyl and these groups substituted with halogen, —CF$_3$, —OH, (C$_1$–C$_8$)alkyl, amino, carbonyl, and —CN;

or R$_4$ is the group -(Lc)-(acylamino acid group)- wherein the "acylamino acid group" is represented by the formula:

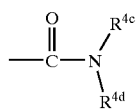

wherein R$^{4c}$ is selected from the group consisting of H, (C$_1$–C$_6$)alkyl, (C$_1$–C$_6$)alkoxy, heteroaryl and aryl, —CF$_3$; and wherein NR$^{4d}$ is an amino acid residue of either a natural or unnatural amino acid with the nitrogen atom being part of the amino group of the amino acid.

R$_5$ is selected from hydrogen, and a non-interfering substituent;

R$_6$ is a multiple or single independently selected non-interfering substituent.

The present invention provides novel cycloalkylfused indole compounds of formula I having potent and selective effectiveness as inhibitors of mammalian sPLA$_2$.

The present invention also relates to the use of novel cycloalkylfused indole compounds of formula I useful in the treatment and/or prevention of Inflammatory Diseases.

This invention also relates to the use of a novel cycloalkylfused indole compound of formula I to inhibit mammalian sPLA$_2$ mediated release of fatty acids.

The present invention provides a pharmaceutical composition containing any of the cycloalkylfused indole compounds of the invention.

The present invention also relates to the use of a formulation comprising a compound of formula 1, and a carrier or diluent for the treatment or prevention of sepsis The present invention relates to the use of a pharmaceutical composition comprising a therapeutically effective amount of sPLA$_2$ inhibitor compounds of formula I and mixtures thereof for the manufacture of a medicament for the treatment of Inflammatory Diseases.

I. Definitions:

The terms, "mammal" and "mammalian" include human and domesticated quadrupeds.

The term, "Inflammatory Diseases" refers to diseases such as inflammatory bowel disease, sepsis, septic shock, adult respiratory distress syndrome, pancreatitis, trauma-induced shock, asthma, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enteropathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit sPLA$_2$ mediated release of fatty acid and to thereby inhibit or prevent the arachidonic acid cascade and its deleterious products.

The term, "cycloalkylfused indole", or "cycloalkylfused indole nucleus" as used herein refers to a nucleus (having numbered positions) with the structural formula (X):

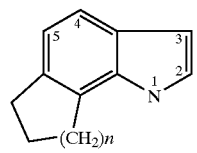

wherein, n is 1, 2 or 3.

The cycloalkylfused indole compounds of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, sec-butyl, n-pentyl, and n-hexyl.

The term, "alkenyl" employed alone or in combination with other terms means a straight chain or branched monovalent hydrocarbon group having the stated number ranges of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo. The term, heterocyclic radical, refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, benzo(b)thiophenyl, carbazolyl, norharmanyl, azabenzo(b)thiophenyl, benzofuranyl, dibenzofuranyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiophenyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are benzyl, cycloalkyl, cycloalkenyl, phenyl, spiro[5.5]undecanyl, naphthyl, norbornanyl, bicycloheptadienyl; toluyl, xylenyl, indenyl, stilbenyl, terphenylyl, diphenylethylenyl, phenyl-cyclohexenyl, acenaphthylenyl, and anthracenyl, biphenyl, dibenzylyl and related dibenzylyl homologues represented by the formula (a):

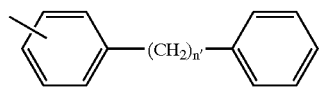

where n' is a number from 1 to 8.

The terms, "non-interfering substituent", or "non-interfering groups" refer to radicals suitable for substitution at positions 1, 2, 3, 4, 5, and/or 6 of the cycloalkylfused indole nucleus and on other nucleus substituents (as hereinafter described for Formula I), and radicals suitable for substitution on the heterocyclic radical and carbocyclic radical as defined above. Illustrative non-interfering radicals are (C$_1$–C$_8$)alkyl, (C$_2$–C$_8$)alkenyl, (C$_2$–C$_8$)alkynyl, (C$_7$–C$_{12}$)aralkyl, (C$_7$–C$_{12}$)alkaryl, (C$_3$–C$_8$)cycloalkyl, (C$_3$–C$_8$)cycloalkenyl, phenyl, toluyl, xylenyl, biphenyl, ($C_1$–$C_8$)alkoxy, $C_2$–$C_8$)alkenyloxy, $C_2$–$C_8$ alkynyloxy, ($C_2$–$C_{12}$) alkoxyalkyl, ($C_2$–$C_{12}$)alkoxyalkyloxy, $C_2$–$C_{12}$ alkylcarbonyl, ($C_2$–$C_{12}$)alkylcarbonylamino, ($C_2$–$C_{12}$) alkoxyamino, ($C_2$–$C_{12}$)alkoxyaminocarbonyl, ($C_1$–$C_{12}$) alkylamino, ($C_1$–$C_6$)alkylthio, ($C_2$–$C_{12}$)alkylthiocarbonyl, ($C_1$–$C_8$)alkylsulfinyl, ($C_1$–$C_8$)alkylsulfonyl, ($C_2$–$C_8$) haloalkoxy, ($C_2$–$C_8$)haloalkylsulfonyl, ($C_2$–$C_8$)haloalkyl, ($C_2$–$C_8$)hydroxyalkyl, —C(O)O(($C_2$–$C_8$)alkyl), —(CH$_2$)$_n$—O—($C_1$–$C_8$ alkyl), benzyloxy, phenoxy, phenylthio,
—(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and carbonyl; where n is from 1 to 8 and R is ($C_1$–$C_8$)alkyl.

The term, "organic substituent" refers to a monovalent radical consisting of carbon and hydrogen with or without oxygen, nitrogen, sulfur, halogen, or other elements. Illustrative organic substituents are ($C_1$–$C_8$)alkyl, aryl, ($C_7$–$C_{14}$) aralkyl, ($C_7$–$C_{14}$)alkaryl, ($C_3$–$C_8$)cycloalkyl, ($C_1$–$C_8$) alkoxyalkyl and these groups substituted with halogen, —CF$_3$, —OH, ($C_2$–$C_8$)alkyl, amino, carbonyl, and —CN.

The term "substituted group" is an organic group substituted with one or more non-interfering substituents.

As used herein the terms "group", "radical" or "fragment" are synonymous and are intended to indicate functional groups or fragments of molecules attachable to a bond or other fragments of molecules. For example acetamide group represent the acetamide fragment or radical. Structures of groups, radicals or fragments unattached to the cycloalkylfused indole nucleus have been drawn to show the first line as a connecting bond only. Thus, the group

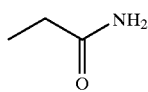

indicates the acetamide radical or group not the propanamide radical unless otherwise indicated.

The term, "N-hydroxyfunctional amide group" is represented by the formula:

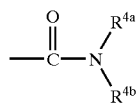

wherein $R^{4a}$ is selected from the group consisting of OH, ($C_1$–$C_6$)alkoxy, and aryloxy; and
wherein $R^{4b}$ is hydrogen or an organic substituent selected from the group consisting of ($C_1$–$C_8$)alkyl, aryl, ($C_7$–$C_{14}$) aralkyl, ($C_7$–$C_{14}$)alkaryl, ($C_3$–$C_8$)cycloalkyl, ($C_3$–$C_8$) alkoxyalkyl and these groups substituted with halogen, —CF$_3$, —OH, ($C_1$–$C_8$)alkyl, amino, carbonyl, and —CN.

The phrase, "N-hydroxyfunctional amide linker" refers to a divalent linking group symbolized as, -(L$_h$)-, which has the function of joining the 4-position of the cycloalkylfused indole nucleus to an N-hydroxyfunctional amide group in the general relationship:

| cycloalkylfused indole nucleus | (L$_h$) | N-hydroxyfunctional amide group |

The phrase, "hydroxyfunctional amide linker length", refers to the number of atoms (excluding hydrogen) in the shortest chain of the linking group -(L$_h$)- that connects the 4-position of the cycloalkylfused indole nucleus with the N-hydroxyfunctional amide group. The presence of a carbocyclic ring in -(L$_h$)- counts as the number of atoms approximately equivalent to the calculated diameter of the carbocyclic ring. Thus, a benzene or cyclohexane ring in the acid linker counts as 2 atoms in calculating the length of -(L$_h$)-. Illustrative "N-hydroxyfunctional amide linker" groups are;

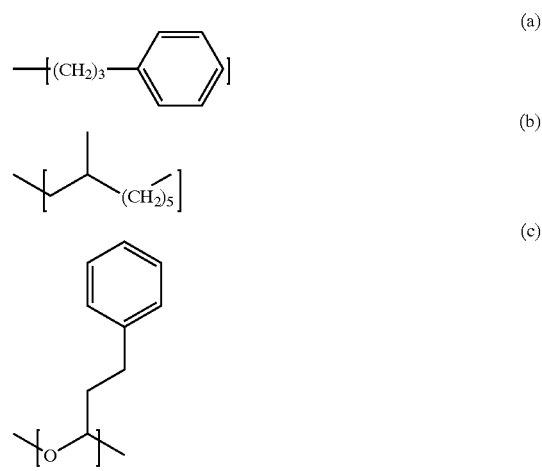

wherein, groups (a), (b) and (c) have acid linker lengths of 5, 7, and 2, respectively.

The term, "(acidic group)" means an organic group which when attached to a cycloalkylfused indole nucleus at the 4-position, through suitable linking atoms (hereinafter defined as the "acid linker"), acts as a proton donor capable of hydrogen bonding. Illustrative of an (acidic group) are the following:

-5-tetrazolyl,
—SO$_3$H,

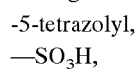

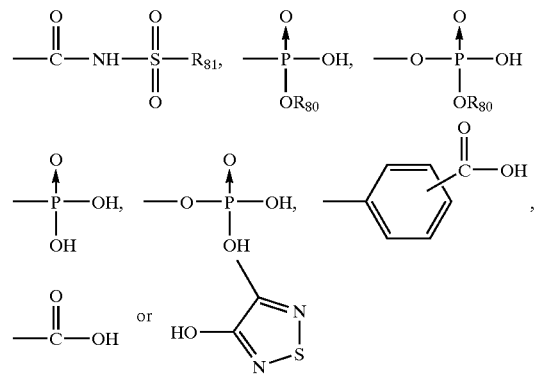

where n is 1 to 8, $R_{80}$ is a metal or ($C_1$–$C_8$) and $R_{81}$ is an organic substituent or —CF$_3$.

The words, "acid linker" refer to a divalent linking group symbolized as, -(L$_a$)-, which has the function of joining the 4-position of the cycloalkylfused indole nucleus to an acidic group in the general relationship:

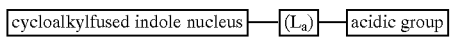

The words, "acid linker length", refer to the number of atoms (excluding hydrogen) in the shortest chain of the linking group -($L_a$)- that connects the 4-position of the cycloalkylfused indole nucleus with the acidic group. The presence of a carbocyclic ring in -($L_a$)- counts as the number of atoms approximately equivalent to the calculated diameter of the carbocyclic ring. Thus, a benzene or cyclohexane ring in the acid linker counts as 2 atoms in calculating the length of -($L_a$)-.

Illustrative acid linker groups include;

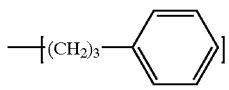

(a)

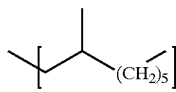

(b)

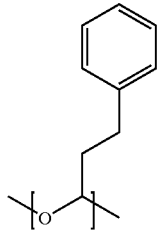

(c)

wherein, groups (a), (b), and (c) have acid linker lengths of 5, 7, and 2, respectively.

The term, "acylamino acid group" is represented by the formula:

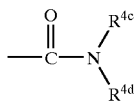

wherein $R^{4c}$ is selected from the group consisting of H, ($C_1$–$C_6$)alkyl, ($C_1$–$C_6$)alkoxy, heteroaryl and aryl, —$CF_3$; and wherein $NR^{4d}$ is an amino acid residue of either a natural or unnatural amino acid with the nitrogen atom being part of the amino group of the amino acid. A typical amino acid is selected from the group comprising isoleucine, valine, phenylalanine, aspartic acid, leucine, glycine, asparagine, cystein, glutamine, glutamic acid, histidine, lysine, methionine, serine, threonine, tryptophan, tyrosine and derivatives thereof. Contemplated within the definition of amino acid are l-proline, d-proline and derivatives thereof. Also contemplated within the definition of amino acids are peptides, polypeptides and derivatives thereof.

The term, "amino acid residue" refers to the portion of the amino acid group coupled at the nitrogen atom of the amino terminus. It is the amino acid less a hydrogen atom from the amino terminus. It is further illustrated as used herein for the amino acid alanine attached at the nitrogen atom as shown below:

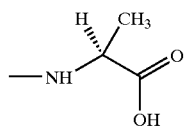

The words, "acylamino acid linker" refer to a divalent linking group symbolized as, -($L_c$)-, which has the function of joining the 4-position of the cycloalkylfused indole nucleus to an acylamino acid group in the general relationship:

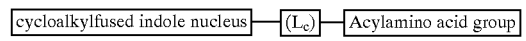

The phrase, "acylamino acid linker length", refers to the number of atoms (excluding hydrogen) in the shortest chain of the linking group -($L_c$)- that connects the 4-position of the cycloalkylfused indole nucleus with the acylamino acid group. The presence of a carbocyclic ring in -($L_c$)- counts as the number of atoms approximately equivalent to the calculated diameter of the carbocyclic ring. Thus, a benzene or cyclohexane ring in the acid linker counts as 2 atoms in calculating the length of -($L_c$)-. Illustrative "acylamino acid linker groups" include:

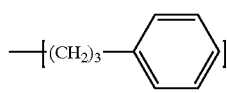

(a)

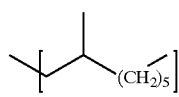

(b)

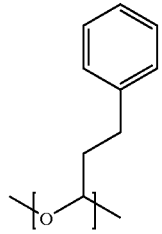

(c)

wherein, groups (a), (b) and (c) have acid linker lengths of 5, 7, and 2, respectively.

The term, "amine", includes primary, secondary and tertiary amines.

The term, "alkylene chain of 1 or 2 carbon atoms" refers to the divalent radicals, —$CH_2$—$CH_2$— and —$CH_2$—.

The term, "group containing 1 to 10 non-hydrogen atoms" refers to relatively small groups which form substituents at the 2-position of the cycloalkylfused indole nucleus, said groups may contain non-hydrogen atoms alone, or non-hydrogen atoms plus hydrogen atoms as required to satisfy the unsubstituted valence of the non-hydrogen atoms, for example; (i) groups absent hydrogen which contain no more than 4 non-hydrogen atoms such as —$CF_3$, —Cl, —Br, —$NO_2$, —CN, —$SO_3$; and (ii) groups having hydrogen atoms which contain less than 4 non-hydrogen atoms such as —$CH_3$, —$C_2H_5$, and —CH=$CH_2$.

The term "oxime amide" means the radical, —C(=NOR)—C(O)$NH_2$

The term "thio-oxime amide" means the radical —C(=NOR)—C(S)—$NH_2$.

The term "spiro[5.5]undecanyl" refers to the group represented by the formula;

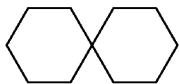

II. The Cycloalkylfused Indole Compounds of the Invention:

The present invention provides a novel class of cycloalkylfused indole compounds useful as sPLA$_2$ inhibitors for the treatment and/or prophylaxis of inflammation attendant to inflammatory diseases. Subclasses of cycloalkylfused indole compounds of this invention include cycloalkylfused indole oxyacid derivatives, cycloalkylfused indole-3-oxime amide oxyacid derivatives, cycloalkylfused indole-3-acetamide oxyacid derivatives, cycloalkylfused indole-3-glyoxylamide-N-hydroxyfunctional amide derivatives, cycloalkylfused indole-3-oxime amide-N-hydroxyfunctional amide derivatives, cycloalkylfused indole-3-acetamide hydroxy functional amide derivatives, cycloalkylfused indole-3-glyoxylamide acylamino acid derivatives, cycloalkylfused indole-3-oxime amide acylamino acid derivatives, cycloalkylfused indole-3-acetamide acylamino acid derivatives.

The compounds of the invention are represented by the general formula (I) and include a pharmaceutically acceptable salt, solvate or prodrug thereof;

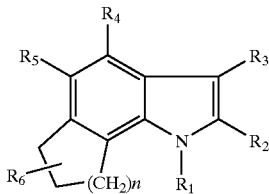

(I)

wherein;

n is 1, 2 or 3;

$R_1$ is selected from group (a), (b), or (c) wherein;
  (a) is $C_2$–$C_{20}$ alkyl, $C_2$–$C_{20}$ haloalkyl, $C_2$–$C_{20}$ alkenyl, $C_2$–$C_{20}$ alkynyl, carbocyclic radical, or heterocyclic radical, or
  (b) is a member of (a) substituted with one or more independently selected non-interfering substituents;
  (c) is the group -(L)-$R_{80}$; where, -(L)- is a divalent linking group of 1 to 12 atoms selected from carbon, hydrogen, oxygen, nitrogen, and sulfur; wherein the combination of atoms in -(L)- are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where $R_{80}$ is a group selected from (a) or (b);

$R_2$ is hydrogen, or a group containing 1 to 10 non-hydrogen atoms plus any required hydrogen atoms;

$R_3$ is -(L$_3$)- Z, where -(L$_3$)- is a divalent linker group selected from a bond or a divalent group selected from:

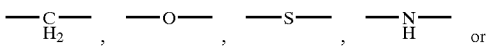

and Z is selected from an oxime amide or oxime thioamide group represented by the formulae,

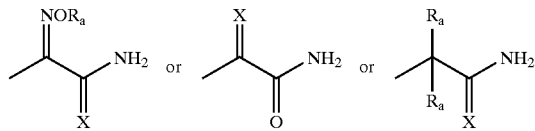

wherein X is oxygen or sulfur, $R_a$ is independently selected from hydrogen, $C_1$–$C_8$ alkyl, aryl, $C_1$–$C_8$ alkaryl, $C_1$–$C_8$ alkoxy, aralkyl and —CN;

$R_4$ is the group, hydrogen, CONH$_2$, CONHR$^{4b}$ or -(La)-(acidic group) wherein -(L$_a$), is an acid linker having an acid linker length of 1 to 8;

or the group -(L$_h$)-(N-hydroxyfunctional amide group); wherein -(L$_h$)-, is an N-hydroxyfunctional amide linker having a N-hydroxyfunctional amide linker length of 1 to 8; and wherein a N-hydroxyfunctional amide group is represented by the formula:

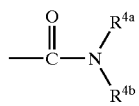

wherein $R^{4a}$ is selected from the group consisting of OH, (C$_1$–C$_6$)alkoxy, and aryloxy; and wherein $R^{4b}$ is hydrogen or an organic substituent selected from the group consisting of (C$_1$–C$_8$)alkyl, aryl, (C$_7$–C$_{14}$) aralkyl, (C$_7$–C$_{14}$)alkaryl, (C$_3$–C$_8$)cycloalkyl, (C$_1$–C$_8$) alkoxyalkyl and these groups substituted with halogen, —CF$_3$, —OH, (C$_1$–C$_8$)alkyl, amino, carbonyl, and —CN;

or $R_4$ is the group -(Lc)- (acylamino acid group)- wherein the "acylamino acid group" is represented by the formula:

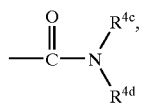

wherein $R^{4c}$ is selected from the group consisting of H, (C$_1$–C$_6$)alkyl, (C$_1$–C$_6$)alkoxy, heteroaryl and aryl, —CF$_3$; and wherein NR$^{4d}$ is an amino acid residue of either a natural or unnatural amino acid with the nitrogen atom being part of the amino group of the amino acid.

$R_5$ is selected from hydrogen, a non-interfering substituent; and $R_6$ is a multiple or single independently selected non-interfering substituent.

Preferred Subgroups of Compounds of Formula (I):

Preferred $R_1$ Substituents:

A preferred subclass of compounds of formula (I) are those where for $R_1$ the divalent linking group -(L$_1$)- is a group represented by any one of the following formulae (Ia), (Ib), (Ic), (Id), (Ie), or (If):

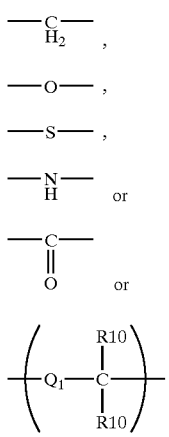

(Ia)

(Ib)

(Ic)

(Id)

(Ie)

(If)

where $Q_1$ is a bond or any of the divalent groups (Ia), (Ib), (Ic), (Id), (Ie), and (If) and each $R_{10}$ is independently hydrogen, $(C_1-C_8)$alkyl, $(C_1-C_8)$haloalkyl or $(C_1-C_8)$alkoxy.

Particularly preferred as the linking group -$(L_1)$- of $R_1$ is an alkylene chain of 1 or 2 carbon atoms, namely, —$(CH_2)$— or —$(CH_2-CH_2)$—.

The preferred group for $R_{11a}$ is a substituted or unsubstituted group selected from the group consisting of $(C_5-C_{14})$cycloalkyl, $(C_5-C_{14})$cycloalkenyl, phenyl, naphthyl, norbornanyl, bicycloheptadienyl, toluyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula (a);

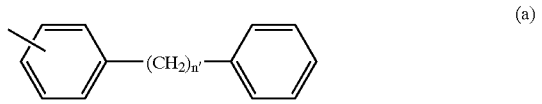

where n' is a number from 1 to 8.

Particularly preferred are compounds wherein for $R_1$ the combined group -$L_1$)-$R_{11a}$ is selected from the group consisting of

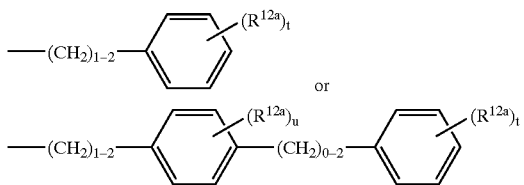

where $R^{12a}$ is a radical independently selected from halo, $(C_1-C_8)$alkyl, $(C_1-C_8)$alkoxy, —S—$((C_1-C_8)$alkyl), —O—$((C_1-C_8)$alkyl) and $(C_1-C_8)$haloalkyl where t is a number from 0 to 5 and u is a number from 0 to 4.

is the group -$(L_1)$-$R_{11a}$; where, -$(L_1)$- is a divalent linking group of 1 to 8 atoms and where $R_{11a}$ is a group selected from (a) or (b).

Preferred for $R_{11a}$ is —$(CH_2)$m-$R^{12a}$ wherein m is an integer from 1 to 6, and $R^{12a}$ is (d) a group represented by the formula:

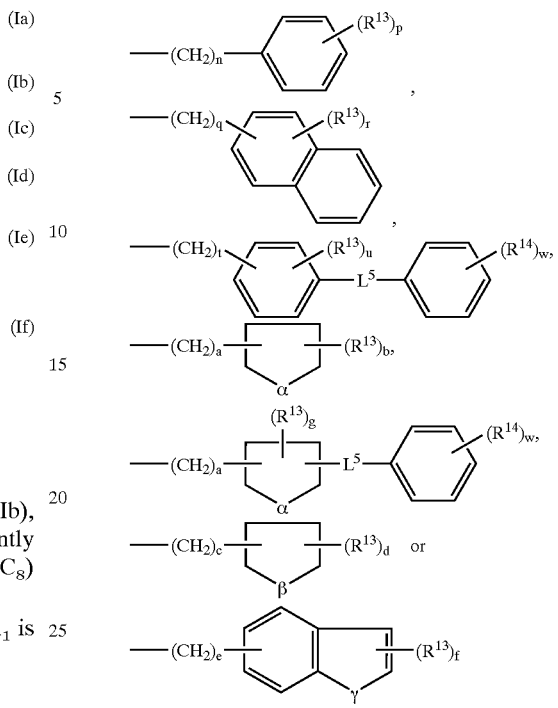

wherein a, c, e, n, q, and t are independently an integer from 0 to 2, $R^{13}$ and $R^{14}$ are independently selected from a halogen, $C_1$ to $C_8$ alkyl, $C_1$ to $C_8$ alkyloxy, $C_1$ to $C_8$ alkylthio, aryl, heteroaryl, and $C_1$ to $C_8$ haloalkyl, α is an oxygen atom or a sulfur atom, $L^5$ is a bond, —$(CH_2)$v-, —C=C—, —CC—, —O—, or —S—, v is an integer from 0 to 2, β is —$CH_2$— or —$(CH_2)_2$—, γ is an oxygen atom or a sulfur atom, b is an integer from 0 to 3, d is an integer from 0 to 4, f, p, and w are independently an integer from 0 to 5, r is an integer from 0 to 7, and u is an integer from 0 to 4, or is (e) a member of (d) substituted with at least one substituent selected from the group consisting of $C_1$ to $C_6$ alkyl, $C_1$ to $C_8$ alkyloxy, $C_1$ to $C_8$ haloalkyloxy, $C_1$ to $C_8$ haloalkyl, aryl, and a halogen.

Preferred $R_2$ Substituents:

$R_2$ is preferably selected from the group consisting of hydrogen, $(C_1-C_4)$alkyl, $(C_2-C_4)$alkenyl, —O—$((C_1-C_4)$alkyl), —S—$((C_1-C_3)$alkyl), —$(C_3-C_4)$cycloalkyl, —$CF_3$, halo, —$NO_2$, —CN, —$SO_3$. Particularly preferred $R_2$ groups are selected from hydrogen, methyl, ethyl, propyl, isopropyl, cyclopropyl, —F, —$CF_3$, —Cl, —Br, or —O—$CH_3$.

Preferred $R_3$:

A preferred subgroups of $R_3$ is -$(L_3)$- Z, where -$(L_3)$- is a divalent linker group selected from a bond or a divalent group selected from:

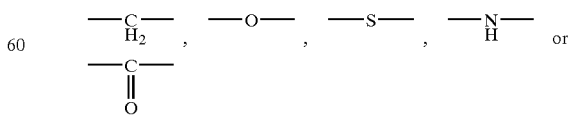

and Z is selected from a glyoxylamide, acetamide, an oxime amide or oxime thioamide group represented by the formulae,

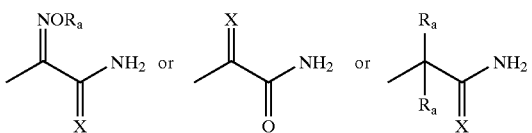

wherein X is oxygen or sulfur, $R_a$ is independently selected from hydrogen, $C_1$–$C_8$ alkyl, aryl, $C_1$–$C_8$ alkaryl, $C_1$–$C_8$ alkoxy, aralkyl and —CN;

A more preferred subclass of compounds of formula (I) are those wherein X is oxygen.

Also more preferred is a subclass of compounds of formula I wherein Z is a glyoxylamide (glyoxamide) group represented by

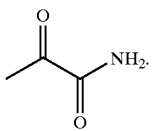

Another preferred subclass of compounds of formula (I) are those wherein Z is an amide group

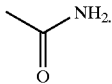

Also preferred are compounds of formula (I) wherein Z is an acetamide group represented by the formulae:

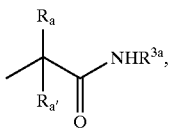

wherein $R_a$ and $R_{a'}$ are independently selected from hydrogen, $(C_1$–$C_8)$alkyl, aryl, $(C_1$–$C_8)$alkaryl, $(C_1$–$C_8)$ alkoxy, aralkyl and —CN, and $R^{3a}$ is hydrogen, $NH_2$, methyl, or ethyl.

For the group $R_3$ it is most preferred that the linking group -$(L_3)$- be a bond.

Preferred R4 Substituents:

A preferred subgroup of $R_4$ is the group, hydrogen, $CONH_2$, $CONHR^{4b}$ or -(La)-(acidic group) wherein -$(L_a)$-, is an acid linker having an acid linker length of 1 to 8;

or the group -$(L_h)$-(N-hydroxyfunctional amide group); wherein -$(L_h)$-, is an N-hydroxyfunctional amide linker having a N-hydroxyfunctional amide linker length of 1 to 8; and wherein a N-hydroxyfunctional amide group is represented by the formula:

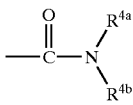

wherein $R^{4a}$ is selected from the group consisting of OH, $(C_1$–$C_6)$alkoxy, and aryloxy; and wherein $R^{4b}$ is hydrogen or an organic substituent selected from the group consisting of $(C_1$–$C_8)$alkyl, aryl, $(C_7$–$C_{14})$ aralkyl, $(C_7$–$C_{14})$alkaryl, $(C_3$–$C_8)$cycloalkyl, $(C_1$–$C_8)$ alkoxyalkyl and these groups substituted with halogen, —$CF_3$, —OH, $(C_1$–$C_8)$alkyl, amino, carbonyl, and —CN;

or $R_4$ is the group -(Lc)- (acylamino acid group)- wherein the "acylamino acid group" is represented by the formula:

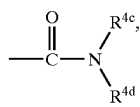

wherein $R^{4c}$ is selected from the group consisting of H, $(C_1$–$C_6)$alkyl, $(C_1$–$C_6)$alkoxy, heteroaryl and aryl, —$CF_3$; and wherein $NR^{4d}$ is an amino acid residue of either a natural or unnatural amino acid with the nitrogen atom being part of the amino group of the amino acid. A most preferred subgroup of $R_4$ is the group, hydrogen, $CONH_2$, $CONHR^{4b}$ or -(La)-(acidic group) wherein -$(L_a)$-, is an acid linker having an acid linker length of 1 to 8;

Also preferred is a subclass of compounds of formula I wherein -$(L_a)$- is an acid linker selected from the group consisting of;

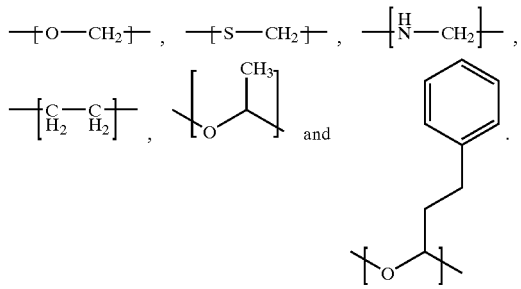

Another preferred subclass of compounds of formula I are those wherein $R_4$ is the group -$(L_c)$- (acylamino acid group)-, wherein -(Lc)- is an acylamino acid linker with an acylamino acid linker length of 2 or 3, and the "acylamino acid group" is represented by the formula:

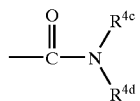

wherein $R^{4c}$ is selected from the group consisting of H, $(C_1$–$C_6)$alkyl, $(C_1$–$C_6)$alkoxy, heteroaryl and aryl, —$CF_3$; and wherein $NR^{4d}$ is an amino acid residue of either a natural or unnatural amino acid with the nitrogen atom being part of the amino group of the amino acid; and wherein the amino acid residue is derived from an amino acid selected from the group comprising isoleucine, valine, phenylalanine, aspartic acid, leucine, glycine, asparagine, cystein, glutamine, glutamic acid, histidine, lysine, methionine, serine, threonine, tryptophan, tyrosine and derivatives thereof.

Another preferred subclass of compounds of formula (I) are those wherein $R_4$ is a substituent having an N-hydroxyfunctional amide linker with an N-hydroxyfunctional amide linker length of 2 or 3 and the N-hydroxyfunctional amide linker group, -$(L_h)$-, for $R_4$ is selected from a group represented by the formula;

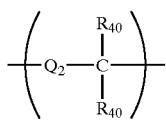

where $Q_2$ is selected from the group —$(CH_2)$—, —O—, —NH—, —C(O)—, and —S—, and each $R_{40}$ is independently selected from hydrogen, $C_1$–$C_8$ alkyl, aryl, $C_1$–$C_8$ alkaryl, $C_1$–$C_8$ alkoxy, aralkyl, and halo.

Most preferred subclasses of compound of formula (I) are compounds where the acid linker -(La)-, or the N-hydroxyfunctional amide linker, -($L_h$)-, or the acylamino acid linker -($L_c$)-, for $R_4$ is independently selected from the specific groups;

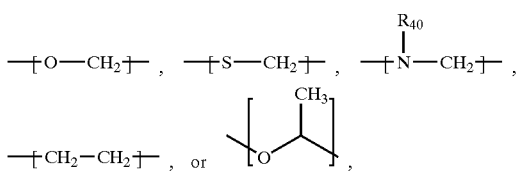

wherein $R_{40}$ is hydrogen or $(C_1$–$C_8)$alkyl.

Most preferred compounds of the invention are those having the general formula (II) or (III) or (IV) or a pharmaceutically acceptable salt, solvate or prodrug derivative thereof;

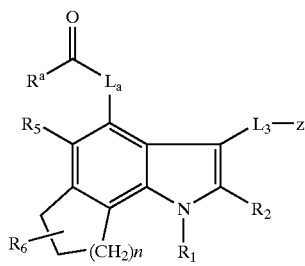

II

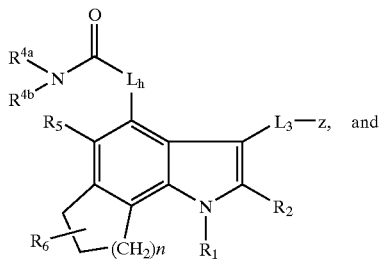

III

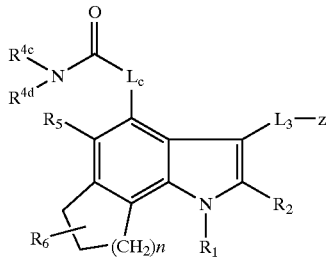

IV wherein;
n is 1, or 2;
$R_1$ is as described previously;
$R_2$ is as described previously;
$R_3$, $R_4$, $R_5$, and $R_6$ are as described previously;
$R^{4a}$, $R^{4b}$, $R^{4c}$, and $R^{4d}$ are previously defined;
$L_3$ is preferably a bond;
$L_a$, $L_h$, and $L_h$ are each preferably the group —OCH$_2$—;
and Z is selected from an amide, thioamide or glyoxylamide, acetamide or thioacetamide, oxime, hydrazide radical (group) represented by the formulae,

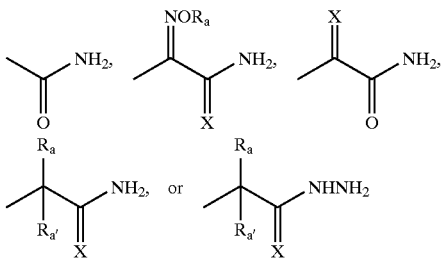

wherein X is oxygen or sulfur, $R_a$ and $R_{a'}$ are independently selected from hydrogen, $(C_1$–$C_8)$alkyl, aryl, $(C_1$–$C_8)$alkaryl;

Particularly preferred are compounds of formula II wherein $R_3$ is ($L_3$)-Z; L is a bond and Z is represented by the group:

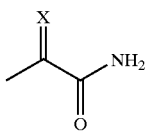

wherein X is oxygen.

Most preferred compounds (and all pharmaceutically acceptable salts, solvates and prodrug derivatives thereof) which are illustrative of the compounds of the invention for treatment of a human afflicted with Inflammatory Disease, a pharmaceutically acceptable salt, solvate, or a prodrug derivative of a compound selected from the group consisting of:

2-[[3-(2-Amino-1,2-dioxoethyl)-2-ethyl-1-benzyl-1,6,7,8-tetrahydrocyclopent[g]indol-4-yl]oxy]acetic acid methyl ester;

2-[[3-(2-Amino-1,2-dioxoethyl)-2-ethyl-1-benzyl-1,6,7,8-tetrahydrocyclopent[g]indol-4-yl]oxy]acetic acid;

2-[[3-(2-Amino-1,2-dioxoethyl)-2-methyl-1-benzyl-1,6,7,8-tetrahydrocyclopent[g]indol-4-yl]oxy]acetic acid methyl ester;

2-[[3-(2-Amino-1,2-dioxoethyl)-2-methyl-1-benzyl-1,6,7,8-tetrahydrocyclo-pent[g]indol-4-yl]oxy]acetic acid;

2-[4-(2-Benzenesulfonylamino-2-oxoethoxy)-1-benzyl-2-methyl-1,6,7,8-tetrahydro-1-aza-as-indacen-3-yl]-2-oxoacetamide;

2-[[3-(2-Amino-1,2-dioxoethyl)-2-methyl-1-(3-fluorobenzyl)-1,6,7,8-tetrahydrocyclopent[g]indol-4-yl]oxy]acetic acid methyl ester;

2-[[3-(2-Amino-1,2-dioxoethyl)-2-methyl-1-(3-fluorobenzyl)-1,6,7,8-tetrahydrocyclopent[g]indol-4-yl]oxy]acetic acid hydrate;

2-[[3-(2-Amino-1,2-dioxoethyl)-2-methyl-1-(2-fluorobenzyl)-1,6,7,8-tetrahydrocyclopent[g]indol-4-yl]oxy]acetic acid;

2-[[3-(2-Amino-1,2-dioxoethyl)-2-methyl-1-(4-fluorobenzyl)-1,6,7,8-tetrahydrocyclopent[g]indol-4-yl]oxy]acetic acid methyl ester;

2-[[3-(2-Amino-1,2-dioxoethyl)-1-benzyl-2-ethyl-6,7,8,9-tetrahydro-1H-benz[g]indol-4-yl]oxy]acetic acid methyl ester;

2-[[3-(2-Amino-1,2-dioxoethyl)-1-benzyl-2-ethyl-6,7,8,9-tetrahydro-1H-benz[g]indol-4-yl]oxy]acetic acid;
2-[[3-(2-Amino-1,2-dioxoethyl)-1-benzyl-2-methyl-6,7,8,9-tetrahydro-1H-benz[g]indol-4-yl]oxy]acetic acid methyl ester;
2-[[3-(2-Amino-1,2-dioxoethyl)-1-benzyl-2-methyl-6,7,8,9-tetrahydro-1H-benz[g]indol-4-yl]oxy]acetic acid;
2-[[3-(2-Amino-1,2-dioxoethyl)-2-methyl-1-(2-bromobenzyl)-1,6,7,8-tetrahydrocyclopent[g]indol-4-yl]oxy]acetic acid methyl ester;
2-[[3-(2-Amino-1,2-dioxoethyl)-2-methyl-1-(2-bromobenzyl)-1,6,7,8-tetrahydrocyclopent[g]indol-4-yl]oxy]acetic acid;
2-[[3-(2-Amino-1,2-dioxoethyl)-2-methyl-1-(2-phenylbenzyl)-1,6,7,8-tetrahydrocyclopent[g]indol-4-yl]oxy]acetic acid methyl ester; and
2-[[3-(2-Amino-1,2-dioxoethyl)-2-methyl-1-(2-phenylbenzyl)-1,6,7,8-tetrahydrocyclopent[g]indol-4-yl]oxy]acetic acid.

Most preferred compounds of the invention are represented by the formulae (C1), (C2), (C3), (C4), (C5), (C6), (C7), (C8), (C9), (c10), (C11), or (C12);

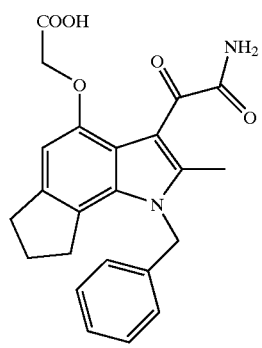

(C1)

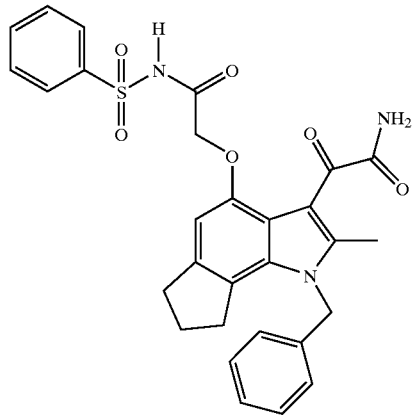

(C2)

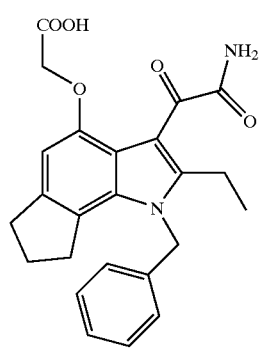

(C3)

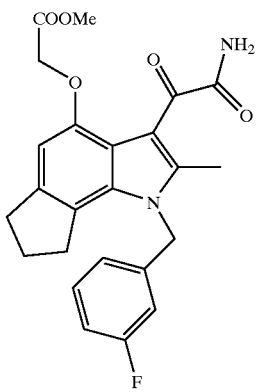

(C4)

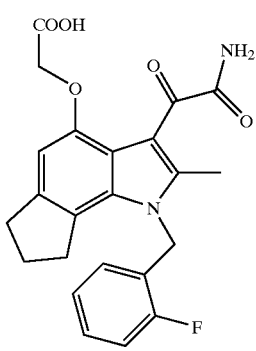

(C5)

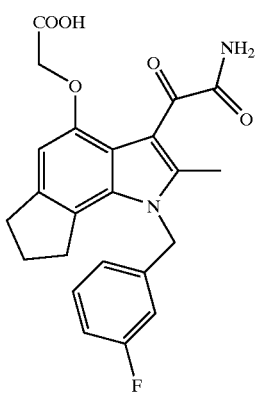

(C6)

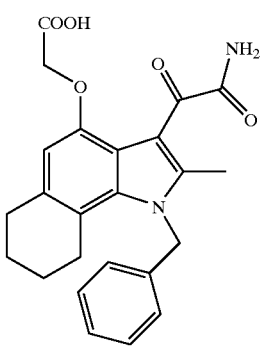

(C7)

-continued (C8) 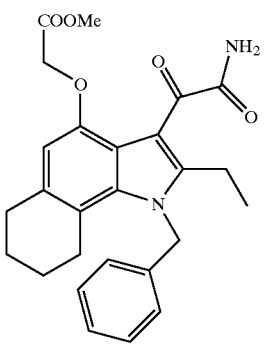

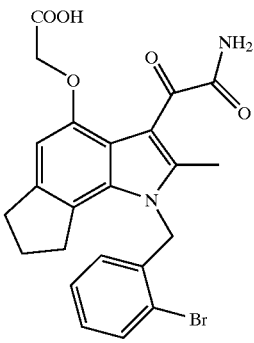

(C9) 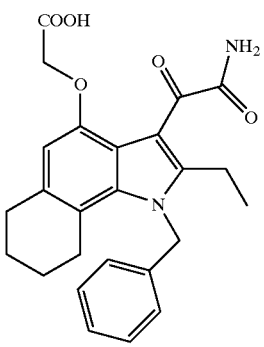

(C10) 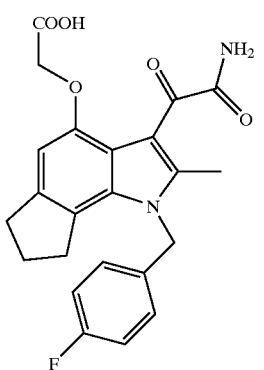

(C11) 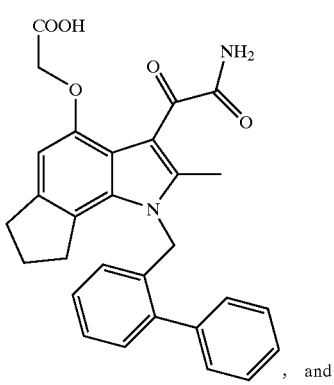, and

-continued (C12)

The salts of the cycloalkylfused indole compounds represented by formulae (I), (II), (III), and (IV), are an additional aspect of the invention.

In those instances when the compound of the invention possesses acidic or basic functional groups, various salts may be formed which are more water soluble and more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, hydrochloride, clavulanate, citrate, chloride, edetate, edisylate, estolate, esylate, fluoride, fumarate, gluceptate, gluconate, glutamate, glycolylarsanilate, hexylresorcinate, hydroiodide hydroxynaphthoate, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of stereoisomers and diastereomers, because they have different melting points, different boiling points, and different solubilities and can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099-6). Morpholinylethyl ester prodrugs may be prepared by reaction of the sodium salt of a compound of formula (I) (in a medium such as dimethylformamide) with 4-(2-chloroethyl) morpholine hydrochloride (available from Aldrich Chemical Co., Milwaukee, Wis. USA, Item No. C4, 220-3).

(III) Method of Preparing the Cycloalkylfused indole-3-glyoxylamide Compound:

The cycloalkylfused indole-3-glyoxylamide compounds are compounds of this invention and are also useful as intermediates or starting materials for preparing other compounds of the invention. The cycloalkylfused indole-3-amide compounds are prepared by following a protocol such as Scheme 1 below:

Scheme 1

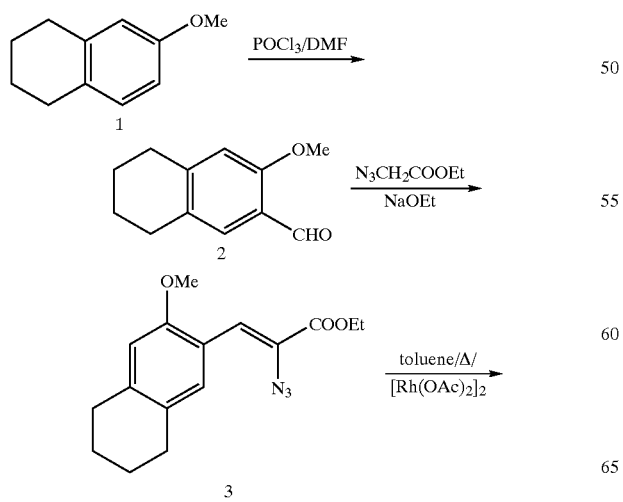

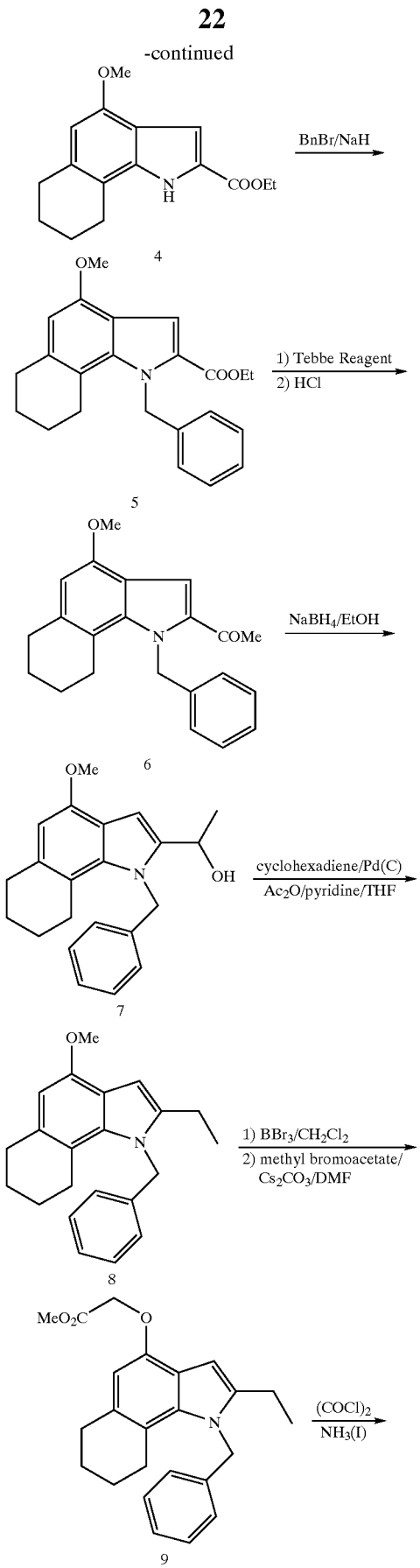

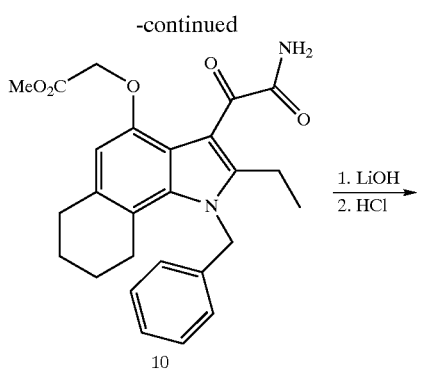

10

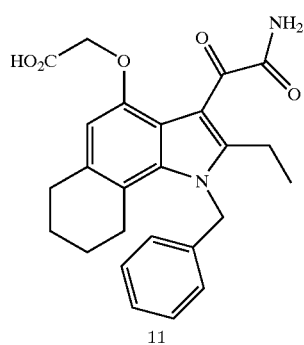

11

Scheme 1 depicts a protocol for preparing tetrahydrobenz[g]indole-3-glyoxylamide compounds of the invention by using 3-methoxy-5,6,7,8-tetrahydronaphthalene (1) (available from Aldrich Chemical Co., Milwaukee, USA) as the starting material. As shown, the starting material (1) is reacted with a complex (Vilsmeier reagent) formed from adding phosphorus oxychloride to a cold (about −20 to +5° C.) solution of N,N-dimethylformamide (see Vilsmeier-Hack reaction in Jerry March, *Advanced organic Chemistry*, 3$^{rd}$ edition, Wiley-Interscience Publishers, New York). The resulting mixture was heated to about 80° C. for about 1 to 6 hours, preferably about 3 to 5 hours to afford the compound (2). The compound (2) may be isolated by extractive work up with an organic solvent preferably diethyl ether, followed by concentration and crystallization from a suitable solvent or solvent system. A preferred crystallization solvent is hexane with a trace of ethanol.

The compound of formula (2) is subjected to an aldol or aldol type condensation reaction with ethyl azidoacetate by adding a suitable solution of (2), preferably in ethanol or ethanol/ether to a solution of sodium ethoxide in ethanol. The sodium ethoxide solution is preferably generated as needed by adding sodium metal to a cold solution of absolute ethanol. The addition of a solution of (2) to sodium ethoxide is performed preferably at about −20° C. to −10° C. The resulting mixture is stirred for about 1 to 4 hours, preferably for about 2 hours. The product (3) is precipitated from water, washed, isolated and dried.

The product (3) is reductively cyclized to form the indole compound (4). Reductive cyclization is preferably performed by heating compound (3) in toluene at reflux, and more preferably with rhodium(II)acetate dimer (Aldrich Chemical Co.) at reflux over a period of about 1 to 20 hours, preferably about 4 to 10 hours. The indole (4) is substituted at the indole nitrogen with alkyl, cycloalkyl, aryl, alkylaryl groups or the like, to introduce the $R_1$ group, by a base catalyzed de-protonation followed by a nucleophilic attack on an electrophile. Electrophiles suitable for this reaction are those necessary to incorporate the $R_1$ group described previously and include for example, alkyl, aryl, and arylalkyl groups as the halides, sulfonates or other leaving groups. For example, the reaction of compound (4) with sodium hydride or a suitable base (i.e., n-BuLi, lithium diisopropyl amide) in a suitable solvent e.g., dimethylformamide, followed by addition of benzyl bromide for example, affords upon work-up the compound of formula (5).

The compound of formula (5) is converted to the ketone, for example, the methylketone (6). Preparation of compound (6) is accomplished for example, by reaction of compound (5) with μ-chloro-μ-methylene[bis(cyclopentadienyl)-titanium]dimethylaluminum (Tebbe reagent). The formation of the methylketone derivative (6) using Tebbe reagent involves addition of about 1.2 molar equivalent of Tebbe reagent to a cold solution (about 0° C.) of compound (5) in tetrahydrofuran or similar solvent. The reaction mixture is allowed to warm to about room temperature (about 14–25° C.). Upon satisfactory completion of the reaction as determined by common laboratory methods, i.e., HPLC, GC, TLC, GCMS, etc, the reaction mixture is quenched by addition of saturated aqueous potassium carbonate. This likely results in vigorous evolution of gas. The product (6) is isolated upon aqueous extractive work-up procedures and application of standard purification methods, i.e. chromatography and/or crystallization.

The compound of formula (7) may be obtained by the use of mild and/or selective reducing agents and/or reaction conditions that do not affect the methoxy substituent at the 4-position. This is accomplished, for example, by reduction with sodium borohydride in ethanol at about room temperature (about 21° C.) over a period of 1 to 3 hours followed by aqueous work-up and isolation to afford compound (7). The compound of formula (8) may be obtained by reduction of compound (7) with, for example, 10% Pd/C with cyclohexadiene in the presence of acetic anhydride and pyridine. The reaction is performed at about 70° C. for about 4 to 36 hours or until complete. Additional quantities of cyclohexadiene and 10% Pd/C are added as necessary until the reaction is satisfactorily complete. The product is isolated by dilution with hexane/ether, followed by addition of citric acid and finally filtration through silica gel. The resulting filtrate is concentrated to afford compound (8).

The compound (8) is de-methylated by reaction with boron tribromide or sodium thioethoxide in a suitable solvent such as dichloromethane. About 1.0 to 2.0 equivalents of boron tribromide is typically sufficient to effect complete de-methylation. The de-methylation reaction temperature is from about −12° C. to about 10° C. Work-up is accomplished by stirring with methyl alcohol or other suitable protic solvent. The stirring in methyl alcohol is followed by neutralization with a base such as sodium bicarbonate. This is followed by extraction and purification of the organic phase by methods known to one of skill in the art. The incipient product is then dissolved in N,N-dimethylformamide followed by addition of a slight excess (about 1.05 mole equiv. based on (8)) of cesium carbonate or other mild base, and methylbromoacetate to afford compound (9) after about 1 to 6 hours of reaction. Compound (9) is isolated by aqueous extraction followed by chromatography. Other 2-substituted haloacetates i.e. benzylbromoacetate may be used to prepare an analog of (9).

The compound of formula (9) may be reacted with oxalyl chloride in a suitable solvent, e.g., methylene chloride at about 0 to 10° C. for about 1 hour or as necessary. This is followed by reaction with ammonia (THF solution saturated with ammonia) to afford the compound of formula (10).

The free acid (11) is optionally obtained by acidifying the saponifacation product of (10) or other basification reaction product, e.g. with potassium or lithium hydroxide. Most strong inorganic acids are suitable for acidification as described previously. However, the use of dilute HCl is preferred. The free acid (11) may be extracted into an organic phase if soluble, and dried by common laboratory methods or dried by removing water from the aqueous phase. Alternatively the saponification reaction product (sodium hydroxide reaction with (10)), itself a compound of the invention, may be isolated without acidification.

Alternatively, the compound of formula (6) may be converted to the compound of formula (8a), by use of borane-tetrahydrofuran complex (CAS# 14044-65-6, Aldrich Chemical Co. Wisconsin, USA.), for example. The reactions to convert the methoxy group of a compound of formula (6) or analog thereof to compounds of formula (8) or (8a) are typically performed in THF or other suitable solvent. Scheme (1b) shows a protocol to compounds of the invention via (8a).

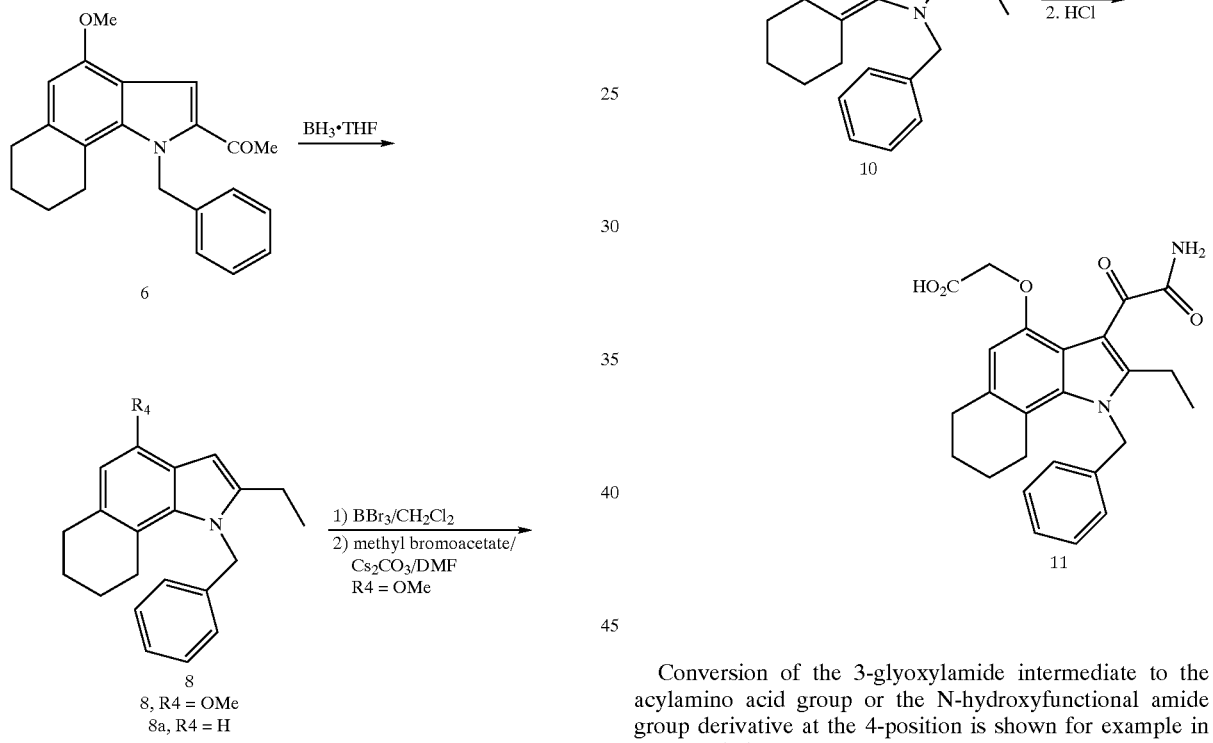

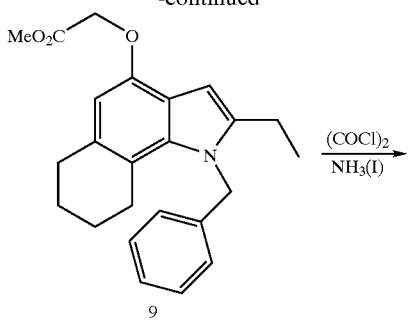

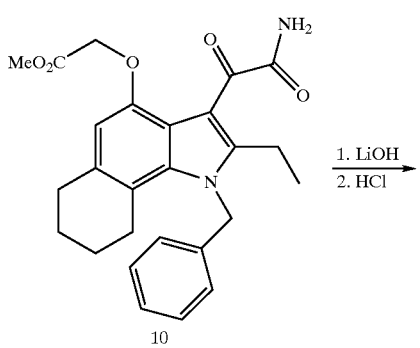

Conversion of the 3-glyoxylamide intermediate to the acylamino acid group or the N-hydroxyfunctional amide group derivative at the 4-position is shown for example in Scheme (1c) below:

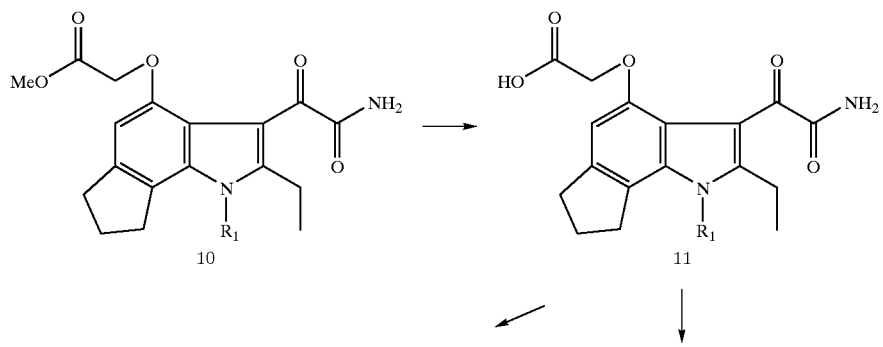

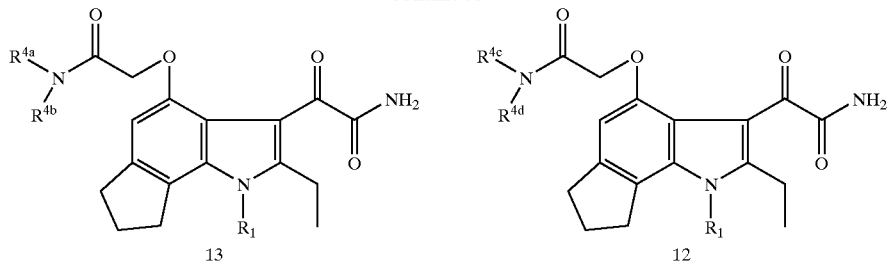

13    12

According to Scheme 1c, the oxyacetic acid ester (10) may be converted to the free acid (11) or to derivatives such as the ester or amide by procedures known to one of skill in the art. See for example, J. March *Advanced Organic Chemistry*, Wiley Interscience publishers, New York, N.Y., 1985, and R. C. Larock *Comprehensive Organic Transformations*, VCH Publishers, New York, N.Y., 1989.

The acid (11) is functionalized at the 4-position to the acylamino acid derivative (12) by base catalyzed condensation with an amino acid protected at the acid terminus (using a protecting group known in the literature but preferably the methyl ester). The reaction is accomplished using coupling agents such as HOBT/EDCI, BOP/collidine or other amide-bond forming coupling agents. Protocols for preparing amide type bonds utilizing coupling agents such as above are known to one fo skill in the art and may be found in general reference texts such as those provided herein.

The N-hydroxyfunctional amide group may be introduced via the acid (11) or acid salt thereof, by reaction with for example hydroxylamine hydrochloride or substituted hydroxylamine hydrochloride to afford the N-hydroxyfunctional amide compound of formula (13) upon deprotection and/or aqueous work-up. For example, the acid compound (11) is reacted with o-(tert-butyldimethylsilyl) hydroxylamine at ambient temperature, in the presence of excess 2,4,6-collidine (collidine) and benzotriazol-1-yl-oxytris(dimethylamino)phosphonium hexafluorophosphonate (coupling catalyst, see *Tetrahedron Lett.*, 1219 (1975)) to afford, after about 1–10 hours, the o-(tert-butyldimethylsilyl) substituted N-hydroxyfunctional amide derivative (not shown). The silyl or other protecting group is removed by well known methods such as for example, the use of trifluoroacetic acid for removal of silyl protecting groups) to afford, for example, the N-hydroxyfunctional amide compound (13) wherein $R^{4a}$ is hydroxy and $R^{4b}$ is hydrogen.

Typically, the condensation or coupling is performed in a solvent such a dimethylformamide, tetrahydrofuran or aqueous mixtures of the like. In general protic solvents are preferred for the purpose of this invention. A base including for example, weak organic or inorganic bases catalyzes the reaction. Organic bases such as collidine are preferred. The reaction is also preferably run in the presence of agents that retard or reduce racemization of the hydroxyfunctional amide, the substituted hydroxylamine or its derivative. A particularly preferred agent is benzotriazolyl-N-oxy-tris(dimethylamino)phosphonium hexafluorophosphate. Upon completion of the reaction, the mixture is concentrated in vacuo. The resulting product mixture is chromatographed or crystallized, e.g., by sonication to obtain the target compound.

Tetrahydrobenz[g]indol-3-acetamide sPLA$_2$ inhibitor derivatives of compounds (8) or (8a) (from Scheme 1b) may be obtained by lithiation of compound (8) or (8a) at the 3-position with an organolithium reagent e.g. n-butyllithium followed by quenching the lithiated intermediate with ethylene oxide to afford upon hydrolysis, the terminal alcohol derivative (14) at the 3-position as shown below in Scheme 2.

Scheme 2

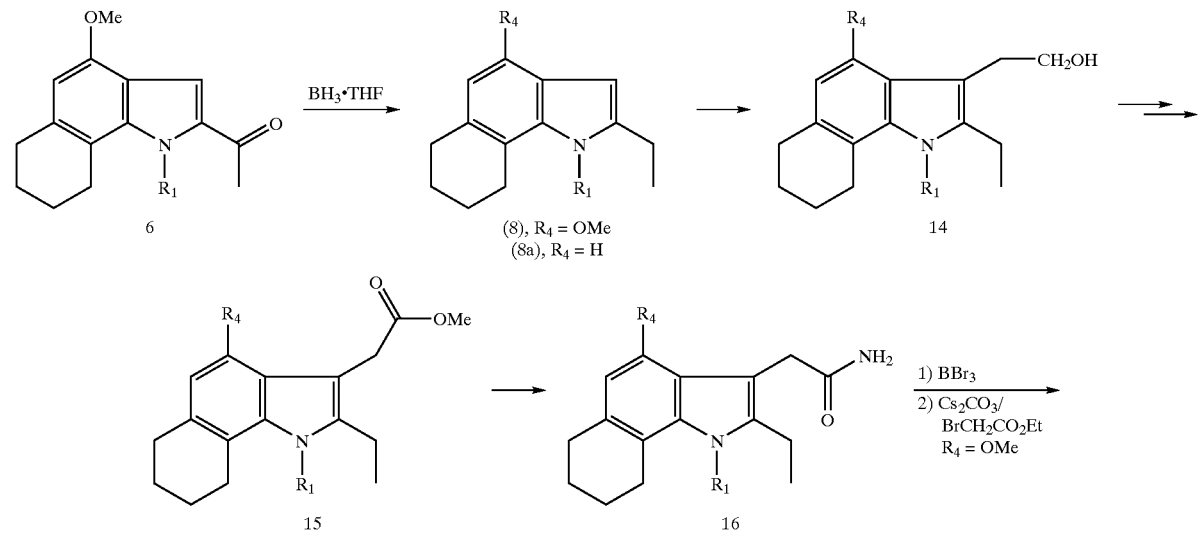

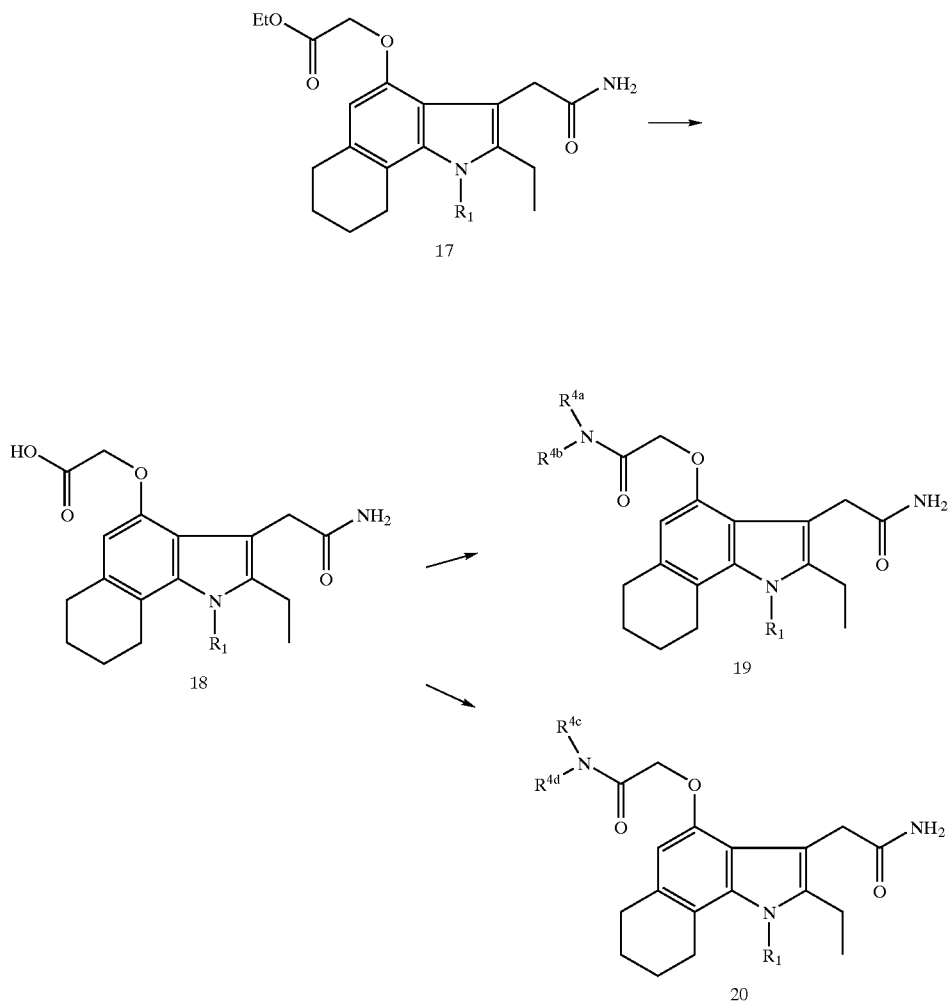

The resulting alcohol intermediate (14), itself a compound of the invention, may be converted by oxidation to the acid and further converted to the ester (15). Conversion of the alcohol intermediate (14) to an ester via an intermediate acid may be accomplished, for example, by oxidation of the alcohol with sodium hypochlorite in buffered t-butanol followed by esterification of the incipient acid to the ester (15). Methods for these conversions are known to one of skill in the art and may be found in general reference texts discussed previously. The ester (15) may be converted to the acetamide derivative (16) or other substituted acetamide compound. For example the reaction of the methyl acetate (15) with methylchloroaluminum amide in benzene or other suitable solvent or solvent mixtures affords the acetamide (compound 16). (See Levin, J. I.; Turos, E.; Weinreb, S. M. *An alternative procedure for the aluminum-mediated conversion of esters to amides. Syn. Comm.,* 1982, 12, 989–993).

Similarly, use of N-substituted methylchloroaluminum amides result in the corresponding substituted acetamides (see Weinreb supra). Alternatively the terminal alcohol (15) could be converted to the acid halide (i.e. chloride) via the acid (alcohol oxidation product). The acid halide is then ammoniated to form the acetamide or substituted acetamide depending on amine used.

The 3-substituted tetrahydrobenz[g]indole acetamide compounds described above may be converted to the corresponding 4-substituted N-hydroxyfunctional amide compounds (19) or the 4-substituted acylamino acid compounds (20) as described previously for the glyoxylamide compounds (Scheme 1c). For example, the methoxy group at the 4-position of compound (16) may be demethylated as described above, reacted with bromomethylacetate and cesium carbonate in DMF to form the oxyacetic acid ester group at the 4-position (compound 17). The oxyacetic acid ester group of (17) is further elaborated to the acid (18). The acid (18) is converted to the N-hydroxyfuntional amide group or the N-acylaminoacid group as discussed above.

The substituted tetrahydrobenz[g]indol-3-oxime amide compounds of the invention can be prepared following protocol of Scheme (3) below:

Scheme 3

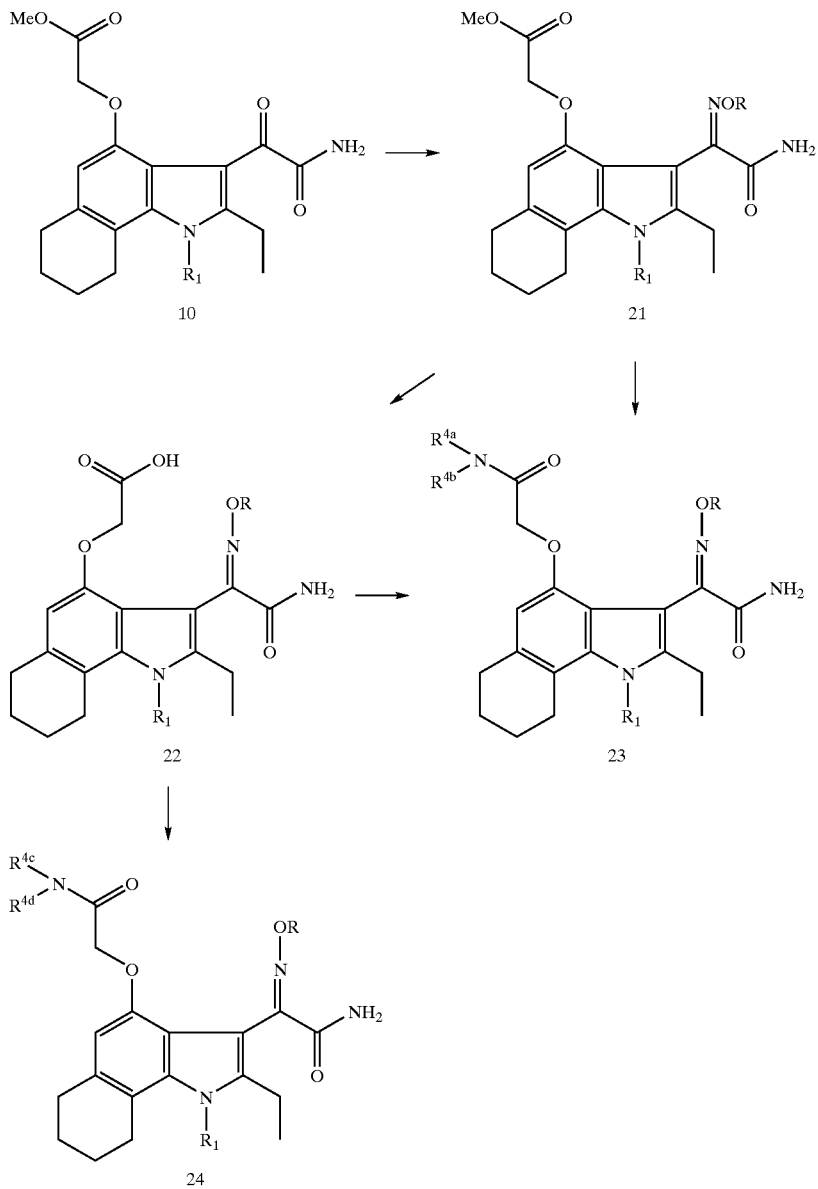

To introduce the oxime functionality, the compound of formula (10), for example, is heated with hydroxylamine hydrochloride (when R is H) in a THF/methanol mixture for about 1 to 8 hours or until the reaction is deemed satisfactorily complete. The reaction product compound (21), a compound of the invention, is isolated by chromatography or other known laboratory procedure. Substituted oximes such as when R is methyl, ethyl, phenyl or other non-interfering substituent may be prepared by reaction of the corresponding substituted hydroxylamine hydrochloride or free base with the glyoxylamide (e.g. compound 10) as described supra.

Similarly, the ester i.e. methylester of the acid compound (11), or the acid salts thereof, may be converted to the corresponding oxime or substituted oxime functionality at position 3- by the method described above. The ester functionality at the 4-position on the substituted tetrahydrobenz [g]indole nucleus, as in for example, compound (21), may be converted to the acid by hydrolysis using lithium hydroxide or other known ester hydrolysis methods to afford a compound of formula (22). See, for example, J. March *Advanced Organic Chemistry*, Wiley Interscience publishers, New York, N.Y., 1985, and R. C. Larock *Comprehensive Organic Transformations*, VCH Publishers, New York, N.Y., 1989.

Furthermore, the oxime compounds prepared as described above may be converted to the N-hydroxyfunctional amide at the 4-position, via the ester (21), the free acid (22), or the acid salt functionalities at the 4-position. For example, Scheme (3) shows the conversion of the free acid compound (22) to the N-hydroxyfunctional amide compound (23).

Likewise, the compound (22) and analogs thereof may be converted to the acylamino acid compound (24) and corresponding homologs thereof, by procedures described supra.

Tetrahydrocyclopent[g]indole compounds of formula I may be prepared by a Scheme similar to Scheme 1, except that 2,3-dihydro-6-methoxy-1H-indene (25) is substituted for 3-methoxy-5,6,7,8-dihydronaphthalene (compound 1 of Scheme 1). The protocol for preparing tetrahydrocyclopent[g]indole compounds of formula I is shown in Scheme 4 below;

Scheme 4

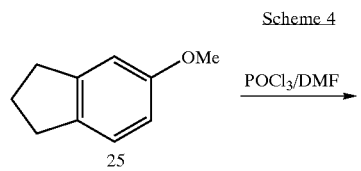
25
→ POCl₃/DMF

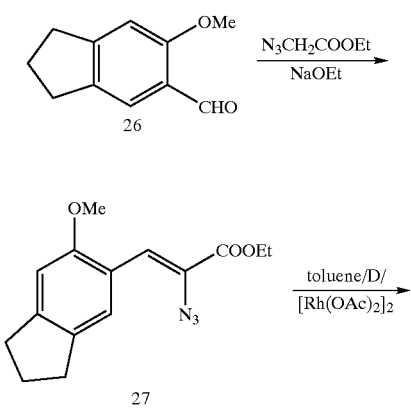
26
→ N₃CH₂COOEt / NaOEt

27
→ toluene/Δ / [Rh(OAc)₂]₂

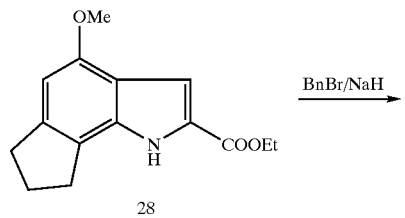
28
→ BnBr/NaH

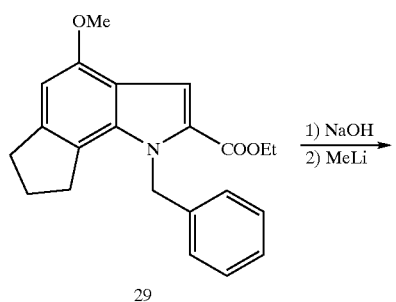
29
→ 1) NaOH  2) MeLi

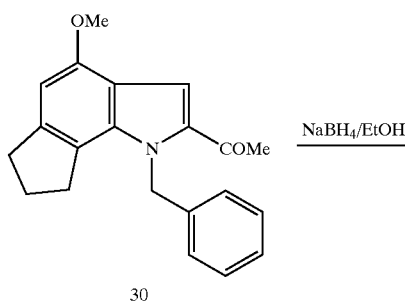
30
→ NaBH₄/EtOH

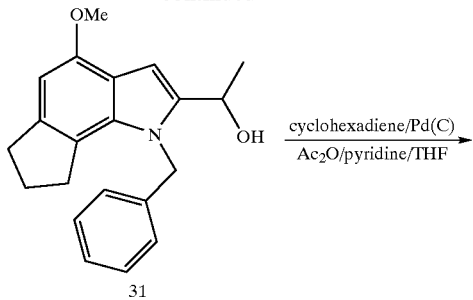
31
→ cyclohexadiene/Pd(C) / Ac₂O/pyridine/THF

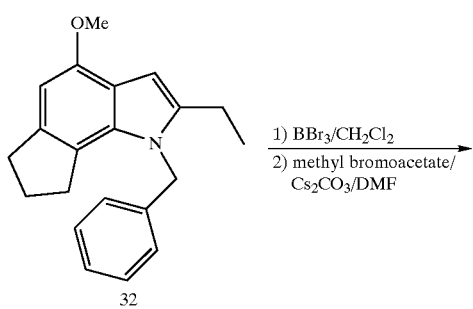
32
→ 1) BBr₃/CH₂Cl₂  2) methyl bromoacetate/ Cs₂CO₃/DMF

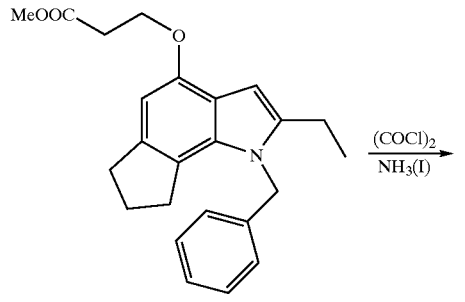
33
→ (COCl)₂ / NH₃(l)

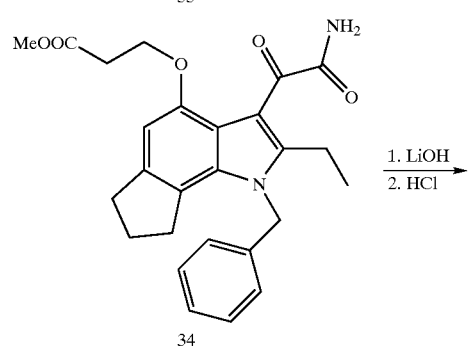
34
→ 1. LiOH  2. HCl

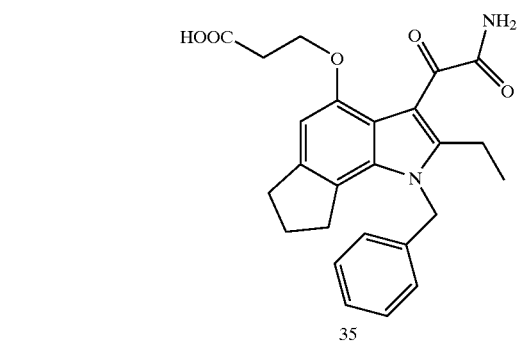
35

A possible and preferred variation from Scheme 1 includes the cyclization of the azidoacetate by heating in for example, toluene over 4 to 10 hours at reflux without the use of rhodium acetate dimer as in Scheme 1. Following substitution on the indole nitrogen, the product (29) for example, may be hydrolyzed by use of sodium hydroxide for example, to convert the ethyl ester to the terminal carboxylic acid in contrast to the use of Tebbe reagent to form the methylketone. In that case, terminal acid (not shown) may then be converted to the ketone by reaction with an alkyl lithium reagent followed by quenching. Preferably the methyllithium reagent is used to afford the methyl ketone (30) which on further reduction affords the ethyl substituent at the 2-position.

In general, other substituents at the 2-position may be prepared by elaborating the ketone (compound 6, Scheme 4, or compound 30, Scheme 4) by Peterson type olefination reactions, for example, followed by optional reductions to obtain saturated or unsaturated, substituted and or elongated carbon chain length at the 2-position. Procedures and reagents for Peterson type or other olefination reactions are found in (general organic chemistry reference texts such as J. March, Advanced Organic Chemistry $3^{rd}$ ed., Wiley-Interscience Publishers, New York).

When a methyl group is desired at the 2-position, this is accomplished by reducing the ethyl ester product from reductive cyclization of the azidoethylecetate intermediate (compound (5) Scheme 1, compound (29) Scheme 4) to the terminal carbinol. The terminal carbinol is then reduced by a two step process involving conversion to the methyl ether (using NaH, carbon disulfide, methyl iodide as described in the examples) followed by tri-n-butyltin hydride reduction aided by azobisisobutryronitrile. The reduction step can also be effected by making the tosylhydrazone from the corresponding aldehyde and tosylhydrazide, followed by reduction with lithium tetrahydridoaluminate ($LiAlH_4$). These methodologies and their application are known to one of skill in the art and may be found in J. March, Advanced Organic chemistry supra and other reference texts.

IV. Methods of Using the Compounds of the Invention:

The cycloalkylfused indole compounds described herein are believed to achieve their beneficial therapeutic action principally by direct inhibition of mammalian (including human) $sPLA_2$, and not by acting as antagonists for arachidonic acid, nor other active agents below arachidonic acid in the arachidonic acid cascade, such as 5-lipoxygenases, cyclooxygenases, and etc.

The method of the invention for inhibiting $sPLA_2$ mediated release of fatty acids comprises contacting mammalian $sPLA_2$ with a therapeutically effective amount of cycloalkylfused indole compounds corresponding to Formulae (I) or (II) or (III) or (IV) as described herein including a combination thereof, a salt or a prodrug derivative thereof.

Another aspect of this invention relates to a method for treating Inflammatory Diseases such as inflammatory bowel disease, septic shock, adult respiratory distress syndrome, pancreatitis, trauma, asthma, bronchial asthma, allergic rhinitis, rheumatoid arthritis, osteoarthritis, and related diseases which comprises administering to a mammal (including a human) a therapeutically effective dose of a cycloalkylfused indole compound of the invention.

As previously noted the compounds of this invention are useful for inhibiting $sPLA_2$ mediated release of fatty acids such as arachidonic acid. By the term, "inhibiting" is meant the prevention or therapeutically significant reduction in release of $sPLA_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effect will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably compounds of the invention per Formula (I) or (II) or (III) or (IV) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the cycloalkylfused indole compound of the invention together with a pharmaceutically acceptable carrier or diluent therefor. The present pharmaceutical formulations are prepared by known procedures using well-known and readily available ingredients.

In making the compositions of the present invention, the Active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of 2 mg/ml in a 4% dextrose/0.5% Na citrate aqueous solution. Solid form formulations include powders, tablets and capsules. A solid carrier can be one or more substance, which may also act as flavoring agents, lubricants, solubilizers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. A preferred tablet formulation for oral administration is one that affords rapid dissolution in the mouth of a patient in need thereof.

In powders the carrier is a finely divided solid which is in admixture with the finely divided Active ingredient. In tablets the Active ingredient is mixed with a carrier having the necessary binding properties in suitable proportions and compacted in the shape and size desired. The powders and tablets preferably contain from about 1 to about 99 weight percent of the Active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active ingredient can be dissolved or suspended in a pharmaceutically acceptable carrier, such as sterile water, sterile organic solvent or a mixture of both. The Active ingredient can often be dissolved in a suitable organic solvent, for instance aqueous propylene glycol. Other compositions can be made by dispersing the finely divided Active ingredient in aqueous starch or sodium carboxymethyl cellulose solution or in a suitable oil.

The following pharmaceutical formulations 1 through 8 are illustrative only and are not intended to limit the scope of the invention in any way. "Active ingredient", refers to a compound-according to Formula (I) or (II) or (III) or (IV) or a pharmaceutically acceptable salt, solvate, or prodrug thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The Active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active ingredient, are made as follows:

| | |
|---|---|
| Active ingredient | 225 mg |
| Saturated fatty acid glycerides | 2,000 mg |
| Total | 2,225 mg |

The Active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 ml |

The solution of the above ingredients generally is administered intravenously to a subject at a rate of 1 ml per minute.

Assay

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents:

REACTION BUFFER—
  $CaCl_2.2H_2O$ (1.47 g/L)
  KCl (7.455 g/L)
  Bovine Serum Albumin (fatty acid free) (1 g/L)
    (Sigma A-7030, product of Sigma Chemical Co., St. Louis Mo., USA)
  TRIS HCl (3.94 g/L)
  pH 7.5 (adjust with NaOH)

ENZYME BUFFER—
  0.05 $NaOAc.3H_2O$, pH 4.5
  0.2 NaCl
  Adjust pH to 4.5 with acetic acid DTNB—5,5'-dithiobis-2-nitrobenzoic acid RACEMIC DIHEPTANOYL THIO—PC
  racemic 1,2-bis(heptanoylthio)-1,2-dideoxy-sn-glycero-3-phosphorylcholine TRITON X-100™ prepare at 6.249 mg/ml in reaction buffer to equal 10 uM.

REACTION MIXTURE—

A measured volume of racemic dipheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure:
1. Add 0.2 ml reaction mixture to all wells;
2. Add 10 ul test compound (or solvent blank) to appropriate wells, mix 20 seconds;
3. Add 50 nanograms of $sPLA_2$ (10 microliters) to appropriate wells;
4. Incubate plate at 40° C. for 30 minutes;
5. Read absorbance of wells at 405 nanometers with an automatic plate reader.

Tests were done in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were re-assayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ values were determined by plotting log concentration versus inhibition values in the range from 10–90% inhibition.

Results

| Compound of Example# | $IC_{50}$ (uM) (micromolar) |
|---|---|
| 1 | 0.108 |
| 2 | 0.013 |
| 3 | 0.106 |
| 4 | 0.010 |
| 5 | 0.007 |
| 6 | 0.132 |
| 7 | 0.010 |
| 8 | 0.073 |
| 9 | 0.009 |

-continued

| Compound of Example# | IC$_{50}$ (uM) (micromolar) |
|---|---|
| 10 | 0.806 |
| 11 | 0.082 |
| 12 | 0.100 |
| 13 | 0.011 |
| 14 | 0.109 |
| 15 | 0.010 |
| 16 | 0.453 |
| 17 | 0.010 |
| 18 | 0.190 |
| 19 | 0.035 |
| 20 | 0.638 |
| 21 | 0.044 |

While the present invention has been illustrated above by certain specific embodiments, it is not intended that these specific examples should limit the scope of the invention as described in the appended claims.

EXPERIMENTAL

All of the products of the Examples described below as well as intermediates used in the following procedures showed satisfactory NMR and IR spectra. They also had the correct mass spectral values.

Example 1

2-[[3-(2-Amino-1,2-dioxoethyl)-2-ethyl-1-benzyl-1,6,7,8-tetrahydrocyclo-pent[g]indol-4-yl]oxy]acetic acid methyl ester

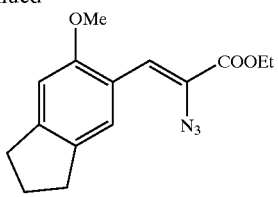

A. Preparation of 2,3-dihydro-6-methoxy-1H-indene-5-carboxaldehyde. Phosphorus oxychloride (67.1 mL, 0.710 mol) was added to N,N-dimethylformamide (60 mL) at 0° C. After stirring for 0.5 hr, 2,3-dihydro-6-methoxy-1H-indene (50.0 g, 0.338 mol) was added and the resulting mixture heated carefully at 80° C. for 4 h. The mixture was cooled to room temperature, poured over crushed ice, and stirred for 18 h. The resulting precipitate was collected via vacuum filtration. Recrystallization (absolute ethanol) provided 43.5 g (73%) of the title product as yellow plates.

B. Preparation of 3-(2,3-dihydro-6-methoxy-1H-inden-5-yl)-2-azido-2-propenoic acid ethyl ester.

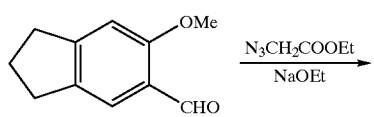

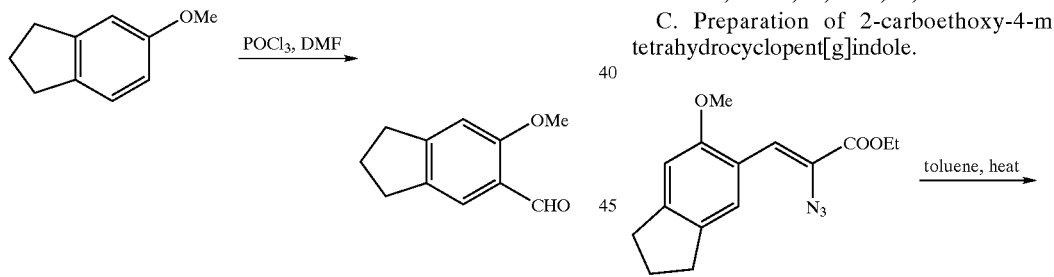

Sodium (13.8 g, 0.600 mol) was dissolved in absolute ethanol (400 mL). After cooling to −10° C., a mixture of 2,3-dihydro-6-methoxy-1H-indene-5-carboxaldehyde (26.5 g, 0.150 mol) and ethyl azidoacetate (72.0 g, 0.558 mol) in diethyl ether (100 mL) was added dropwise in such a manner that the temperature did not rise above −10° C. The mixture was allowed to warm to 20° C. over 3 h. After gas evolution had ceased, the mixture was poured into water (700 ml). The mixture was extracted thrice with diethyl ether and the combined organic fractions were washed with water, saturated sodium chloride solution, dried (sodium sulfate), filtered, and concentrated in vacuo. The resulting oil was cooled to −10° C. for 24 hours which resulted in the formation of a solid. This material was slurried in hexanes and collected via vacuum filtration (15.6 g). The filtrate was concentrated in vacuo and chromatographed (silica gel, 5% ethyl acetate/95% hexane) to provide an additional 7.3 g (53% total yield) of the title product as a yellow crystalline material: mp 64–66° C. $^1$H NMR (CDCl$_3$) δ 8.05 (s, 1H), 7.41 (s, 1H), 6.79 (s, 1H), 4.38 (q, J=7.3 Hz, 2H), 3.84 (s, 3H), 2.89 (q, J=7.3 Hz, 4H), 2.07 (quintet, J=7.3 Hz, 2H), 1.38 (t, J=7.3 Hz, 3H); $^{13}$C NMR (CDCl$_3$) δ 163.97, 156.87, 147.90, 135.74, 125.81, 124.10, 120.36, 120.06, 61.99, 55.80, 33.92, 33.70, 32.16, 25.64, 14.26; MS FD+ m/e 287 (p); IR (CHCl$_3$, cm$^{-1}$) 2961, 2122, 1704, 1081.

Anal. Calcd for C$_{15}$H$_{17}$N$_3$O$_3$: C, 62.71; H, 5.96; N, 14.62. Found: C, 62.46; H, 5.99; N, 14.40.

C. Preparation of 2-carboethoxy-4-methoxy-1,6,7,8-tetrahydrocyclopent[g]indole.

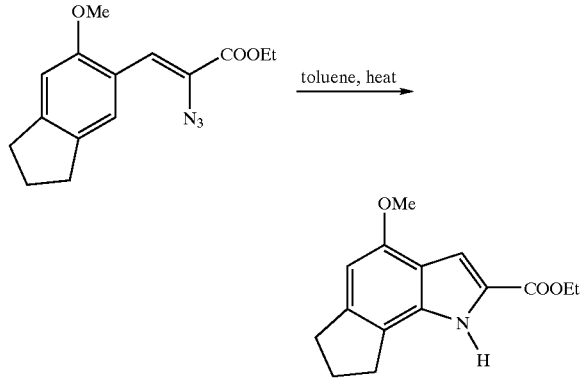

A mixture of 3-(2,3-dihydro-6-methoxy-1H-inden-5-yl)-2-azido-2-propenoic acid ethyl ester (7.28 g, 25.3 mmol) in toluene (200 mL) was refluxed for 6 h. Upon cooling to room temperature a crystalline precipitate formed that was collected via vacuum filtration and washed with hexanes to provide 3.38 g (52%) of the title product as white needles: mp 185–187° C. $^1$H NMR (CDCl$_3$) δ 8.97 (bs, 1H, —NH), 7.36 (d, J=2.2 Hz, 1H), 6.46 (s, 1H), 4.41 (q, J=7.0 Hz, 2H), 3.93 (s, 3H), 3.03 (q; J=6.6 Hz, 4H), 2.22 (quintet, J=7.3 Hz, 2H), 1.42 (t, J=7.3 Hz, 3H); $^{13}$C NMR (CDCl$_3$) δ 162.31, 153.71, 143.03, 135.07, 125.55, 118.20, 117.80, 107.36, 97.40, 60.79, 55.39, 33.93, 29.32, 25.26, 14.42; MS ES+ m/e 260 (p+1); IR (CHCl$_3$, cm$^{-1}$) 3400, 1698, 1258.

Anal. Calcd for C$_{15}$H$_{17}$NO$_3$: C, 69.48; H, 6.61; N, 5.40. Found: C, 69.71; H, 6.62; N, 5.45.

D. Preparation of 1-benzyl-2-carboxy-4-methoxy-1,6,7,8-tetrahydrocyclopent[g]indole.

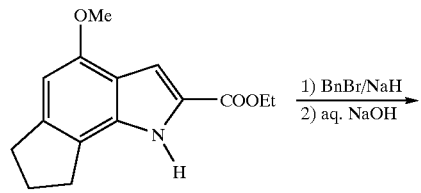

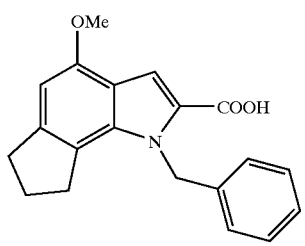

To a slurry of a 60% oil suspension of sodium hydride (7.00 g, 0.175 mol) in N,N-dimethylformamide (350 mL) was added 2-carboethoxy-4-methoxy-1,6,7,8-tetrahydrocyclopent[g]indole (34.5 g, 0.133 mol) and the resulting mixture stirred for 15 min. Benzyl bromide (21.0 mL, 0.176 mol) was added and the mixture allowed to stir at room temperature for 48 h. The mixture was dissolved in approximately 300 mL 1:1 methanol/tetrahydrofuran and treated with aqueous 5 N sodium hydroxide solution at 50° C. until nearly all of the precipitate had dissolved. The mixture was filtered, and the filtrate adjusted to pH 2 with concentrated hydrochloric acid. The resulting precipitate was collected via vacuum filtration, washed with water, and dried under vacuum at 40° C. for 48 h to provide 37.5 g (87%) of the title product as a white solid: mp 248–250° C. (dec). $^1$H NMR (DMSO-d$_6$) δ 12.68 (bs, 1H), 7.29 (s, 1H), 7.22 (m, 3H), 6.80 (d, J=7.0 Hz, 2H), 6.52 (s, 1H), 5.94 (bs, 2H), 3.89 (s, 3H), 2.93 (m, 2H), 2.84 (t, J=7.3 Hz, 2H), 1.94 (quintet, J=7.3 Hz, 2H); $^{13}$C NMR (DMSO-d$_6$) δ 163.36, 162.59, 143.14, 140.25, 137.33, 128.47, 126.63, 126.11, 124.90, 117.19, 116.06, 108.63, 97.65, 55.09, 47.82, 32.99, 30.13, 24.48; MS ES+ m/e 322 (p+1); IR (KBr, cm$^{-1}$) 3000, 1662, 1610, 1497.

Anal. Calcd for C$_{20}$H$_{19}$NO$_3$: C, 74.75; H, 5.96; N, 4.36. Found: C, 74.59; H, 5.64; N, 4.38.

E. Preparation of 2-acetyl-1-benzyl-4-methoxy-1,6,7,8-tetrahydrocyclopent[g]indole.

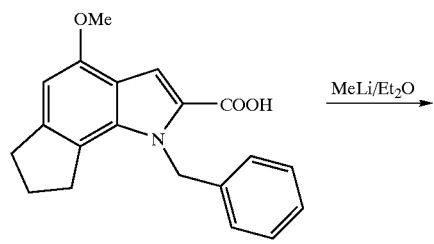

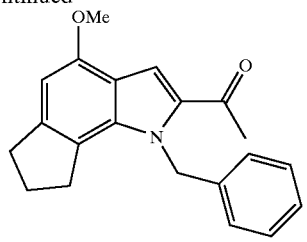

To a solution of 1-benzyl-2-carboxy-4-methoxy-1,6,7,8-tetrahydrocyclopent[g]indole (20.0 g, 62.2 mmol) in tetrahydrofuran (350 mL) was added 1.4 M methyllithium in ether (134 mL, 189 mmol) dropwise at room temperature and the resulting mixture stirred for 2 h. The mixture was poured into saturated ammonium chloride solution and acidified with concentrated hhydrochloric acid. The resulting mixture was extracted with ether. The organic layer was separated, dried (sodium sulfate), filtered, and concentrated in vacuo to provide an amber oil. Chromatography (silica gel, 10% ethyl acetate/90% hexanes) provided 10.4 g (52%) of the title compound as a yellow solid: mp 147–149° C. $^1$H NMR (CDCl$_3$) δ 7.52 (s, 1H), 7.23 (m, 3H), 6.90 (d, J=6.6 Hz, 2H), 6.48 (s, 1H), 6.00 (bs, 2H), 3.97 (s, 3H), 3.07 (t, J=7.0 Hz, 2H), 2.96 (t, J=7.7 Hz, 2H), 2.55 (s, 3H), 2.09 (quintet, J=7.3 Hz, 2H); $^{13}$C NMR (CDCl$_3$) δ 190.43, 153.78, 145.14, 140.14, 138.65, 132.83, 128.49, 126.98, 125.49, 117.80, 116.77, 111.80, 97.49, 55.35, 49.02, 33.73, 30.87, 27.85, 25.12; MS ES+ m/e 320 (p+1); IR (CHCl$_3$, cm$^{-1}$) 1665, 1606, 1490.

Anal. Calcd for C$_{21}$H$_{21}$NO$_2$, C, 78.97; H, 6.63; N, 4.39. Found: C, 79.12; H, 6.80; N, 4.56.

F. Preparation of 1-benzyl-2-[2-(2-hydroxyethyl)]-4-methoxy-1,6,7,8-tetrahydrocyclopent[g]indole.

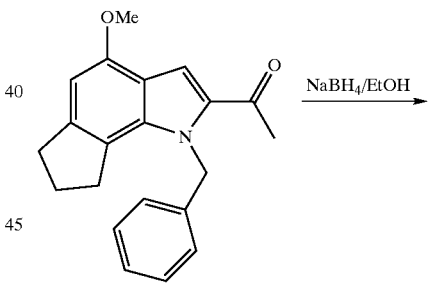

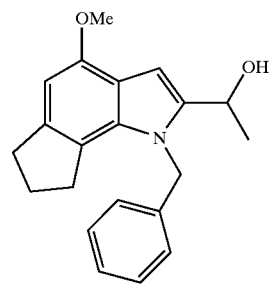

To a solution of 2-acetyl-1-benzyl-4-methoxy-1,6,7,8-tetrahydrocyclopent[g]indole (4.00 g, 12.5 mmol) in absolute ethanol (100 mL) was added sodium borohydride (0.94 g, 25 mmol) at room temperature and the resulting mixture stirred for 18 h. The reaction was quenched with water and the resulting mixture concentrated in vacuo. The aqueous residue was extracted twice with ethyl acetate. The combined ethyl acetate layers were washed with saturated sodium chloride solution, dried (sodium sulfate), and concentratred in vacuo to provide 3.6 g (90%) of the title product as an off-white solid. An analytical sample was prepared by recrystallization from ethyl acetate/hexane to give white crystals: mp 136–138° C. $^1$H NMR (CDCl$_3$) δ 7.25 (m, 3H), 6.88 (J=6.2 Hz, 2H), 6.69 (s, 1H), 6.51 (s, 1H), 5.70 (d, J=17.5 Hz, 1H), 5.62 (d, J=17.9 Hz, 1H), 4.83 (m, 1H), 3.97 (s, 3H), 3.05 (m, 1H), 2.97 (m, 3H), 2.08 (hextet, J=7.7 Hz, 2H), 1.96 (d, J=6.2 Hz, 3H); $^{13}$C NMR (CDCl$_3$) δ 152.49, 140.56, 140.20, 139.91, 136.02, 128.79, 127.28, 125.40, 117.58, 116.86, 97.21, 97.06, 62.76, 55.35, 47.71, 33.30, 30.59, 25.38, 22.34; MS ES+ m/e 322 (p+1); IR (CHCl$_3$, cm$^{-1}$) 1605, 1497, 1365.

Anal. Calcd for C$_{21}$H$_{23}$NO$_2$: C, 78.47; H, 7.21; N, 4.36. Found: C, 78.73; H, 7.22; N, 4.51.

G. Preparation of 2-[(2-ethyl-1-benzyl-1,6,7,8-tetrahydrocyclopent[g]indol-4-yl)oxy]acetic acid methyl ester.

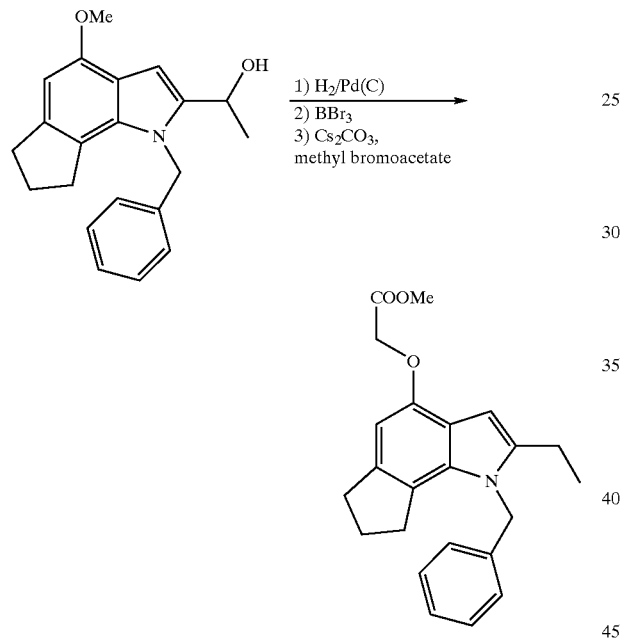

To a solution of 1-benzyl-2-[2-(2-hydroxyethyl)]-4-methoxy-1,6,7,8-tetrahydrocyclopent[g]indole (3.50 g, 10.9 mmol) in 1:1:1 ethyl acetate/tetrahydrofuran/ethanol was added methylene chloride (2 mL) and 10% palladium-on-carbon (350 mg). The mixture was hydrogenated at 40 psi for 2.5 h. The mixture was filtered through a pad of Celite™ and silica gel, and the resulting solution was concentrated in vacuo. The residue was dissolved in chloroform (20 mL), cooled to 0° C., and treated with boron tribromide (0.90 mL, 9.5 mmol). After stirring for 1 h the mixture was poured over ice and extracted with chloroform. The organic layer was washed once with water, once with saturated sodium chloride solution, dried (sodium sulfate), filtered, and concentrated in vacuo. The residue was dissolved in N,N-dimethylformamide (10 mL) and treated with cesium carbonate (1.46 g, 4.14 mmol) and methyl bromoacetate (0.40 mL, 4.2 mmol). The mixture was stirred at room temperature for 24 h and additional portions of cesium carbonate and methyl bromoacetate were added. After stirring for 8 h, the mixture was diluted with water and extracted thrice with ethyl acetate. The combined ethyl acetate layers were washed four times with water, once with saturated sodium chloride solution, dried (sodium sulfate), filtered, and concentrated in vacuo. Chromatography (silica gel, 5% ethyl acetate/95% hexanes) of the residue provided 287 mg (21%) of the title product as a white solid. An analytical sample was prepared by recrystallization (hexanes) to provide white crystals: mp 117–119° C. $^1$H NMR (CDCl$_3$) δ 7.25 (m, 3H), 6.88 (J=6.6 Hz, 2H), 6.52 (s, 1H), 6.38 (s, 1H), 5.44 (s, 2H), 4.80 (s, 2H), 3.85 (s, 3H), 3.01 (t, J=7.0 Hz, 2H), 2.93 (t, J=7.7 Hz, 2H), 2.61 (q, J=7.3 Hz, 2H), 2.06 (quintet, J=7.3 Hz, 2H), 1.31 (t, J=7.3 Hz, 3H); MS ES+ m/e 364 (p+1); IR (CHCl$_3$, cm$^{-1}$) 2955, 1760, 1738, 1496.

Anal. Calcd for C$_{23}$H$_{25}$NO$_3$: C, 76.01; H, 6.93; N, 3.85. Found: C, 75.63; H, 7.27; N, 4.15.

H. Preparation of 2-[[3-(2-amino-1,2-dioxoethyl)-2-ethyl-1-benzyl-1,6,7,8-tetrahydrocyclo-pent[g]indol-4-yl]oxy]acetic acid methyl ester

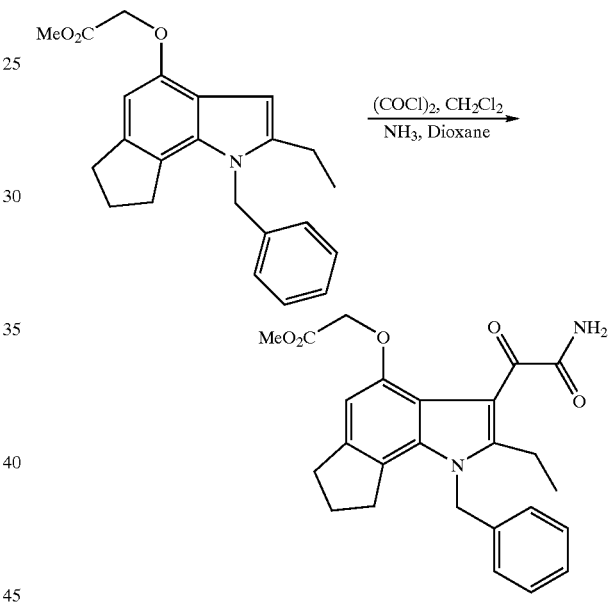

A solution of 2-[(2-ethyl-1-benzyl-1,6,7,8-tetrahydrocyclopent[g]indol-4-yl)oxy]acetic acid methyl ester (169 mg, 0.465 mmol) in methylene chloride (3 mL) was cooled to 0° C. and treated with oxalyl chloride (0.162 mL, 1.86 mmol). The mixture was stirred for 40 min then concentrated in vacuo, diluted with methylene chloride, and concentrated in vacuo. The residue was dissolved in methylene chloride (3 mL) and treated with 0.5 M ammonia in dioxane (6 mL). After stirring for 30 min the mixture was concentrated in vacuo to provide 180 mg (89%) of the title compound as a yellow solid: mp 190–199° C. (dec). $^1$H NMR (CDCl$_3$) δ 7.32 (m, 3H), 6.97 (d, J=6.1 Hz, 2H), 6.62 (bs, 1H, —NH), 6.50 (s, 1H), 5.62 (bs, 1H, —NH), 5.51 (s, 2H), 4.74 (s, 2H), 3.82 (s, 3H), 2.90 (m, 6H), 2.04 (quintet, J=7.3 Hz, 2H), 1.19 (t, J=7.3 Hz, 3H); MS ES+ m/e 435 (p+1); IR (KBr, cm$^{-1}$) 3406, 1654, 1640, 1218.

Anal. Calcd for C$_{25}$H$_{26}$N$_2$O$_5$: C, 69.11; H, 6.03; N, 6.45. Found: C, 67.97; H, 6.06; N, 6.60.

Example 2

2-[[3-(2-Amino-1,2-dioxoethyl)-2-ethyl-1-benzyl-1,6,7,8-tetrahydrocyclo-pent[g]indol-4-yl]oxy]acetic acid

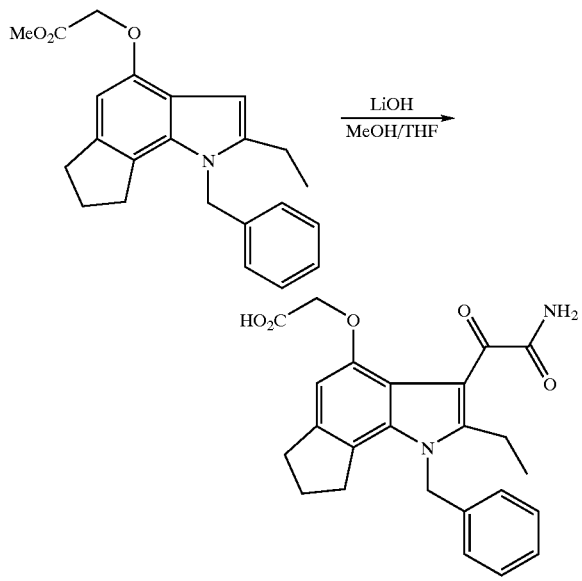

Preparation of 2-[[3-(2-amino-1,2-dioxoethyl)-2-ethyl-1-benzyl-1,6,7,8-tetrahydrocyclo-pent[g]indol-4-yl]oxy] acetic acid. A solution 2-[[3-(2-amino-1,2-dioxoethyl)-2-ethyl-1-benzyl-1,6,7,8-tetrahydrocyclopent[g]indol-4-yl] oxy]acetic acid methyl ester (10 mg, 0.023 mmol) in 1:1 tetrahydrofuran/methanol (3 mL) was treated with 1 M aqueous lithium hydroxide solution (1.5 mL) The resulting mixture was warmed to 40° C. and stirred for 2 h. The mixture was concentrated in vacuo and treated with dilute hydrochloric acid. The resulting precipitate was collected via vacuum filtration. The solid was slurried with methanol, and the resulting solid collected via vacuum filtration to provide 5 mg (52%) of the title product as a white solid. $^1$H NMR (CDCl$_3$) δ 7.25 (m, 3H), 7.03 (bs, 1H, —NH), 6.90 (d, J=6 Hz, 2H), 6.57 (s, 1H), 6.45 (bs, 1H, —NH), 5.50 (s, 2H), 4.77 (s, 2H), 2.90 (m, 6H), 2.04 (quintet, J=7 Hz, 2H), 1.18 (t, J=7 Hz, 3H); TOS MS ES$^+$ exact mass calculated for C$_{24}$H$_{25}$N$_2$O$_5$ (p+1): m/z=421.1763. Found: 421.1767.

Example 3

2-[[3-(2-Amino-1,2-dioxoethyl)-2-methyl-1-benzyl-1,6,7,8-tetrahydrocyclo-pent[g]indol-4-yl]oxy]acetic acid methyl ester A. Preparation of 1-benzyl-2-hydroxymethyl-4-methoxy-1,6,7,8-tetrahydrocyclopent[g]indole. A solution of 1-benzyl-2-carboxy-4-methoxy-1,6,7,8-tetrahydrocyclopent[g]indole (3.21 g, 10.0 mmol) in tetrahydrofuran (70 mL) was treated carefully with lithium aluminum hydride (0.58 g, 15 mmol) at room temperature for 18 h. Additional small portions of lithium aluminum hydride were added until the conversion of starting material was complete via TLC. The reaction was quenched by the addition of excess sodium sulfate decahydrate and the resulting suspension filtered. The filtrate was dried (sodium sulfate), filtered, and concentrated in vacuo to provide a quantitative yield of the title compound as white crystals. An analytical sample was obtained by recrystallization (ethyl acetate/hexanes): mp 135–140° C. $^1$H NMR (CDCl$_3$) δ 7.20–7.30 (m, 3H), 6.91 (d, J=7 Hz, 2H), 6.64 (s, 1H), 6.54 (s, 1H), 5.62 (s, 2H), 4.63 (s, 2H), 3.97 (s, 3H), 3.03 (t, J=7 Hz, 2H), 2.97 (t, J=7 Hz, 2H), 2.20 (bs, 1H), 2.08 (quintet, J=7 Hz, 2H); MS ES+ m/e 308 (p+1); IR (CHCl$_3$, cm$^{-1}$) 2944, 1595, 1497.

Anal. Calcd for C$_{20}$H$_{21}$NO$_2$: C, 78.15; H, 6.89; N, 4.56. Found: C, 78.52; H, 6.82; N, 4.61.

B. Preparation of 1-benzyl-2-methyl-4-methoxy-1,6,7,8-tetrahydrocyclopent[g]indole.

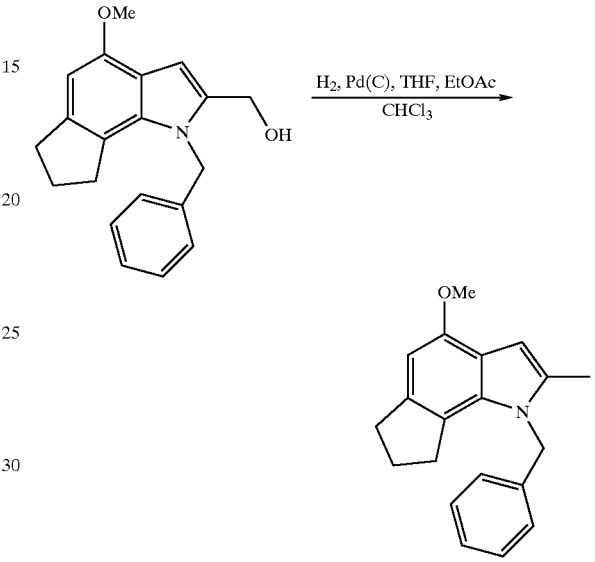

To a nitrogen-purged solution of 1-benzyl-2-hydroxymethyl-4-methoxy-1,6,7,8-tetrahydrocyclopent[g]indole (2.0 g, 6.5 mmol) and chloroform (3 mL) in 1:1 tetrahydrofuran/absolute ethanol (200 mL) was added 10% palladium-on-carbon (400 mg). The resulting suspension was hydrogenated at 45–50 psi for 18 h. The mixture was filtered through Celite™ and concentrated in vacuo to provide a solid. Chromatography (silica gel, 7% ethyl acetate/ 93% hexanes) provided 0.50 g (26%) of the title compound as a white solid: mp 128–130° C. $^1$H NMR (CDCl$_3$) δ 7.24 (m, 3H), 6.88 (d, J=7.0 Hz, 2H), 6.46 (s, 1H), 6.40 (bs, 1H), 5.42 (s, 2H), 3.93 (s, 3H), 3.00 (t, J=7.3 Hz, 2H), 2.93 (t, J=7.7 Hz, 2H), 2.28 (s, 3H), 2.05 (quintet, J=7.3 Hz, 2H); MS ES+ m/e 292 (p+1); IR (KBr, cm$^{-1}$) 2939, 1596, 1497, 1251.

Anal. Calcd for C$_{20}$H$_{21}$NO: C, 82.44; H, 7.26; N, 4.81. Found: C, 82.14; H, 7.29; N, 4.83.

B. Preparation of 2-[(2-methyl-1-benzyl-1,6,7,8-tetrahydrocyclopent[g]indol-4-yl)oxy]acetic acid methyl ester.

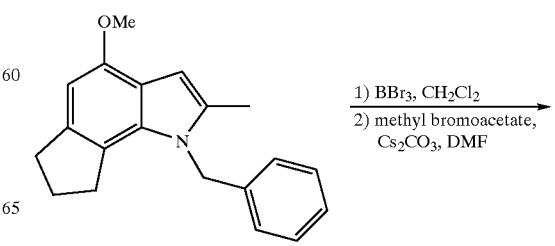

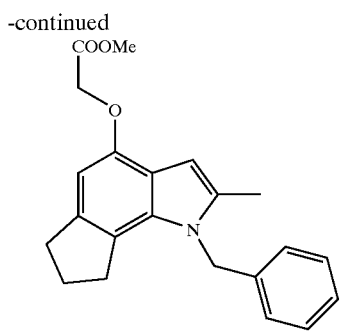

A solution of 1-benzyl-2-methyl-4-methoxy-1,6,7,8-tetrahydrocyclopent[g]indole (2.2 g, 7.6 mmol) in chloroform (40 mL) was treated with boron tribromide (2.8 mL, 30 mmol) at 0° C. The mixture was warmed to room temperature and stirred for 2.5 h. The mixture was poured into water and extracted with chloroform. The organic layer was washed once with water, once with saturated sodium chloride solution, dried (sodium sulfate), filtered, and concentrated in vacuo to provide an oil. A solution of this material (oil) in N,N-dimethylformamide (35 mL) was treated with cesium carbonate (3.21 g, 9.10 mmol) and methyl bromoacetate (0.86 mL, 9.1 mmol) at room temperature. After stirring for 18 h, the mixture was poured into water and extracted with ethyl acetate. The organic layer was washed once with water, once with saturated sodium chloride solution, dried (sodium sulfate), filtered, and concentrated in vacuo. Chromatography (silica gel, 10% ethyl acetate/90% hexanes) provided 0.43 g (16%) of the title product as a white solid: mp 135–138° C. $^1$H NMR (CDCl$_3$) δ 7.22 (m, 3H), 6.88 (d, J=7.0 Hz, 2H), 6.47 (s, 1H), 6.36 (s, 1H), 5.42 (s, 2H), 4.76 (s, 2H), 3.82 (s, 3H), 3.00 (t, J=7.3 Hz, 2H), 2.90 (t, J=7.3 Hz, 2H), 2.29 (s, 3H), 2.04 (quintet, J=7.0 Hz, 2H); MS ES+ m/e 350 (p+1); IR (CHCl$_3$, cm$^{-1}$) 2955, 1760, 1737, 1496.

Anal. Calcd for C$_{22}$H$_{23}$NO$_3$: C, 75.62; H, 6.63; N, 4.01. Found: C, 77.15; H, 6.81; N, 4.42.

C. Preparation of 2-[[3-(2-amino-1,2-dioxoethyl)-2-methyl-1-benzyl-1,6,7,8-tetrahydrocyclopent[g]indol-4-yl]oxy]acetic acid methyl ester

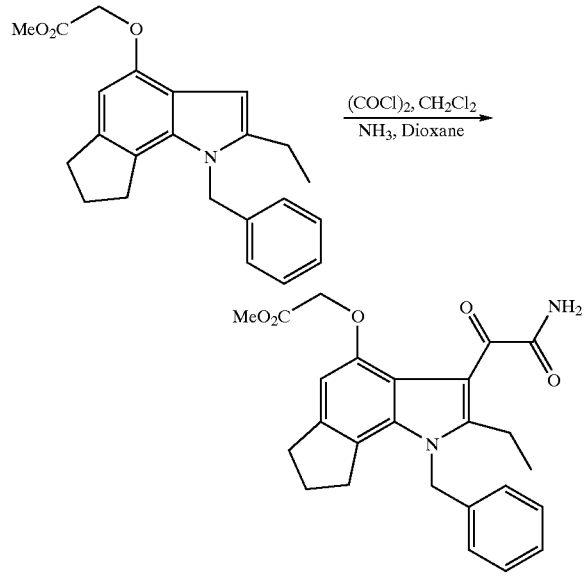

A solution of 2-[(2-methyl-1-benzyl-1,6,7,8-tetrahydrocyclopent[g]indol-4-yl)oxy]acetic acid methyl ester (0.38 g, 1.1 mmol) in methylene chloride (8 mL) was cooled to 0° C. and treated with oxalyl chloride (0.47 mL, 5.4 mmol). The resulting mixture was stirred for 1 h then concentrated in vacuo. The residue was dissolved in methylene chloride and concentrated in vacuo. The residue was again dissolved in methylene chloride (5 mL) and treated with a 1M solution of ammonia in dioxane (10 mL). The mixture was stirred for 30 min and concentrated in vacuo. The resulting material was slurried in hot ethyl acetate and the resulting solids collected via vacuum filtration to provide 0.28 g (61%) of the title compound as a bright yellow solid: mp 226–228° C. $^1$H NMR (DMSO$_6$) δ 7.63 (bs, 1H), 7.30 (m, 4H), 6.92 (d, J=7.3 Hz, 2H), 6.50 (s, 1H), 5.54 (s, 2H), 4.71 (s, 2H), 3.70 (s, 3H), 2.96 (t, J=7.3 Hz, 2H), 2.82 (t, J=7.3 Hz, 2H), 2.41 (s, 3H), 1.96 (quintet, J=7.0 Hz, 2H); IR (CHCl$_3$, cm$^{-1}$) 3154, 1640, 1406.

FAB+ MS exact mass calculated for C$_{24}$H$_{25}$N$_2$O$_5$: m/z= 421.1763 (p+1). Found: 421.1768.

Example 4

2-[[3-(2-Amino-1,2-dioxoethyl)-2-methyl-1-benzyl-1,6,7,8-tetrahydrocyclopent[g]indol-4-yl]oxy]acetic acid

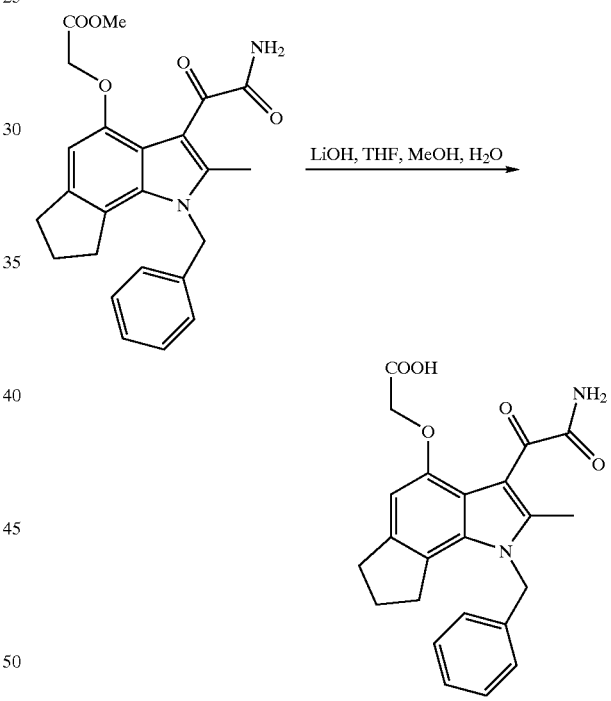

Preparation of 2-[[3-(2-amino-1,2-dioxoethyl)-2-methyl-1-benzyl-1,6,7,8-tetrahydrocyclopent[g]indol-4-yl]oxy]acetic acid. A solution of 2-[[3-(2-amino-1,2-dioxoethyl)-2-methyl-1-benzyl-1,6,7,8-tetrahydrocyclopent[g]indol-4-yl]oxy]acetic acid methyl ester (95 mg, 0.23 mmol) in a 1:1 mixture of methanol/tetrahydrofuran (1 mL) was treated with excess 1M lithium hydroxide for 19 h at room temperature. The mixture was concentrated in vacuo, diluted with water, and acidified with 5N hydrochloric acid. The resulting precipitate was collected via vacuum filtration and recrystallized (absolute ethanol) to provide 65 mg (71%) of the title product as yellow crystals: mp 255–257° C. $^1$H NMR (DMSO$_6$) δ 12.84 (bs, 1H, —OH), 7.69 (bs, 1H), 7.33 (m, 4H), 6.92 (d, J=7.0 Hz, 2H), 6.46 (s, 1H), 5.54 (s, 2H), 4.61 (s, 2H), 2.95 (t, J=7.0 Hz, 2H), 2.82 (t, J=7.3 Hz, 2H), 2.42 (s, 3H), 1.96 (quintet, J=7.0 Hz, 2H); MS ES+ m/e 407 (p+1).

Anal. Calcd for $C_{23}H_{22}N_2O_5$: C, 67.97; H, 5.46; N, 6.89. Found: C, 68.07; H, 5.31; N, 7.22.

Example 5

2-[4-(2-Benzenesulfonylamino-2-oxoethoxy)-1-benzyl-2-methyl-1,6,7,8-tetrahydro-1-aza-as-indacen-3-yl]-2-oxoacetamide

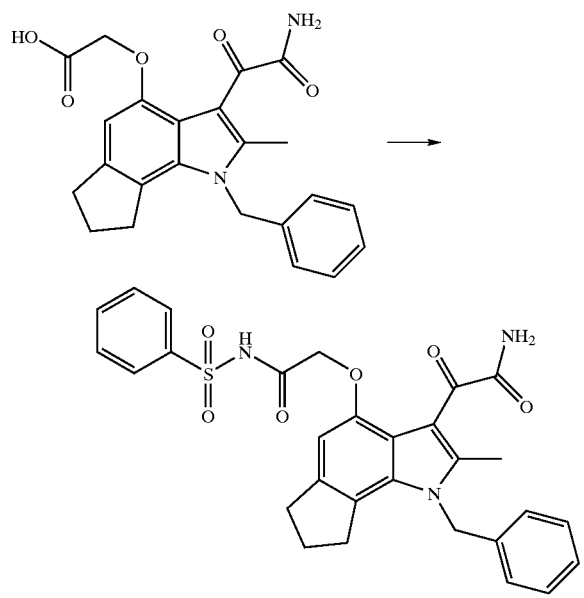

Preparation of 2-[4-(2-benzenesulfonylamino-2-oxoethoxy)-1-benzyl-2-methyl-1,6,7,8-tetrahydro-1-aza-as-indacen-3-yl]-2-oxoacetamide. To a solution of 2-[[3-(2-amino-1,2-dioxoethyl)-2-methyl-1-benzyl-1,6,7,8-tetrahydrocyclopent[g]indol-4-yl]oxy]acetic acid (83 mg, 0.20 mmol) in methylene chloride (3 mL) was added diisopropylethylamine (0.1 mL, 0.6 mmol), 4-N,N-dimethylaminopyridine (24 mg, 0.20 mmol), benzenesulfonamide (31 mg, 0.20 mmol), and 1-(3-dimethylaminopropyl)-3-ethylcarbodiimide hydrochloride (58 mg, 0.37 mmol). The mixture was stirred at room temperature for 18 h. Additional portions of 1-(3-dimethylaminopropyl)-3-ethylcarbodiimide hydrochloride (29 mg), diisopropylethylamine (51 µL), and benzenesulfonamide (16 mg) were added and the resulting mixture stirred for 5 h. The mixture was poured into 1 N hydrochloric acid and extracted three times with methylene chloride. The combined methylene chloride extracts were washed once with water, once with saturated aqueous sodium chloride solution, dried (sodium sulfate), filtered, and concentrated in vacuo. Chromatography (silica gel, 7% methanol/93% chloroform) of the residue provided a solid that was slurried in hot ethyl acetate. Collection of the resulting solid via vacuum filtration provided 10 mg (9%) of the title compound as a yellow solid. $^1$H NMR (CDCl$_3$) δ 10.95 (s, 1H), 7.91 (d, J=7.7 Hz, 2H), 7.55 (t, J=7.4 Hz, 1H), 7.38 (t, J=7.7 Hz, 2H), 7.20–7.35 (m, 4H), 6.91 (d, J=7.0 Hz, 2H), 6.21 (s, 1H), 5.84 (bs, 1H), 5.48 (s, 2H), 4.55 (s, 2H), 2.98 (t, J=7.3 Hz, 2H), 2.71 (t, J=7.7 Hz, 2H), 2.48 (s, 3H), 2.01 (quintet, J=7.7 Hz, 2H).

TOF MS ES$^+$ exact mass calculated for $C_{29}H_{28}N_3O_6S$ (p+1): m/z=546.1699. Found: 546.1713.

Example 6

2-[[3-(2-Amino-1,2-dioxoethyl)-2-methyl-1-(3-fluorobenzyl)-1,6,7,8-tetrahydrocyclopent[g]indol-4-yl]oxy]acetic Acid methyl ester

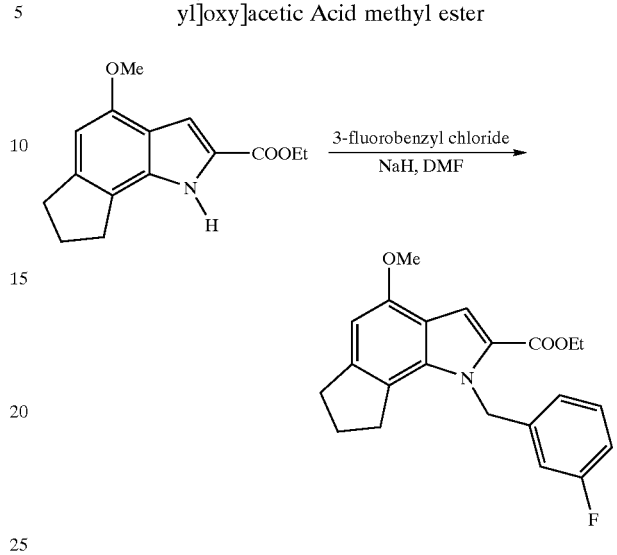

A. Preparation of 1-(3-fluorobenzyl)-2-carboethoxy-4-methoxy-1,6,7,8-tetrahydrocyclopent[g]indole. A solution of 2-carboethoxy-4-methoxy-1,6,7,8-tetrahydrocyclopent[g]indole (3.00 g, 11.6 mmol) in N,N-dimethylformamide (50 mL) was treated with a 60% suspension of sodium hydride in mineral oil (0.70 g) followed by 3-fluorobenzyl chloride (3.17 g, 15.0 mmol) at room temperature for 18 h. Additional portions of sodium hydride (0.10 g) and 3-fluorobenzyl chloride (0.4 g) were added and the resulting mixture stirred for 4 h. The mixture was diluted with water and extracted three times with ethyl acetate. The combined organic layers were washed once with water, once with saturated aqueous sodium chloride solution, dried (sodium sulfate), filtered, and concentrated in vacuo. Chromatography (silica gel, 5% ethyl acetate/95% hexanes) of the residue provided 1.40 g (33%) of the title compound as a white solid: 109–112° C. $^1$H NMR (CDCl$_3$) δ 7.52 (s, 1H), 7.20 (m, 1H), 6.86 (dt, J=8.4, 2.3 Hz, 1H), 6.69 (d, J=7.6 Hz, 1H), 6.56 (d, J=9.2 Hz, 1H), 6.47 (s, 1H), 5.95 (bs, 2H), 4.26 (q, J=6.9 Hz, 2H), 3.94 (s, 3H), 3.02 (t, J=7.3 Hz, 2H), 2.95 (t, J=7.6 Hz, 2H), 2.08 (quintet, J=7.3 Hz, 2H), 1.32 (t, J=6.9 Hz, 3H); MS ES+ m/e 368 (p+1); IR (CHCl$_3$, cm$^{-1}$) 2960, 1700, 1495, 1194.

Anal. Calcd for $C_{22}H_{22}FNO_3$: C, 71.92; H, 6.04; N, 3.81. Found: C, 71.67; H, 5.93; N, 3.75.

B. Preparation of 1-(3-fluorobenzyl)-2-hydroxymethyl-4-methoxy-1,6,7,8-tetrahydrocyclopent[g]indole.

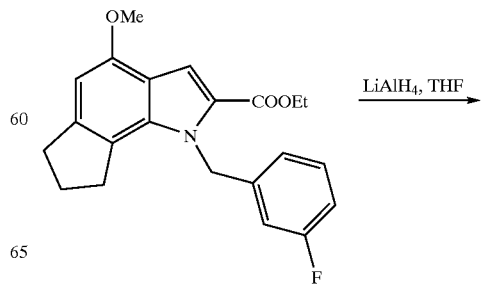

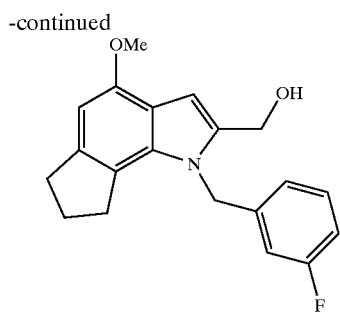

A solution of 1-(3-fluorobenzyl)-2-carboethoxy-4-methoxy-1,6,7,8-tetrahydrocyclopent[g]indole (5.60 g, 15.2 mmol) in tetrahydrofuran (150 mL) was treated with lithium aluminum hydride (0.635 g, 16.7 mmol) at room temperature for 20 h. Excess sodium sulfate decahydrate was added and the resulting mixture stirred and then dried with anhydrous sodium sulfate. The mixture was filtered and concentrated in vacuo to provide 4.17 g (85%) of the title compound as a solid. Recrystallization (ethyl acetate/hexanes) provided an analytical sample as white crystals: mp 147–149° C. $^1$H NMR (DMSO-d$_6$) δ 7.32 (dd, J=14.2, 6.5 Hz, 1H), dt (J=8.8, 2.3 Hz, 1H), 6.69 (d, J=7.6 Hz, 1H), 6.62 (d, J=9.6 Hz, 1H), 6.47 (s, 1H), 6.46 (s, 1H), 5.57 (s, 2H), 5.24 (t, J=5.4 Hz, 1H, —OH), 4.50 (d, J=5.4 Hz, 2H), 3.84 (s, 3H), 2.88 (t, J=7.6 Hz, 2H), 2.84 (t, J=8.0 Hz, 2H), 1.95 (quintet, J=6.9 Hz, 2H); MS ES+ m/e 326 (p+1); IR (KBr, cm$^{-1}$) 3427 (b), 1593, 1244.

Anal. Calcd for C$_{20}$H$_{20}$FNO$_2$: C, 73.83; H, 6.20; N, 4.30. Found: C, 73.62; H, 6.18; N, 4.35.

B. Preparation of 2-[(2-methyl-1-(3-fluorobenzyl)-1,6,7,8-tetrahydrocyclopent[g]indol-4-yl)oxy]acetic acid methyl ester.

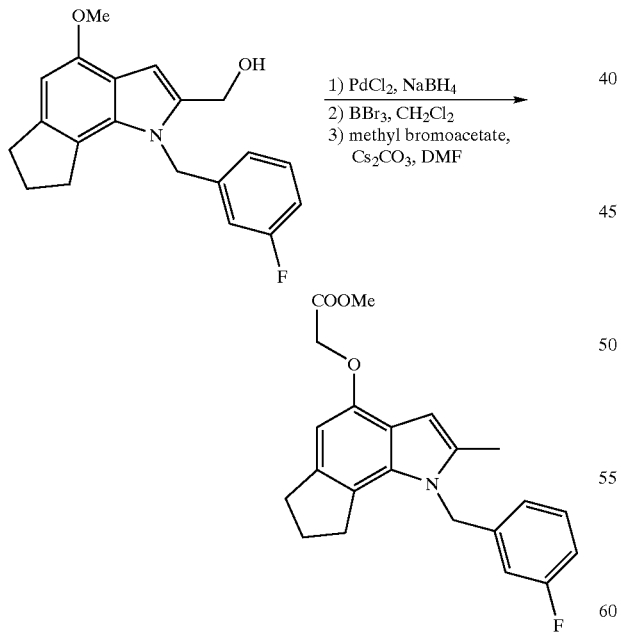

A solution of 1-(3-fluorobenzyl)-2-hydroxymethyl-4-methoxy-1,6,7,8-tetrahydrocyclopent[g]indole (3.80 g, 11.7 mmol) in tetrahydrofuran (350 mL) and methanol (38 mL) was treated with palladium(II) chloride (3.63 g, 20.4 mmol) and sodium borohydride (1.33 g, 35.2 mmol) in portions over 15 min. After stirring for 2 h at room temperature, water (3 mL) was added and the resulting mixture filtered through a short pad of Celite™. The filtrate was concentrated in vacuo and the residue dissolved in methylene chloride (150 mL). The solution was cooled in an ice bath and treated with boron tribromide (3.0 mL, 32 mmol) and the resulting mixture warmed to room temperature and stirred for 2 h. The mixture was diluted with water and the organic layer separated, washed once with saturated aqueous sodium bicarbonate solution, once with water, once with saturated aqueous sodium chloride solution, dried (sodium sulfate), filtered, and concentrated in vacuo. The residue was dissolved in N,N-dimethylformamide (60 mL) and treated with cesium carbonate (3.52 g, 10.1 mmol) and methyl bromoacetate (0.96 mL, 10 mmol) at room temperature for 18 h. The mixture was diluted with water and extracted with ethyl acetate. The organic layer was washed once with water, once with saturated aqueous sodium chloride solution, dried (sodium sulfate), filtered, and concentrated in vacuo. Chromatography (silica gel, 10% ethyl acetate/90% hexanes) of the residue provided 1.25 g (40%) of the title compound as an off-white solid: mp 142–144° C. $^1$H NMR (CDCl$_3$) δ 7.22 (m, 1H), 6.89 (dt, J=8.4, 2.2 Hz, 1H), 6.64 (d, J 7.7 Hz, 1H), 6.56 (d, J=9.5 Hz, 1H), 6.47 (bs, 1H), 6.36 (s, 1H), 5.37 (s, 2H), 4.75 (s, 2H), 3.81 (s, 3H), 2.96 (t, J=7.3 Hz, 2H), 2.90 (t, J=7.7 Hz, 2H), 2.27 (s, 3H), 2.04 (quintet, J=7.3 Hz, 2H); MS ES+ m/e 368 (p+1); IR (CHCl$_3$, cm$^{-1}$) 2955, 1760, 1592.

Anal. Calcd for C$_{22}$H$_{22}$FNO$_3$: C, 71.92; H, 6.04; N, 3.81. Found: C, 71.81; H, 6.02; N, 3.88.

C. Preparation of 2-[[3-(2-amino-1,2-dioxoethyl)-2-methyl-1-(3-fluorobenzyl)-1,6,7,8-tetrahydrocyclopent[g]indol-4-yl]oxy]acetic acid methyl ester.

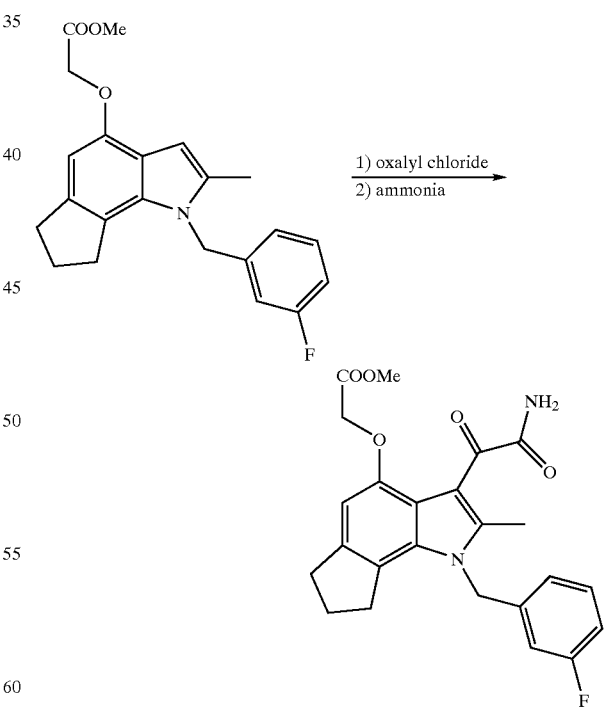

A solution of 2-[(2-methyl-1-(3-fluorobenzyl)-1,6,7,8-tetrahydrocyclopent[g]indol-4-yl)oxy]acetic acid methyl ester (613 mg, 1.67 mmol) in methylene chloride (13 mL) was cooled in an ice bath and treated with oxalyl chloride (0.72 mL, 8.3 mmol). The mixture was allowed to warm to room temperature over 1 h then concentrated in vacuo. The residue was dissolved in methylene chloride and concentrated in vacuo. The residue was dissolved in methylene chloride (10 mL) and treated with an excess of 0.5 M ammonia in dioxane for 1 h at room temperature. The mixture was concentrated in vacuo and the residue slurried in ethyl acetate. The resulting solid was collected via vacuum filtration to provide 0.7 g (96%). Recrystallization (ethyl acetate) provided an analytical sample as green crystals: 245–247° C. $^1$H NMR (DMSO-$d_6$) δ 7.65 (s, 1H), 7.35 (m, 2H), 7.10 (dt, J=8.4, 1.8 Hz, 1H), 6.77 (d, J=9.1 Hz, 1H), 6.70 (d, J=7.7 Hz, 1H), 6.51 (s, 1H), 5.56 (s, 2H), 4.72 (s, 2H), 3.71 (s, 3H), 2.93 (t, J=7.3 Hz, 2H), 2.82 (t, J=7.3 Hz, 2H), 2.41 (s, 3H), 1.97 (quintet, J=7.0 Hz, 2H); MS ES+ m/e 439 (p+1); IR (CHCl$_3$, cm$^{-1}$) 3516, 3402, 1702, 1649.

Anal. Calcd for $C_{24}H_{23}FN_2O_5$: C, 65.74; H, 5.29; N, 6.39. Found: C, 65.54; H, 5.27; N, 6.33.

Example 7

2-[[3-(2-Amino-1,2-dioxoethyl)-2-methyl-1-(3-fluorobenzyl)-1,6,7,8-tetrahydrocyclopent[g]indol-4-yl]oxy]acetic acid hydrate

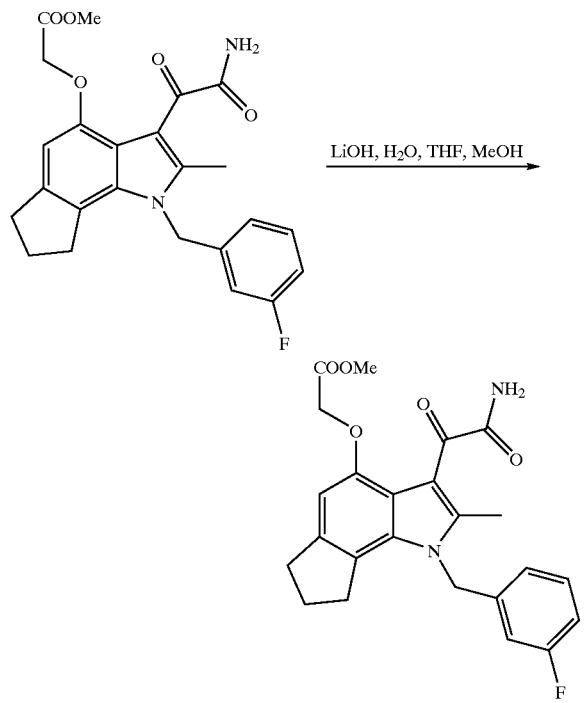

Preparation of 2-[[3-(2-amino-1,2-dioxoethyl)-2-methyl-1-(3-fluorobenzyl)-1,6,7,8-tetrahydrocyclopent[g]indol-4-yl]oxy]acetic acid hydrate. A solution of 2-[[3-(2-amino-1,2-dioxoethyl)-2-methyl-1-(3-fluorobenzyl)-1,6,7,8-tetrahydrocyclopent[g]indol-4-yl]oxy]acetic acid methyl ester (500 mg, 1.14 mmol) in tetrahydrofuran (20 mL) and methanol (20 mL) was treated with 1 M aqueous lithium hydroxide (25 mL) at room temperature for 18 h. The resulting suspension was concentrated in vacuo and the residue diluted with water and adjusted to pH 2 with concentrated hydrochloric acid. After stirring for 1 h, the resulting precipitate was collected via vacuum filtration to provide 390 mg (77%) of the title compound as a solid. Recrystallization (methanol/water) of the residue provided an analytical sample as a yellow-green fibrous solid: mp 250–252° C. $^1$H NMR (DMSO-$d_6$) δ 12.87 (bs, 1H), 7.71 (s, 1H), 7.42 (s, 1H), 7.37 (m, 1H), 7.10 (dt, J=10.6, 2.2 Hz, 1H), 6.77 (d, J=9.9 Hz, 1H), 6.69 (d, J=7.7 Hz, 1H), 6.47 (s, 1H), 5.56 (s, 2H), 4.62 (s, 2H), 2.93 (t, J=7.0 Hz, 2H), 2.82 (t, J=7.0 Hz, 2H), 2.41 (s, 3H), 1.97 (quintet, J=7.3 Hz, 2H); MS ES– m/e 423 (p–1); IR (KBr, cm$^{-1}$) 3438, 1617, 1376.

Anal. Calcd for $C_{23}H_{21}FN_2O_5 \cdot H_2O$: C, 62.44; H, 5.24; N, 6.33. Found: C, 62.36; H, 5.21; N, 6.01.

Example 8

2-[[3-(2-Amino-1,2-dioxoethyl)-2-methyl-1-(2-fluorobenzyl)-1,6,7,8-tetrahydrocyclopent[g]indol-4-yl]oxy]acetic acid methyl ester A. Preparation of 1-(2-fluorobenzyl)-2-hydroxymethyl-4-methoxy-1,6,7,8-tetrahydrocyclopent[g]indole.

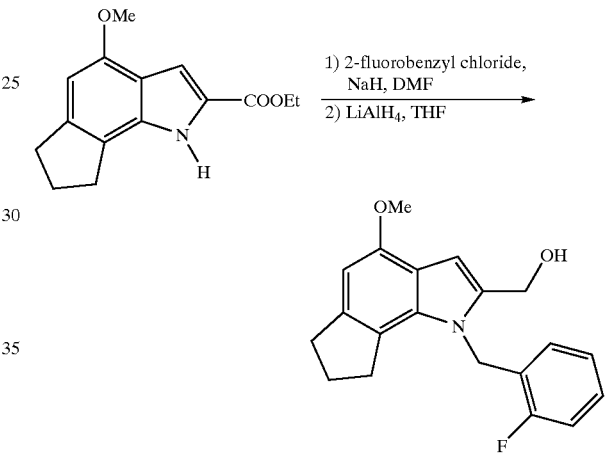

A solution of of 2-carboethoxy-4-methoxy-1,6,7,8-tetrahydrocyclopent[g]indole (3.00 g, 11.6 mmol) in N,N-dimethylformamide (100 mL) was treated with a 60% dispersion of sodium hydride in mineral oil (0.70 g) at room temperature for 15 min. 2-Fluorobenzyl chloride (2.17 g, 15.0 mmol) was added and the resulting mixture stirred for 18 h. The mixture was diluted with water and extracted twice with ethyl acetate. The combined ethyl acetate extracts were washed once with water, once with saturated aqueous sodium chloride solution, dried (sodium sulfate), filtered, and concentrated in vacuo. The residue was dissolved in tetrahydrofuran (70 mL) and treated with lithium aluminum hydride (0.40 g, 10 mmol) at room temperature for 17 h. The mixture was treated with excess sodium sulfate decahydrate, diluted with ether, and filtered. The filtrate was concentrated in vacuo to provide 2.61 g (69%) of the title compound as a light yellow solid. Recrystallization (ethyl acetate/hexanes) provided an analytical sample as white crystals: mp 155–157° C. $^1$H NMR (CDCl$_3$) δ 7.15 (m, 1H), 7.06 (t, J=8.2 Hz, 1H), 6.89 (t, J=7.4 Hz, 1H), 6.63 (s, 1H), 6.47 (s, 1H), 6.30 (t, J=7.7 Hz, 1H), 5.63 (s, 2H), 4.65 (s, 2H), 3.93 (s, 3H), 2.94 (t, J=6.9 Hz, 2H), 2.92 (t, J=7.0 Hz, 2H), 2.06 (quintet, J=7.7 Hz, 2H), 1.47 (bs, 1H); MS ES+ m/e 326 (p+1); IR (CHCl$_3$, cm$^{-1}$) 3580, 2955, 1590, 1490.

Anal. Calcd for $C_{20}H_{20}FNO_2$: C, 73.83; H, 6.20; N, 4.30. Found: C, 74.22; H, 6.21; N, 4.62.

B. Preparation of 2-[(2-methyl-1-(2-fluorobenzyl)-1,6,7,8-tetrahydrocyclopent[g]indol-4-yl)oxy]acetic acid methyl ester.

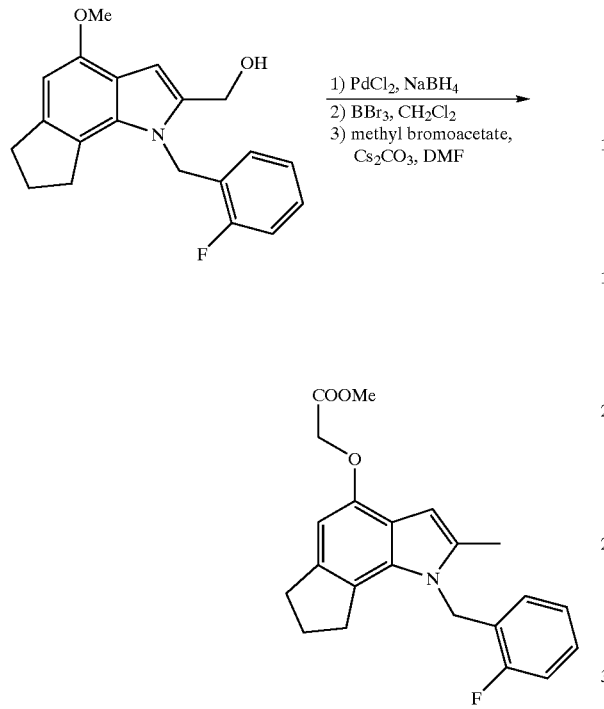

A solution of 1-(2-fluorobenzyl)-2-hydroxymethyl-4-methoxy-1,6,7,8-tetrahydrocyclopent[g]indole (1.80 g, 5.53 mmol) in tetrahydrofuran (193 mL) and methanol (19 mL) was treated with palladium(II) chloride (1.72 g, 9.70 mmol) and sodium borohydride (628 mg, 16.6 mmol) in portions over 20 min. The mixture was stirred for 2 h then filtered through a pad of Celite™. The filtrate was concentrated in vacuo and the residue dissolved in ether, washed once with water, and once with saturated aqueous sodium chloride solution, dried (sodium sulfate), filtered, and concentrated in vacuo. The residue was dissolved in methylene chloride (50 mL), cooled in an ice bath, and treated with boron tribromide (1.2 mL, 13 mmol). The mixture was poured into ice water and extracted with chloroform. The organic layer was washed once with water, once with dilute aqueous sodium bicarbonate solution, once with saturated aqueous sodium chloride solution, dried (sodium sulfate), filtered, and concentrated in vacuo. The residue was dissolved in N,N-dimethylformamide (25 mL) and treated with cesium carbonate (1.72 g, 4.88 mmol) and methyl bromoacetate (0.46 mL, 4.9 mmol) at room temperature for 64 h. The mixture was diluted with water and extracted three times with ethyl acetate. The combined organic layers were washed once with water, once with saturated aqueous sodium chloride solution, dried (sodium sulfate), filtered, and concentrated in vacuo. Chromatography (silica gel, 10% ethyl acetate/90% hexanes) of the residue provided 0.60 g (30%) of the title compound as a white solid: mp 150–152° C. $^1$H NMR (CDCl$_3$) δ 7.18 (t, J=7.3 Hz, 1H), 7.07 (t, J=9.2 Hz, 1H), 6.92 (t, J=7.3 Hz, 1H), 6.50 (bs, 1H), 6.35 (S, 1H), 6.34 (m, 1H), 5.44 (s, 2H), 4.76 (S, 2H), 3.82 (s, 3H), 2.96 (t, J=7.3 Hz, 2H), 2.90 (t, J=7.6 Hz, 2H), 2.29 (s, 3H), 2.04 (quintet, J=7.3 Hz, 2H); MS ES+ m/e 368 (p+1); IR (CHCl$_3$, cm$^{-1}$) 2955, 1760, 1489.

Anal. Calcd for C$_{22}$H$_{22}$FNO$_3$: C, 71.92; H, 6.04; N, 3.81. Found: C, 71.52; H, 5.78; N, 3.67.

B. Preparation of 2-[[3-(2-amino-1,2-dioxoethyl)-2-methyl-1-(2-fluorobenzyl)-1,6,7,8-tetrahydrocyclopent[g]indol-4-yl]oxy]acetic acid methyl ester.

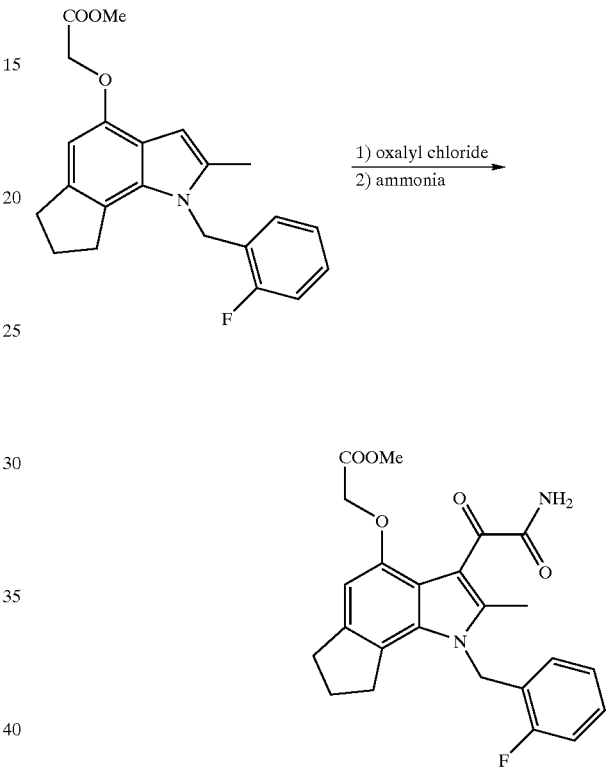

A solution of 2-[(2-methyl-1-(2-fluorobenzyl)-1,6,7,8-tetrahydrocyclopent[g]indol-4-yl)oxy]acetic acid methyl ester (0.53 g, 1.44 mmol) in methylene chloride (10 mL) was cooled in an ice bath and treated with oxalyl chloride (0.63 mL, 7.2 mmol). The mixture was warmed to room temperature over 1.5 h then concentrated in vacuo. The residue was dissolved in methylene chloride and concentrated in vacuo. The residue was dissolved in methylene chloride (10 mL) and treated with 0.5 M ammonia in dioxane (18 mL) for 1 h. The mixture was concentrated in vacuo and slurried in ethyl acetate to provide 0.45 g (71%) of the title compound as a beige solid. Recrystallization (ethyl acetate) provided an analytical sample as pale yellow crystals: mp 228–230° C. (dec). $^1$H NMR (CDCl$_3$) δ 7.26 (m, 1H), 7.11 (t, J=8.8 Hz, 1H), 6.98 (t, J=6.5 Hz, 1H), 6.62 (bs, 1H), 6.48 (m, 2H), 5.55 (bs, 1H), 5.48 (s, 2H), 4.71 (s, 2H), 3.78 (s, 3H), 2.95 (t, J=7.3 Hz, 2H), 2.89 (t, J=7.6 Hz, 2H), 2.46 (s, 3H), 2.04 (quintet, J=7.3 Hz, 2H); MS ES+ m/e 439 (p+1); IR (KBr, cm$^{-1}$) 3389, 1732, 1641.

Anal. Calcd for C$_{24}$H$_{23}$FN$_2$O$_5$: C, 65.74; H, 5.29; N, 6.39. Found: C, 65.76; H, 5.23; N, 6.34.

Example 9

2-[[3-(2-Amino-1,2-dioxoethyl)-2-methyl-1-(2-fluorobenzyl)-1,6,7,8-tetrahydrocyclopent[g]indol-4-yl]oxy]acetic acid

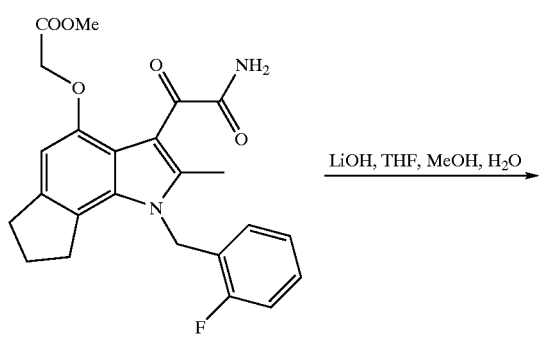

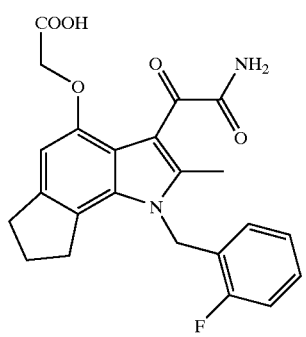

Preparation of 2-[[3-(2-amino-1,2-dioxoethyl)-2-methyl-1-(2-fluorobenzyl)-1,6,7,8-tetrahydrocyclopent[g]indol-4-yl]oxy]acetic acid. A solution of 2-[[3-(2-amino-1,2-dioxoethyl)-2-methyl-1-(2-fluorobenzyl)-1,6,7,8-tetrahydrocyclopent[g]indol-4-yl]oxy]acetic acid methyl ester (345 mg, 0.787 mmol) in tetrahydrofuran (20 mL) and methanol (20 mL) was treated with 1 M aqueous lithium hydroxide solution (25 mL) at room temperature for 19 h. The mixture was diluted with water and methanol and filtered. The filtrate was concentrated in vacuo and the residue dissolved in water and acidified with concentrated hydrochloric acid. The resulting precipitate was collected via vacuum filtration, washed with water, and air-dried to provide 165 mg (50%) of the title compound as a yellow solid. Recrystallization (methanol/water) provided an analytical sample as a yellow green solid: mp 246–249° C. (dec). $^1$H NMR (DMSO-$d_6$) δ 12.94 (bs, 1H), 7.73 (bs, 1H), 7.44 (bs, 1H), 7.33 (m, 2H), 7.11 (t, J=7.6 Hz, 1H), 6.48 (s, 1H), 6.37 (t, J=7.6 Hz, 1H), 5.59 (s, 2H), 4.63 (s, 2H), 2.92 (t, J=7.3 Hz, 2H), 2.83 (t, J=7.3 Hz, 2H), 2.44 (s, 3H), 1.97 (quintet, J=7.3 Hz, 2H); MS ES+ m/e 425 (p+1); IR (KBr, cm$^{-1}$) 3450, 1619, 1225.

Anal. Calcd for $C_{23}H_{21}FN_2O_5$: C, 65.09; H, 4.99; N, 6.60. Found: C, 65.11; H, 4.78; N, 6.20.

Example 10

2-[[3-(2-Amino-1,2-dioxoethyl)-2-methyl-1-(4-fluorobenzyl)-1,6,7,8-tetrahydrocyclopent[g]indol-4-yl]oxy]acetic acid methyl ester

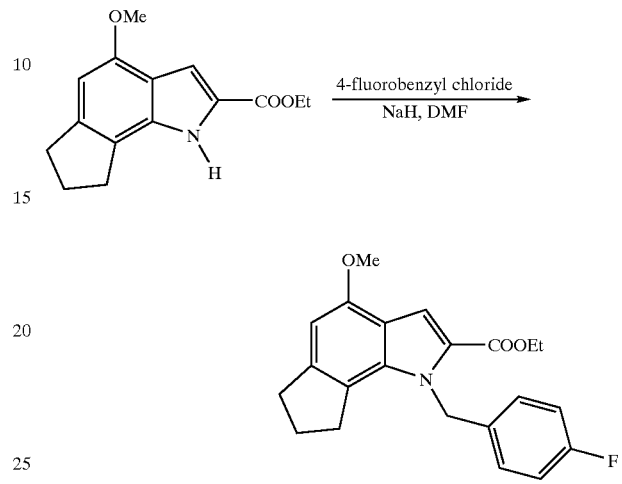

A. Preparation of 1-(4-fluorobenzyl)-2-carboethoxy-4-methoxy-1,6,7,8-tetrahydrocyclopent[g]indole. 2-Carboethoxy-4-methoxy-1,6,7,8-tetrahydrocyclopent[g]indole (4.00 g, 15.4 mmol) was added to a hexane-washed suspension of a 60% dispersion of sodium hydride in mineral oil (0.88 g). The resulting mixture was stirred at room temperature for 30 min then treated with 4-fluorobenzyl chloride (2.89 g, 20.0 mmol). After stirring for 42 h, the mixture was diluted with water and extracted four times with ethyl acetate. The combined organic layers were washed once with water, once with saturated aqueous sodium chloride solution, dried (sodium sulfate), filtered, and concentrated in vacuo. Chromatography (silica gel, 5% ethyl acetate/95% hexanes) of the residue provided 4.2 g (74%) of the title compound as a white solid: mp 83–88° C. $^1$H NMR (CDCl$_3$) δ 7.50 (s, 1H), 6.80–6.95 (m, 4H), 6.47 (s, 1H), 5.92 (bs, 2H), 4.25 (q, J=7.3 Hz, 2H), 3.94 (s, 3H), 3.04 (t, J=7.3 Hz, 2H), 2.95 (t, J=7.3 Hz, 2H), 2.08 (quintet, J=7.3 Hz, 2H), 1.32 (t, J=7.3 Hz, 3H); MS ES+ m/e 368 (p+1); IR (CHCl$_3$, cm$^{-1}$) 1701, 1512, 1496.

Anal. Calcd for $C_{22}H_{22}FNO_3$: C, 71.92; H, 6.04; N, 3.81. Found: C, 72.18; H, 5.90; N, 3.84.

B. Preparation of 1-(4-fluorobenzyl)-2-hydroxymethyl-4-methoxy-1,6,7,8-tetrahydrocyclopent[g]indole.

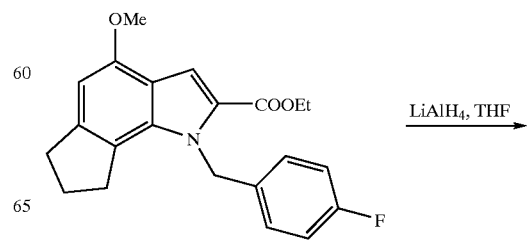

-continued

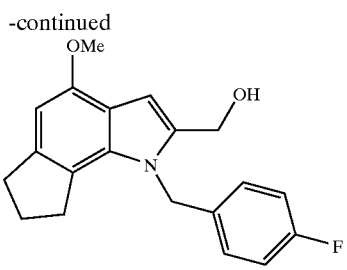

A solution of 1-(4-fluorobenzyl)-2-carboethoxy-4-methoxy-1,6,7,8-tetrahydrocyclopent[g]indole (4.00 g, 10.9 mmol) in tetrahydrofuran (120 mL) was treated with lithium aluminum hydride (0.455 g, 12.0 mmol) at room temperature for 20 h. Excess sodium sulfate decahydrate was added and the resulting mixture stirred and then dried with anhydrous sodium sulfate. The mixture was filtered and concentrated in vacuo to provide 3.0 g (85%) of the title compound as a solid. Recrystallization (ethyl acetate/hexanes) provided an analytical sample as white crystals: mp 160–162° C. $^1$H NMR (CDCl$_3$) δ 6.92 (t, J=8.7 Hz, 2H), 6.83 (m, 2H), 6.61 (s, 1H), 6.47 (s, 1H), 5.56 (s, 2H), 4.61 (s, 2H), 3.93 (s, 3H), 2.97 (t, J=7.4 Hz, 2H), 2.93 (t, J=7.3 Hz, 2H), 2.06 (quintet, J=7.3 Hz, 2H), 1.48 (bs, 1H);

MS ES+ m/e 326 (p+1); IR (CHCl$_3$, cm$^{-1}$) 2954, 1608, 1511.

Anal. Calcd for C$_{20}$H$_{20}$FNO$_2$: C, 73.83; H, 6.20; N, 4.30. Found: C, 74.15; H, 5.95; N, 4.25.

B. Preparation of 1-(4-fluorobenzyl)-2-methyl-4-methoxy-1,6,7,8-tetrahydrocyclopent[g]indole.

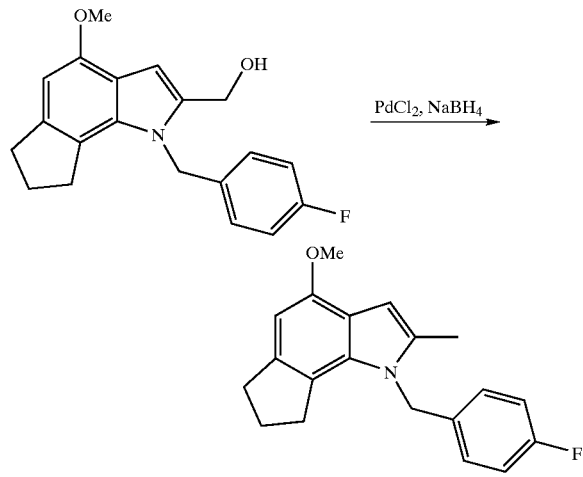

A solution of 1-(4-fluorobenzyl)-2-hydroxymethyl-4-methoxy-1,6,7,8-tetrahydrocyclopent[g]indole (2.80 g, 8.61 mmol) in tetrahydrofuran (280 mL) and methanol (28 mL) was treated with palladium(II) chloride (2.67 g, 15.1 mmol) and sodium borohydride (0.977 g, 25.8 mmol) in portions over 15 min. The mixture was stirred at room temperature for 1.5 h, diluted with water (3 mL), and filtered through a short pad of Celite™. The filtrate was concentrated in vacuo to provide a quantitative yield of the title compound. Chromatography (silica gel, 10% ethyl acetate/90% hexanes) provided an analytical sample as a white solid: 152–154° C.

$^1$H NMR (CDCl$_3$) δ 6.93 (m, 2H), 6.83 (m, 2H), 6.46 (s, 1H), 6.40 (bs, 1H), 5.37 (s, 2H), 3.93 (s, 3H), 2.98 (t, J=7.3 Hz, 2H), 2.93 (t, J=7.3 Hz, 2H), 2.27 (s, 3H), 2.08 (quintet, J=7.7 Hz, 2H); MS ES+ m/e 310 (p+1); IR (CHCl$_3$, cm$^{-1}$) 2900, 1508, 1246.

Anal. Calcd for C$_{20}$H$_{20}$FNO: C, 77.64; H, 6.51; N, 4.53. Found: C, 77.92; H, 6.60; N, 4.52.

C. Preparation of 2-[(2-methyl-1-(4-fluorobenzyl)-1,6,7,8-tetrahydrocyclopent[g]indol-4-yl)oxy]acetic acid methyl ester.

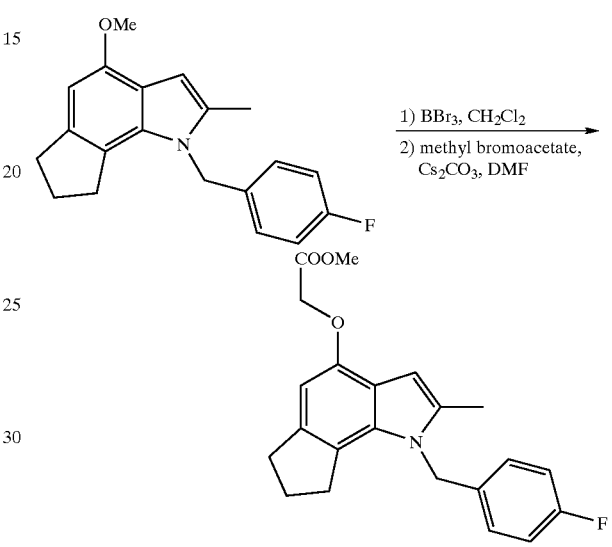

A solution of 1-(4-fluorobenzyl)-2-methyl-4-methoxy-1,6,7,8-tetrahydrocyclopent[g]indole (2.60 g, 8.40 mmol) in methylene chloride (120 mL) was cooled in an ice bath and treated with boron tribromide (12.4 mL, 25 mmol). The mixture was allowed to warm to room temperature over 1.5 h, poured into water (500 mL), and extracted three times with methylene chloride. The combined organic layers were washed once with dilute aqueous sodium bicarbonate solution, once with water, and once with saturated aqueous sodium chloride solution, dried (sodium sulfate), filtered, and concentrated in vacuo. The residue was dissolved in N,N-dimethylformamide (30 mL) and treated with cesium carbonate (1.92 g, 5.44 mmol) and methyl bromoaceate (0.52 mL, 5.5 mmol) at room temperature for 16 h. The mixture was diluted with water and extracted three times with ethyl acetate. The combined organic layers were washed once with water, once with saturated aqueous sodium chloride solution, dried (sodium sulfate), filtered and concentrated in vacuo. Chromatography (silica gel, 10% ethyl acetate/90% hexanes) of the residue provided 0.71 g (43%) of the title compound as a white solid: mp 134–136° C. $^1$H NMR (CDCl$_3$) δ 6.94 (m, 2H), 6.83 (m, 2H), 6.44 (bs, 1H), 6.36 (s, 1H), 5.37 (s, 2H), 4.76 (s, 2H), 3.81 (s, 3H), 2.97 (t, J=7.3 Hz, 2H), 2.90 (t, J=7.3 Hz, 2H), 2.28 (s, 3H), 2.05 (quintet, J=7.3 Hz, 2H); MS ES+ m/e 368 (p+1); IR (CHCl$_3$, cm$^{-1}$) 2955, 1760, 1510.

Anal. Calcd for C$_{22}$H$_{22}$FNO$_3$: C, 71.92; H, 6.04; N, 3.81. Found: C, 72.25; H, 5.92; N, 3.89.

D. Preparation of 2-[[3-(2-amino-1,2-dioxoethyl)-2-methyl-1-(4-fluorobenzyl)-1,6,7,8-tetrahydrocyclopent[g]indol-4-yl]oxy]acetic acid methyl ester.

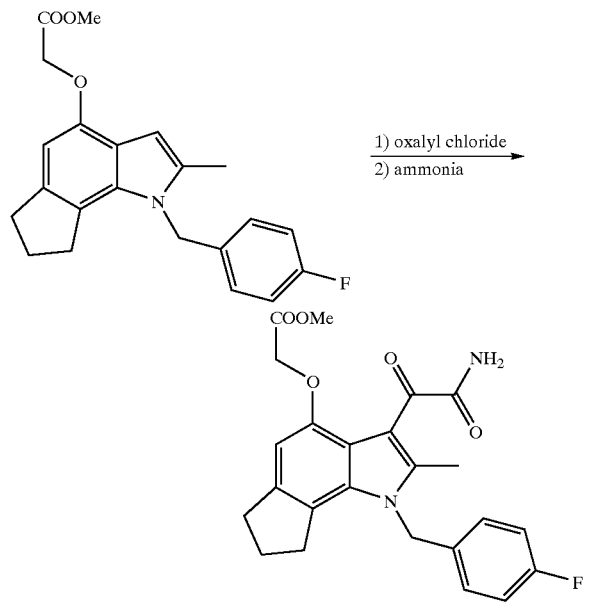

A solution of 2-[(2-methyl-1-(4-fluorobenzyl)-1,6,7,8-tetrahydrocyclopent[g]indol-4-yl)oxy]acetic acid methyl ester (0.56 g, 1.52 mmol) in methylene chloride (13 mL) was cooled in an ice bath and treated with oxalyl chloride (0.66 mL, 7.6 mmol). The mixture was warmed to room temperature over 1.5 h then concentrated in vacuo. The residue was dissolved in methylene chloride and concentrated in vacuo. The residue was dissolved in methylene chloride (13 mL) and treated with 0.5 M ammonia in dioxane (20 mL) for 1 h. The mixture was concentrated in vacuo and slurried in ethyl acetate. The resulting precipitate was collected and recrystallized (ethyl acetate) to provide 0.20 g (30%) of the title compound as yellow crystals: mp 222–224° C. $^1$H NMR (CDCl$_3$) δ 6.99 (m, 2H), 6.92 (m, 2H), 6.60 (bs, 1H), 6.48 (s, 1H), 5.47 (bs, 1H), 5.42 (s, 2H), 4.71 (s, 2H), 3.78 (s, 3H), 2.97 (t, J=7.3 Hz, 2H), 2.90 (t, J=7.6 Hz, 2H), 2.45 (s, 3H), 2.05 (quintet, J=7.3 Hz, 2H); MS ES+ m/e 439 (p+1); IR (CHCl$_3$, cm$^{-1}$) 1760, 1701, 1646.

Anal. Calcd for C$_{24}$H$_{23}$FN$_2$O$_5$: C, 65.74; H, 5.29; N, 6.39. Found: C, 65.31; H, 5.18; N, 6.35.

Example 11

2-[[3-(2-Amino-1,2-dioxoethyl)-2-methyl-1-(4-fluorobenzyl)-1,6,7,8-tetrahydrocyclopent[g]indol-4-yl]oxy]acetic acid

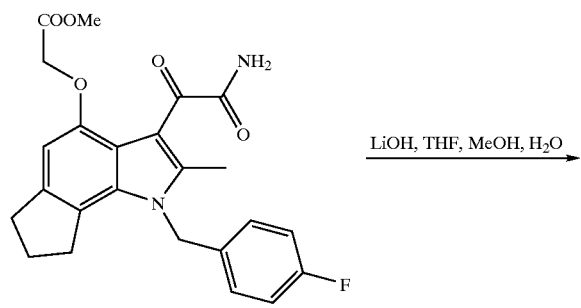

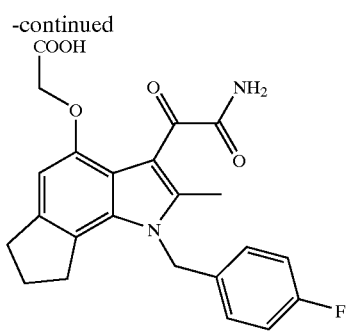

Preparation of 2-[[3-(2-amino-1,2-dioxoethyl)-2-methyl-1-(4-fluorobenzyl)-1,6,7,8-tetrahydrocyclopent[g]indol-4-yl]oxy]acetic acid. A solution of 2-[[3-(2-amino-1,2-dioxoethyl)-2-methyl-1-(4-fluorobenzyl)-1,6,7,8-tetrahydrocyclopent[g]indol-4-yl]oxy]acetic acid methyl ester (0.34 g, 0.78 mmol) in tetrahydrofuran (15 mL) and methanol (15 mL) was treated with 1 M aqueous lithium hydroxide solution (20 mL) at room temperature for 66 h. The mixture was concentrated in vacuo and the residue acidified with concentrated hydrochloric acid. The resulting precipitate was collected via vacuum filtration, washed with water, and air-dried to provide 168 mg (51%) of the title compound as a green solid: mp 199–201° C. (dec). $^1$H NMR (DMSO-d$_6$) δ 13.10 (bs, 1H), 7.18 (m, 2H), 6.95 (m, 2H), 6.50 (s, 1H), 5.55 (s, 2H), 4.62 (s, 2H), 2.95 (t, J=6.6 Hz, 2H), 2.83 (t, J=7.0 Hz, 2H), 2.50 (s, 3H), 1.98 (quintet, J=7.3 Hz, 2H).

TOS MS ES$^+$ exact mass calculated for C$_{23}$H$_{22}$FN$_2$O$_5$ (p+1): m/z=425.1513. Found: 425.1532.

Example 12

2-[[3-(2-Amino-1,2-dioxoethyl)-1-benzyl-2-ethyl-6,7,8,9-tetrahydro-1H-benz[g]indol-4-yl]oxy]acetic acid methyl ester.

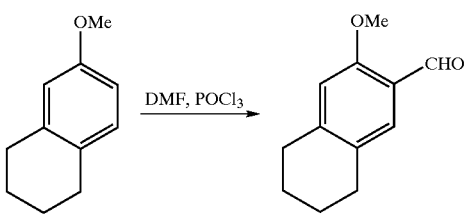

A. Preparation of 3-methoxy-5,6,7,8-tetrahydronaphthalene-2-carbaldehyde. To N,N-dimethylformamide (74.7 mL, 0.966 mol) cooled to 0° C. was added phosphorus oxychloride (82.8 mL, 0.882 mol). After stirring for 30 min, 3-methoxy-5,6,7,8-tetrahydronaphthalene (68.0 g, 0.420 mol) was added and the resulting mixture heated at 80° C. for 4 h. The mixture was cooled to room temperature, poured over crushed ice, and extracted four times with ether. The combined extracts were dried (sodium sulfate), filtered, and concentrated in vacuo to provide a dark oil. Crystallization (hexane with a trace of absolute ethanol) provided 42.5 g (53%) of the title compound as yellow needles: mp 51–53° C.

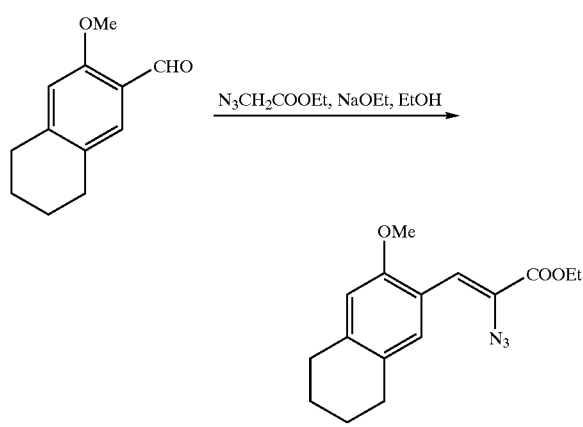

B. Preparation of 3-(3-Methoxy-5,6,7,8-tetrahydronaphthalen-2-yl)-2-azido-2-propenoic acid ethyl ester.

Sodium (19.0 g, 0.827 mol) was dissolved in absolute ethanol (600 mL). After cooling to −10° C., a mixture 3-methoxy-5,6,7,8-tetrahydronaphthalene-2-carbaldehyde (42.5 g, 0.223 mol) and ethyl azidoacetate (97.1 g, 0.752 mol) in 1:1 diethyl ether/absolute ethanol (200 mL) was added dropwise in such a manner that the temperature did not rise above −10° C. The resulting mixture was stirred for 2 h then allowed to warm to 10° C. The volume of the reaction mixture was reduced in vacuo to approximately 200 mL, then poured into ice water. The resulting precipitate was collected via vacuum filtration and washed with water to provide 35.0 g (52%) of the title compound as a yellow solid: mp 120–125° C. $^1$H NMR (CDCl$_3$) δ 7.88 (s, 1H), 7.36 (s, 1H), 6.57 (s, 1H), 4.36 (q, J=7.3 Hz, 2H), 3.82 (s, 3H), 2.75 (m, 4H), 1.80 (m, 4H), 1.39 (t, J=7.0 Hz, 3H); MS FD+ m/e 301 (p); IR (CHCl$_3$, cm$^{-1}$) 2934, 2119, 1704.

B. Preparation of 2-carboethoxy-4-methoxy-6,7,8,9-tetrahydro-1H-benz[g]indole

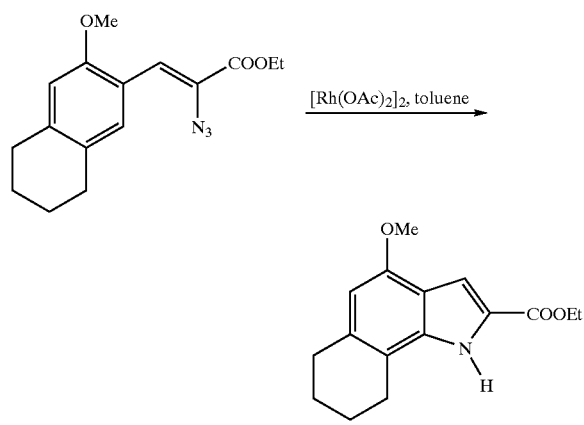

A solution of 3-(3-methoxy-5,6,7,8-tetrahydronaphthalen-2-yl)-2-azido-2-propenoic acid ethyl ester (34.2 g, 0.113 mmol) in toluene (200 mL) was treated with rhodium(II) acetate dimer (300 mg, 0.679 mmol) at 95° C. for 4 h then at reflux for 1 h. The mixture was cooled to room temperature and the resulting solids were collected via vacuum filtration. The filtrate was concentrated to give a further precipitate that was collected via vacuum filtration. The filtrate was filtered through a silica gel plug and concentrated to provide an additional portion of product to give a total of 25.8 g (83%) of the title compound: mp 202–203° C. $^1$H NMR (CDCl$_3$) δ 8.65 (bs, 1H, —NH), 7.30 (d, J=2.2 Hz, 1H), 6.24 (s, 1H), 4.38 (q, J=7.0 Hz, 2H), 3.91 (s, 3H), 2.84 (t, J=5.9 Hz, 2H), 2.76 (t, J=5.5 Hz, 2H), 1.90 (m, 4H), 1.40 (t, J=7.0 Hz, 3H); MS ES+ m/e 274 (p+1); IR (CHCl$_3$, cm$^{-1}$) 3459, 2937, 1698.

Anal. Calcd for C$_{16}$H$_{19}$NO$_3$: C, 70.31; H, 7.01; N, 5.12. Found: C, 70.33; H, 6.93; N, 4.98.

C. Preparation of 1-benzyl-2-carboethoxy-4-methoxy-6,7,8,9-tetrahydro-1H-benz[g]indole

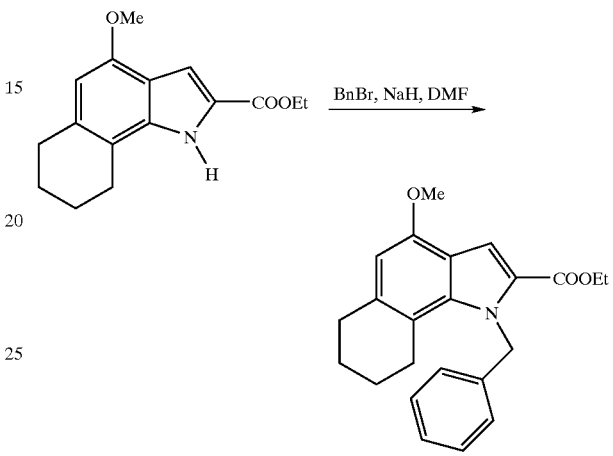

A suspension of 60% sodium hydride in mineral oil (4.08 g, 0.102 mol) was washed once with hexane and suspended in dry N,N-dimethylformamide (100 mL). 2-Carboethoxy-4-methoxy-6,7,8,9-tetrahydro-1H-benz[g]indole (25.4 g, 92.7 mmol) was added in several portions resulting in gas evolution. Benzyl bromide (12.1 mL, 102 mmol) was added in two portions over 30 min and the resulting mixture stirred for 18 h. Additional portions of 60% sodium hydride suspension (1.30 g) and benzyl bromide (2 mL) were added and the mixture stirred for 27 h. The mixture was poured into water (2 L) and the resulting solution extracted three times with ethyl acetate. The combined extracts were Washed three times with water, dried (sodium sulfate), filtered, and concentrated in vacuo. Chromatography (silica gel) provided 12.6 g (37%) of the title compound as a yellow solid: mp 86–88° C. $^1$H NMR (CDCl$_3$) δ 7.51 (s, 1H), 7.20 (m, 3H), 6.84 (d, J=6.6 Hz, 2H), 6.24 (s, 1H), 6.12 (s, 2H), 4.23 (q, J=7.0 Hz, 2H), 3.93 (s, 3H), 2.96 (m, 2H), 2.85 (m, 2H), 1.71 (m, 4H), 1.30 (t, J=7.0 Hz, 3H); MS ES+ m/e 364 (p+1); IR (CHCl$_3$, cm$^{-1}$) 2937, 1701, 1502.

Anal. Calcd for C$_{23}$H$_{25}$NO$_3$: C, 76.01; H, 6.93; N, 3.85. Found: C, 76.02; H, 7.03; N, 4.13.

D. Preparation of 2-acetyl-1-benzyl-4-methoxy-6,7,8,9-tetrahydro-1H-benz[g]indole

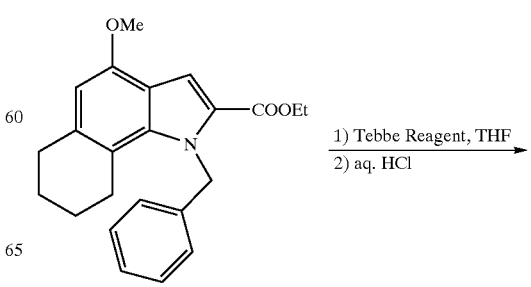

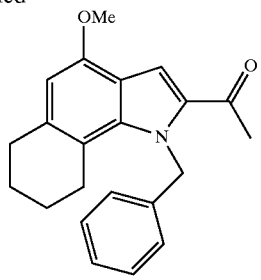

To a solution of 1-benzyl-2-carboethoxy-4-methoxy-6,7,8,9-tetrahydro-1H-benz[g]indole (1.01 g, 2.77 mmol) in tetrahydrofuran (8 mL) cooled to 0° C. was added 0.5 M Tebbe Reagent in toluene (6.5 mL, 3.3 mmol). The mixture was stirred for 1 h at 2° C. then diluted with diethyl ether (32 mL) and treated with 2 N aqueous sodium hydroxide solution (2 mL) over 30 min. The mixture was diluted with excess saturated sodium bicarbonate solution and filtered through a pad of silica gel. The filtrate was concentrated in vacuo and the resulting residue triturated with 1:1 ether/hexanes. The resulting material was dissolved in 4:1 acetone/methylene chloride (5 mL) and treated with 1 N hydrochloric acid (1 mL). After standing for 20 min the mixture was diluted with saturated sodium bicarbonate solution, concentrated in vacuo, and partitioned between methylene chloride and water. The organic layer was separated, dried (sodium sulfate), filtered, and concentrated in vacuo. Purification of the residue by chromatography (silica gel, methylene chloride) provided 673 mg (73%) of the title compound as a brown film. $^1$H NMR (CDCl$_3$) δ 7.49 (s, 1H), 7.15 (m, 3H), 6.78 (d, J=7 Hz, 2H), 6.24 (s, 1H), 6.11 (bs, 2H), 3.91 (s, 3H), 2.95 (m, 2H), 2.84 (m, 2H), 2.52 (s, 2H), 1.69 (m, 4H); MS ES+ m/e 334 (p+1); IR (KBr, cm$^{-1}$) 3400, 2813, 1593, 1292.

Anal. Calcd for C$_{22}$H$_{23}$NO$_2$: C, 79.25; H, 6.95; N, 4.20. Found: C, 79.09; H, 6.65; N, 3.51.

E. Preparation of 1-benzyl-2-(1-hydroxyethyl)-4-methoxy-6,7,8,9-tetrahydro-1H-benz[g]indole

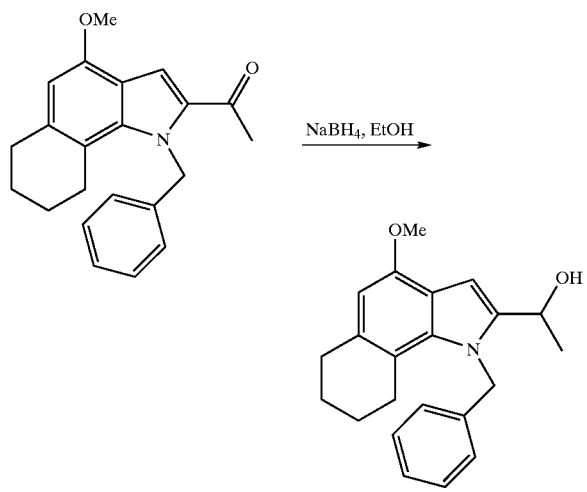

To a solution of 2-acetyl-1-benzyl-4-methoxy-6,7,8,9-tetrahydro-1H-benz[g]indole (4.68 g, 14.0 mmol) in ethanol (50 mL) was added sodium borohydride (537 mg, 14.0 mmol). After stirring for 2 h, 10% aqueous citric acid (10 mL) was added and the mixture concentrated in vacuo. The residue was dissolved in ethyl acetate, washed once with water, and once with saturated sodium bicarbonate solution. The organic layer was dried (magnesium sulfate), filtered and concentrated in vacuo to provide the title compound in quantitative yield. $^1$H NMR (CDCl$_3$) δ 7.20 (m, 3H), 6.79 (d, J=7.0 Hz, 2H), 6.65 (s, 1H), 6.24 (s, 1H), 5.76 (s, 2H), 4.75 (quintet, J=6.6 Hz, 1H), 3.91 (s, 3H), 2.97 (m, 1H), 2.84 (m, 3H), 1.70 (m, 4H), 1.60 (d, J=6.6 Hz, 3H); MS ES+ m/e 336 (p+1).

F. Preparation of 1-benzyl-2-ethyl-4-methoxy-6,7,8,9-tetrahydro-1H-benz[g]indole

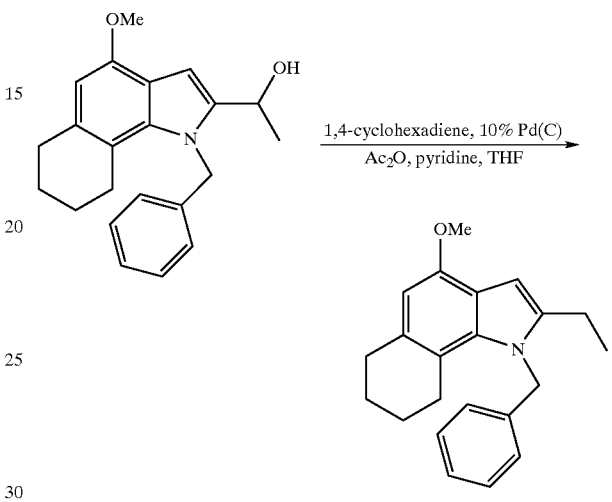

A solution of 1-benzyl-2-(1-hydroxyethyl)-4-methoxy-6,7,8,9-tetrahydro-1H-benz[g]indole (1.0 g, 3.0 mmol) in tetrahydrofuran (5 mL) was treated with acetic anhydride (0.28 mL, 3.0 mmol), pyridine (0.53 mL, 6.6 mmol), 1,4-cyclohexadiene (3 mL), and 10% palladium-on-carbon (0.5 g) at 70° C. for 7 h. The mixture was cooled to room temperature, stirred for 18 h, heated at 80° C. for 9 h, cooled to room temperature, and stirred for 18 h. Additional portions of 10% palladium-on-carbon (0.5 g) and 1,4-cyclohexadiene (3 mL) were added and the resulting mixture stirred at 80° C. for 9 h. The mixture was cooled to room temperature, filtered, and concentrated in vacuo. The residue was dissolved in 9:1 hexanes/ether and treated with 10% aqueous citric acid (3 mL). The organic layer was filtered through silica gel, which was eluted with hexanes, methylene chloride, and ether. Concentration of the appropriate fractions provided 662 mg (70%) of the title compound as an amber foam. $^1$H NMR (CDCl$_3$) δ 7.22 (m, 3H), 6.83 (d, J=7 Hz, 2H), 6.42 (s, 1H), 6.25 (s, 1H), 5.54 (s, 2H), 3.95 (s, 3H), 2.96 (m, 2H), 2.85 (m, 2H), 2.55 (q, J=6 Hz, 2H), 1.70 (m, 4H), 1.28 (t, J=6 Hz, 3H); MS ES+ m/e 320 (p+1).

G. Preparation of 2-[(1-benzyl-2-ethyl-6,7,8,9-tetrahydro-1H-benz[g]indol-4-yl)oxy]acetic acid methyl ester

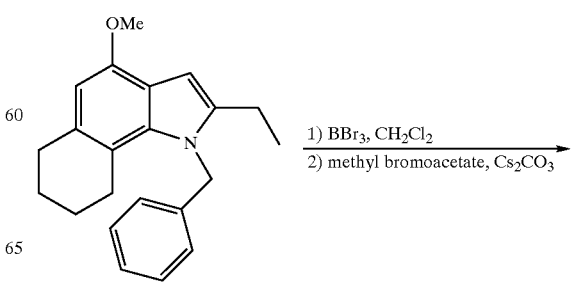

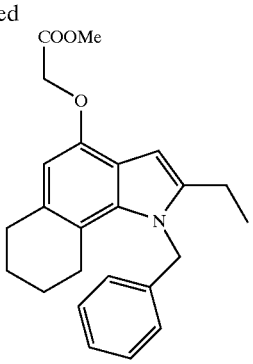

A solution of 1-benzyl-2-ethyl-4-methoxy-6,7,8,9-tetrahydro-1H-benz[g]indole (660 mg, 2.07 mmol) in methylene chloride (10 mL) was cooled to 0° C. and treated with boron tribromide (0.38 mL, 4.0 mmol). The mixture was stirred for 10 min, poured into ice water, and extracted twice with methylene chloride. The combined methylene chloride layers were washed once with saturated sodium bicarbonate solution, dried (sodium sulfate), filtered, and concentrated in vacuo. The residue was dissolved in N,N-dimethylformamide (10 mL) and treated with cesium carbonate (652 mg, 2.00 mmol) and methyl bromoacetate (0.28 mL, 2.0 mmol) at room temperature for 3 h. The mixture was diluted with water and extracted three times with ether. The combined ether extracts were washed once with water, dried (magnesium sulfate), filtered, and concentrated in vacuo. Chromatography (silica gel, methylene chloride) provided 479 mg (62%) of the title compound as an off-white solid. $^1$H NMR (CDCl$_3$) δ 7.25 (m, 3H), 6.85 (d, J=7.6 Hz, 2H), 6.52 (s, 1H), 6.16 (s, 1H), 5.57 (s, 2H), 4.79 (s, 2H), 3.86 (s, 3H), 2.97 (m, 2H), 2.84 (m, 2H), 2.59 (q, J=7.3 Hz, 2H), 1.72 (m, 4H), 1.32 (t, J=7.3 Hz, 3H); MS ES+ m/e 378 (p+1); IR (CHCl$_3$, cm$^1$) 2830, 1756, 1732.

Anal. Calcd for C$_{24}$H$_{27}$NO$_3$: C, 76.36; H, 7.21; N, 3.71. Found: C, 75.06; H, 6.96; N, 3.71.

H. Preparation of 2-[[3-(2-amino-1,2-dioxoethyl)-1-benzyl-2-ethyl-6,7,8,9-tetrahydro-1H-benz[g]indol-4-yl]oxy]acetic acid methyl ester.

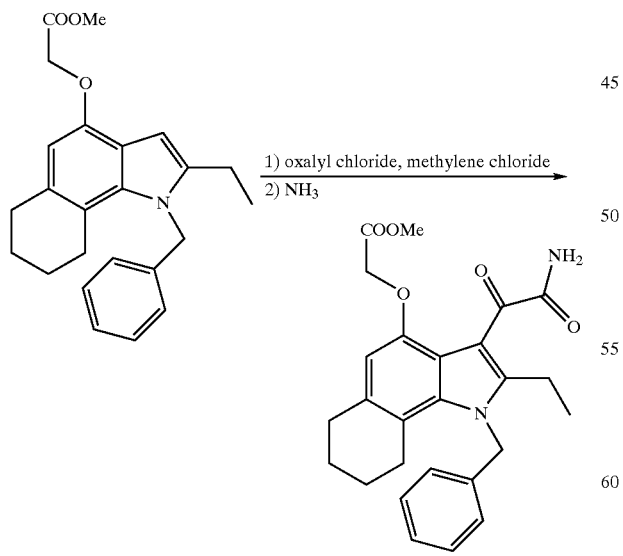

To a solution of 2-[(1-benzyl-2-ethyl-6,7,8,9-tetrahydro-1H-benz[g]indol-4-yl)oxy]acetic acid methyl ester (441 mg, 1.17 mmol) in methylene chloride (10 mL) cooled to 0° C. was added oxalyl chloride (0.57 mL, 5.8 mmol). The mixture was stirred for 45 min, concentrated in vacuo, diluted with fresh methylene chloride, and concentrated in vacuo. The residue was dissolved in methylene chloride and treated with excess 0.5 M ammonia in dioxane. After 15 min the mixture was concentrated in vacuo, diluted with water, ethyl acetate, and hexanes. The resulting suspension was filtered and the filtrate washed twice with water and concentrated in vacuo. Chromatography (silica gel, methylene chloride/acetone) of the residue provided 485 mg (93%) of the title compound as a brown foam. $^1$H NMR (CDCl$_3$) δ 7.25 (m, 3H), 6.91 (d, J=7.0 Hz, 2H), 6.58 (bs, 1H), 6.25 (s, 1H), 5.59 (s, 2H), 5.44 (bs, 1H), 4.69 (s, 2H), 3.78 (s, 3H), 2.90 (m, 2H), 2.80 (m, 4H), 1.66 (m, 4H), 1.17 (t, J=7.3 Hz, 3H); MS ES+ m/e 449 (p+1); IR (CHCl$_3$, cm$^{-1}$) 3516, 3402, 2937, 1703, 1648.

Example 13

2-[[3-(2-Amino-1,2-dioxoethyl)-1-benzyl-2-ethyl-6,7,8,9-tetrahydro-1H-benz[g]indol-4-yl]oxy]acetic acid

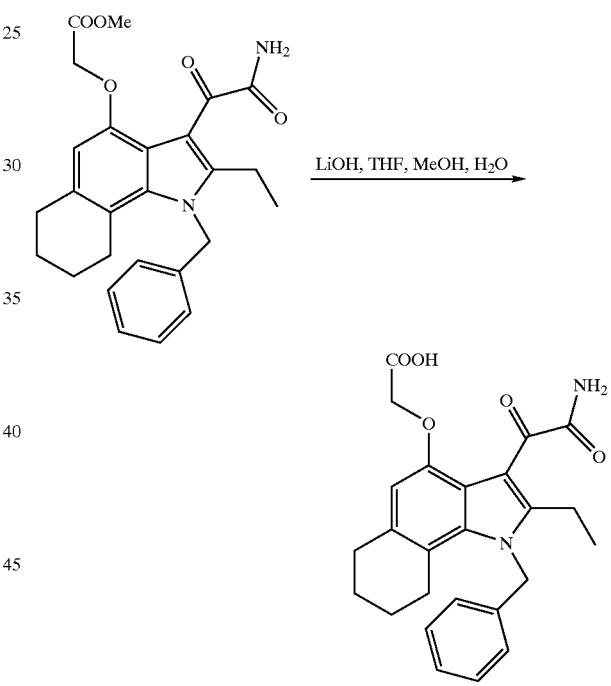

Preparation of 2-[[3-(2-amino-1,2-dioxoethyl)-1-benzyl-2-ethyl-6,7,8,9-tetrahydro-1H-benz[g]indol-4-yl]oxy]acetic acid. A solution of 2-[[3-(2-amino-1,2-dioxoethyl)-1-benzyl-2-ethyl-6,7,8,9-tetrahydro-1H-benz[g]indol-4-yl]oxy]acetic acid methyl ester (150 mg, 0.334 mmol) in 3:1 tetrahydrofuran/methanol (4 mL) was treated with 1 M lithium hydroxide solution (1 mL) at room temperature for 1 h. The reaction mixture was concentrated in vacuo to one half the original volume and treated with 1 M hydrochloric acid (1 mL). The resulting suspension was diluted with water (5 mL), stirred, and the precipitate collected via vacuum filtration. This material was washed with water and dried to provide 128 mg (88%) of the title compound as a yellow solid: mp 222–225° C. $^1$H NMR (DMSO-d$_6$) δ 7.72 (bs, 1H), 7.33 (m, 0.4H), 6.87 (d, J=7.3 Hz, 2H), 6.23 (s, 1H), 5.65 (s, 2H), 4.56 (s, 2H), 2.87 (m, 2H), 2.72 (m, 4H), 1.59 (m, 4H), 1.07 (t, J=7.3 Hz, 3H); MS ES+ m/e 435 (p+1); IR (CHCl₃, cm⁻¹) 3507, 3472, 3393, 2938, 1759, 1640.

Anal. Calcd for $C_{25}H_{26}N_2O_5$: C, 69.11; H, 6.03; N, 6.45. Found: C, 68.80; H, 5.72; N, 6.13.

Example 14

2-[[3-(2-Amino-1,2-dioxoethyl)-1-benzyl-2-methyl-6,7,8,9-tetrahydro-1H-benz[g]indol-4-yl]oxy]acetic acid methyl ester

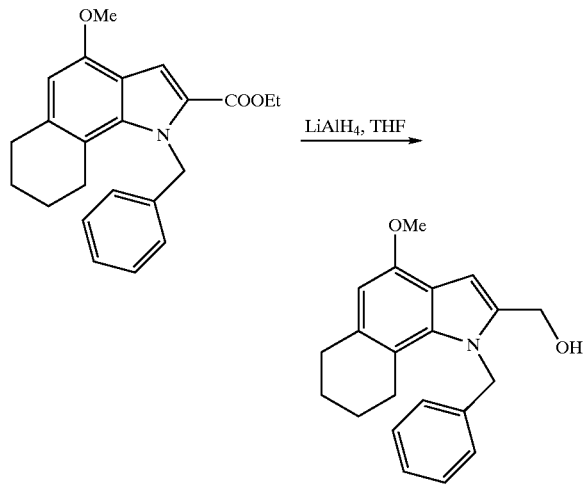

A. Preparation of 1-benzyl-2-hydroxymethyl-4-methoxy-6,7,8,9-tetrahydro-1H-benz[g]indole. A solution of 1-benzyl-2-carboethoxy-4-methoxy-6,7,8,9-tetrahydro-1H-benz[g]indole (4.8 g, 13 mmol) in tetrahydrofuran (40 mL) was treated at room temperature with 1.0 M lithium aluminum hydride in tetrahydrofuran (13 mL, 13 mmol) and stirred for 2 h. The mixture was treated with 5 N sodium hydroxide solution (2.5 mL) and diluted with ether (50 mL). After stirring for 15 min, the resulting granular precipitate was removed by filtration. The filtrate was concentrated in vacuo and recrystallization (methylene chloride/hexanes) of the residue provided 4.01 g (95%) of the title compound as a white solid: mp 115–125° C. ¹H NMR (CDCl₃) δ 7.25–7.35 (m, 3H), 6.85 (d, J=7.6 Hz, 2H), 6.65 (s, 1H), 6.29 (s, 1H), 5.77 (s, 2H), 4.63 (d, J=5.8 Hz, 2H), 3.95 (s, 3H), 2.97 (m, 2H), 2.88 (m, 2H), 1.74 (m, 4H), 1.42 (t, J=6.1 Hz, 1H); MS ES+ m/e 322 (p+1); IR (KBr, cm⁻¹) 3400, 2919, 1241.

Anal. Calcd for $C_{21}H_{23}NO_2 \cdot 0.5H_2O$: C, 76.33; H, 7.32; N, 4.24. Found: C, 76.05; H, 7.27; N, 4.08.

B. Preparation of 1-benzyl-2-methyl-4-methoxy-6,7,8,9-tetrahydro-1H-benz[g]indole.

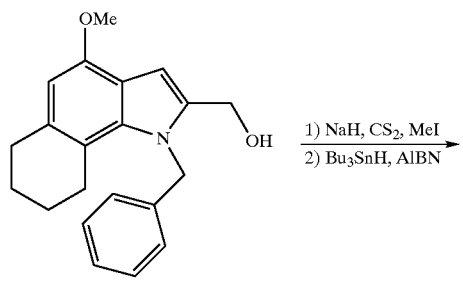

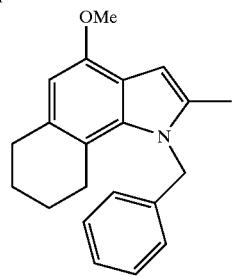

To a solution of 1-benzyl-2-hydroxymethyl-4-methoxy-6,7,8,9-tetrahydro-1H-benz[g]indole (2.0 g, 6.2 mmol) in tetrahydrofuran (30 mL) was added a hexane-washed 60% suspension of sodium hydride in mineral oil (250 mg). After 15 min, carbon disulfide (1.9 mL, 31 mmol) was added and the resulting mixture stirred a further 15 min. Methyl iodide (0.46 mL, 7.5 mmol) was added and the resulting mixture stirred for 30 min, at which time an additional portion of washed sodium hydride suspension (250 mg) was added. After stirring for 18 h the mixture was filtered through a pad of silica gel and the filtrate concentrated in vacuo. The residue was dissolved in toluene (110 mL) and treated with tri-n-butyltin hydride (3.3 mL, 13 mmol). The mixture was warmed to 90° C. then treated with approximately 30 mg 2,2'-azobisisobutyronitrile. After stirring for 3 h additional portions of tri-n-butyltin hydride (3.3 mL) and 2,2'-azobisisobutyronitrile were added and the resulting mixture stirred for 2 h then concentrated in vacuo. Chromatography (silica gel, methylene chloride/hexanes) provided 1.50 g (79%) of the title compound as a solid: mp 135–138° C. ¹H NMR (CDCl₃) δ 7.20–7.35 (m, 3H), 6.88 (d, J=8.0 Hz, 2H), 6.42 (s, 1H), 6.27 (s, 1H), 5.56 (s, 2H), 3.94 (s, 3H), 2.96 (m, 2H), 2.87 (m, 2H), 2.29 (s, 3H), 1.73 (m, 4H); MS ES+ m/e 306 (p+1); IR (CHCl₃, cm⁻¹) 2936, 1241.

Anal. Calcd for $C_{23}H_{23}NO$: C, 82.58; H, 7.59; N, 4.59. Found: C, 82.59; H, 7.61; N, 4.58.

C. Preparation of 2-[(1-benzyl-2-methyl-6,7,8,9-tetrahydro-1-H-benz[g]indol-4-yl)oxy]acetic acid methyl ester.

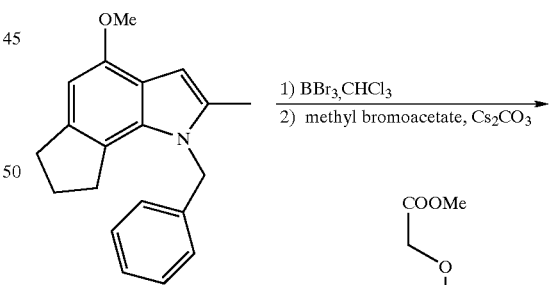

A solution of 1-benzyl-2-methyl-4-methoxy-6,7,8,9-tetrahydro-1H-benz[g]indole (2.95 g, 9.18 mmol) in methylene chloride (30 mL) was cooled to 0° C. and treated with boron tribromide (1.7 mL, 18 mmol). The mixture was stirred for 30 min, then diluted with excess methanol. Excess sodium bicarbonate and water were added, and the resulting mixture extracted with methylene chloride. The methylene chloride layer was filtered through a pad of basic alumina and concentrated in vacuo. The residue was dissolved in N,N-dimethylformamide (40 mL) and treated with cesium carbonate (2.48 g, 7.62 mmol) and methyl bromoacetate (0.72 mL, 7.6 mmol) at room temperature for 24 h. The mixture was concentrated via vacuum transfer and the residue dissolved in 2:1 ethyl acetate/hexanes. This solution was washed once with 10% citric acid, once with water, once with saturated sodium bicarbonate solution, dried (magnesium sulfate), filtered, and concentrated in vacuo. Chromatography (silica gel, methylene chloride/hexanes) of the residue provided 1.67 g (60%) of the title compound as a white solid: mp 144–146° C. $^1$H NMR (CDCl$_3$) δ 7.15–7.30 (m, 3H), 6.84 (d, J=6.6 Hz, 2H), 6.46 (s, 1H), 6.14 (s, 1H), 5.53 (s, 2H), 4.74 (s, 2H), 3.82 (s, 3H), 2.93 (m, 2H), 2.80 (m, 2H), 1.69 (m, 4H), 1.54 (s, 3H); MS ES+ m/e 364 (p+1); IR (KBr, cm$^{-1}$) 2929, 1760, 1209.

D. Preparation of 2-[[3-(2-amino-1,2-dioxoethyl)-1-benzyl-2-methyl-6,7,8,9-tetrahydro-1H-benz[g]indol-4-yl]oxy]acetic acid methyl ester.

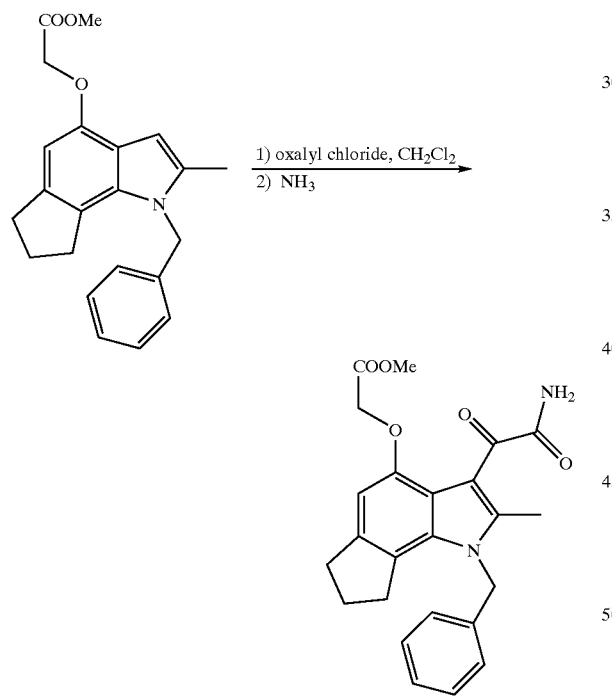

To a solution of 2-[(1-benzyl-2-methyl-6,7,8,9-tetrahydro-1H-benz[g]indol-4-yl)oxy]acetic acid methyl ester (1.55 g, 4.26 mmol) in methylene chloride (5 mL) cooled in an ice/methanol bath was added oxalyl chloride (2.0 mL, 23 mmol). The mixture was stirred for 5 min, concentrated in vacuo, diluted with fresh methylene chloride, and concentrated in vacuo. The residue was dissolved in methylene chloride (20 mL), cooled in an ice/methanol bath, and treated with excess 0.5 M ammonia in dioxane. After 15 min the mixture was concentrated in vacuo. Chromatography (silica gel, methylene chloride/acetone) of the residue provided 1.31 g (71%) of the title compound: 212–214° C. $^1$H NMR (CDCl$_3$) δ 7.20–7.35 (m, 3H), 6.93 (d, j=7.0 Hz, 2H), 6.60 (bs, 1H), 6.26 (s, 1H), 5.58 (s, 2H), 5.45 (bs, 1H), 4.69 (s, 2H), 3.78 (s, 3H), 2.91 (m, 2H), 2.80 (m, 2H), 2.42 (s, 3H), 1.67 (m, 4H); MS ES+ m/e 435 (p+1); IR (CHCl$_3$, cm$^{-1}$) 3383, 3185, 2903, 1759, 1651.

Anal. Calcd for C$_{25}$H$_{26}$N$_2$O$_5$: C, 69.11; H, 6.03; N, 6.45. Found: C, 68.41; H, 5.78; N, 6.38.

Example 15

2-[[3-(2-Amino-1,2-dioxoethyl)-1-benzyl-2-methyl-6,7,8,9-tetrahydro-1H-benz[g]indol-4-yl]oxy]acetic acid

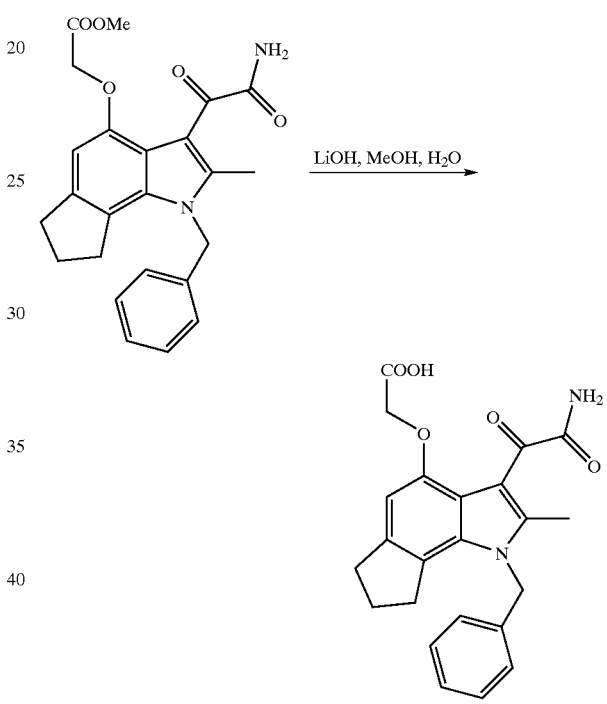

Preparation of 2-[[3-(2-amino-1,2-dioxoethyl)-1-benzyl-2-methyl-6,7,8,9-tetrahydro-1H-benz[g]indol-4-yl]oxy]acetic acid. A solution of 2-[[3-(2-amino-1,2-dioxoethyl)-1-benzyl-2-methyl-6,7,8,9-tetrahydro-1H-benz[g]indol-4-yl]oxy]acetic acid methyl ester (285 mg, 0.671 mmol) in methanol (5 ml) was treated with 1 M lithium hydroxide solution (2.5 mL) at room temperature for 1.5 h. The reaction mixture was diluted with water, concentrated in vacuo, and treated with 1 M hydrochloric acid (1 mL). The resulting precipitate was collected via vacuum filtration and dried to provide 270 mg (96%) of the title compound as a tan powder: mp>300° C. $^1$H NMR (DMSO-d$_6$) δ 8.00 (bs, 1H), 7.35 (m, 3H), 7.26 (t, J=7.0 Hz, 1H), 6.88 (d, J=7.3 Hz, 2H), 6.21 (s, 1H), 5.64 (s, 2H), 4.38 (s, 2H), 2.88 (m, 2H), 2.71 (m, 2H), 2.35 (s, 3H), 1.60 (m, 4H); MS ES+ m/e 421 (p+1); IR (KBr, cm$^{-1}$) 1636, 1402.

Anal. Calcd for C$_{24}$H$_{24}$N$_2$O$_5$: C, 68.59; H, 5.75; N, 6.66. Found: C, 67.20; H, 5.41; N, 6.43.

Example 16

2-[[3-(2-Amino-1,2-dioxoethyl)-2-methyl-1-(2-bromobenzyl)-1,6,7,8-tetrahydrocyclopent[g]indol-4-yl]oxy]acetic acid methyl ester

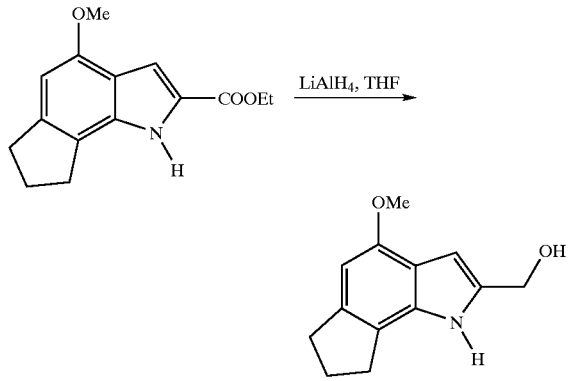

A. Preparation of 2-hydroxymethyl-4-methoxy-1,6,7,8-tetrahydrocyclopent[g]indole. To a slurry of 2-carboethoxy-4-methoxy-1,6,7,8-tetrahydrocyclopent[g]indole (5.00 g, 19.3 mmol) in tetrahydrofuran (100 mL) was added lithium aluminum hydride (733 mg, 19.3 mmol) in portions over 10 min. The mixture was stirred for 16 h at room temperature then heated at reflux for 6 h, cooled to room temperature, and stirred for 18 h. The mixture was treated with 5 N aqueous sodium hydroxide solution (5 mL), stirred for 10 min, then filtered. The filtrate was concentrated in vacuo to provide 4.2 g (100%) of the title compound as a white solid: mp 200–207° C. $^1$H NMR (CDCl$_3$) δ 8.12 (bs, 1H), 6.48 (s, 1H), 6.46 (s, 1H), 4.79 (d, J=5.5 Hz, 2H), 3.90 (s, 3H), 2.99 (t, J=7.0 Hz, 2H), 2.94 (t, J=7.3 Hz, 2H), 2.19 (quintet, J=7.7 Hz, 2H), 1.65 (t, J=5.5 Hz, 1H); MS ES+ m/e 218 (p+1); IR (CHCl$_3$, cm$^{-1}$) 3467, 1509.

Anal. Calcd for C$_{13}$H$_{15}$NO$_2$.0.1H$_2$O: C, 71.27; H, 6.99; N, 6.39. Found: C, 71.45; H, 6.94; N, 6.51.

B. Preparation of 2-methyl-4-methoxy-1,6,7,8-tetrahydrocyclopent[g]indole.

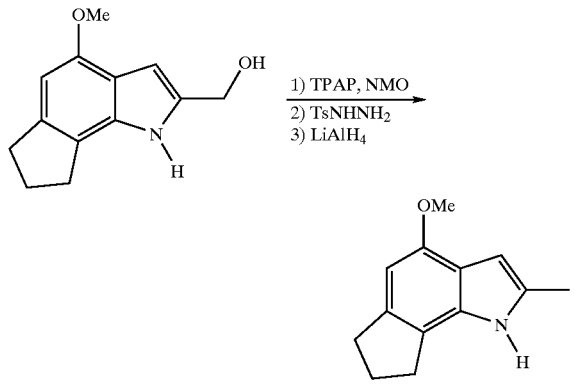

A slurry of 2-hydroxymethyl-4-methoxy-1,6,7,8-tetrahydrocyclopent[g]indole (4.2 g, 19 mmol) in methylene chloride (100 mL) was treated with 3 Å powdered molecular sieves (5 g) and 4-methylmorpholine N-oxide (3.39 g, 29.0 mmol). After stirring vigorously for 5 min, tetrapropylammonium perruthenate (200 mg, 0.58 mmol) was added and the resulting mixture stirred for 3 h. Additional portions of 4-methylmorpholine N-oxide (0.7 g) and tetrapropylammonium perruthenate (50 mg) were added and stirring continued for 1 h. The mixture was filtered through silica gel and the filtrate concentrated in vacuo. The residue was suspended in tetrahydrofuran (15 mL) and treated with tosylhydrazine (433 mg, 2.33 mmol). The mixture was stirred for 20 min at which time a precipitate formed. The suspension was refluxed for 3 min then cooled to room temperature. Lithium aluminum hydride (444 mg, 11.7 mmol) was added carefully in portions and the resulting suspension warmed to reflux then cooled to room temperature. The mixture was treated with 5 N aqueous sodium hydroxide solution (2.4 mL), diluted with ether, and filtered through a pad of silica gel. The filtrate was concentrated in vacuo to provide 386 mg (82%) of the title compound. $^1$H NMR (CDCl$_3$) δ 7.82 (bs, 1H), 6.47 (s, 1H), 6.29 (s, 1H), 3.92 (s, 3H), 3.01 (t, J=7.7 Hz, 2H), 2.94 (t, J=7.3 Hz, 2H), 2.41 (s, 3H), 2.20 (quintet, J=7.3 Hz, 2H); MS ES+ m/e 202 (p+1).

C. Preparation of 1-(2-bromobenzyl)-2-methyl-4-methoxy-1,6,7,8-tetrahydrocyclopent[g]indole.

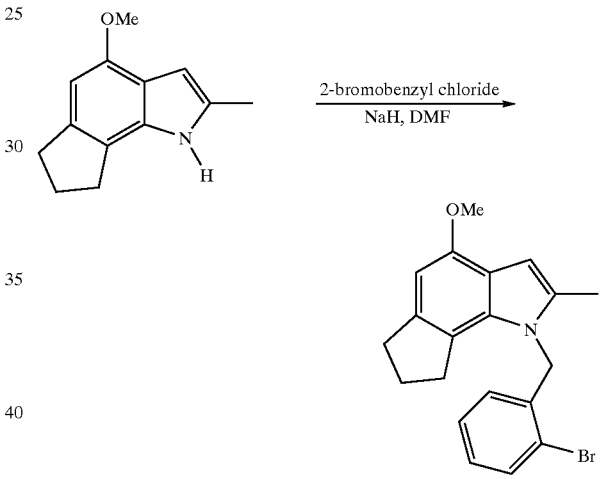

A solution of 2-methyl-4-methoxy-1,6,7,8-tetrahydrocyclopent[g]indole (2.3 g, 12 mmol) in N,N-dimthylformamide (100 mL) was treated with a 60% dispersion of sodium hydride in mineral oil (0.93 g) followed by 2-bromobenzyl chloride (4.77 g, 23.2 mmol) for 1.5 h at room temperature. The mixture was concentrated via vacuum transfer and the residue partitioned between ethyl acetate and water. The aqueous layer was separated and extracted with a fresh portion of ethyl acetate. The combined ethyl acetate layers were washed once with water and filtered through 30 mL of silica gel. The filtrate was concentrated in vacuo. Chromatography (silica gel, methylene chloride/hexanes) of the residue provided 1.24 g (29%) of the title compound as a yellow solid: mp 153–155° C. $^1$H NMR (CDCl$_3$) δ 7.56 (m, 1H), 7.06 (m, 2H), 6.44 (s, 1H), 6.40 (bs, 1H), 6.19 (m, 1H), 5.36 (bs, 2H), 3.92 (s, 3H), 2.89 (m, 4H), 2.26 (s, 3H), 2.01 (quintet, J=7.3 Hz, 2H); IR (CHCl$_3$, cm$^{-1}$) 2930, 1247.

TOS MS ES$^+$ exact mass calculated for C$_{20}$H$_{21}$BrNO (p+1): m/z=370.0807. Found: 370.0816.

Anal. Calcd for C$_{20}$H$_{20}$BrNO.0.5H$_2$O: C, 63.33; H, 5.58; N, 3.69. Found: C, 63.51; H, 5.24; N, 3.69.

D. Preparation of 2-[(2-methyl-1-(2-bromobenzyl)-1,6,7,8-tetrahydrocyclopent[g]indol-4-yl)oxy]acetic acid methyl ester

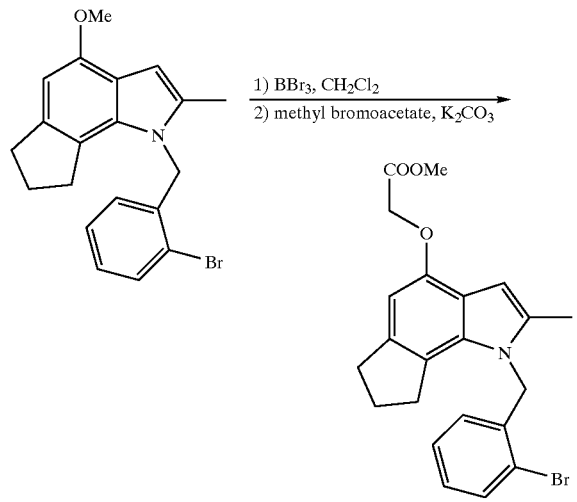

A solution of 1-(2-bromobenzyl)-2-methyl-4-methoxy-1,6,7,8-tetrahydrocyclopent[g]indole (1.28 g, 3.40 mmol) in methylene chloride (20 mL) was cooled in an ice/methanol bath and treated with boron tribromide (0.65 mL, 6.9 mmol). The mixture was warmed to −10° C. over 1.5 h then diluted with methanol (2 mL) and excess saturated aqueous sodium bicarbonate solution. The aqueous layer was separated and extracted with a fresh portion of methylene chloride. The combined methylene chloride layers were washed once with water, dried (magnesium sulfate), filtered, and concentrated in vacuo. The residue was dissolved in methylene chloride and filtered through a pad of silica gel. The filtrate was concentrated in vacuo and the residue dissolved in N,N-dimethylformamide (5 mL) and treated with cesium carbonate (1.00 g, 3.06 mmol) and methyl bromoacetate (0.29 mL, 3.1 mmol) at room temperature for 20 h. The mixture was concentrated in vacuo via vacuum transfer and the residue dissolved in methylene chloride and filtered through a pad of silica gel. The filtrate was concentrated in vacuo. Chromatography (silica gel, methylene chloride/hexanes) of the residue provided 1.10 g (84%) of the title compound. $^1$H NMR (CDCl$_3$) δ 7.59 (m, 1H), 7.07 (m, 2H), 6.47 (s, 1H), 6.33 (s, 1H), 6.18 (m, 1H), 5.35 (bs, 2H), 4.74 (s, 3H), 3.80 (s, 3H), 2.86 (m, 4H), 2.26 (s, 3H), 1.99 (quintet, J=7.3 Hz, 2H); MS ES+ m/e 428, 430 (p+1).

E. Preparation of 2-[[3-(2-amino-1,2-dioxoethyl)-2-methyl-1-(2-bromobenzyl)-1,6,7,8-tetrahydrocyclopent[g]indol-4-yl]oxy]acetic acid methyl ester.

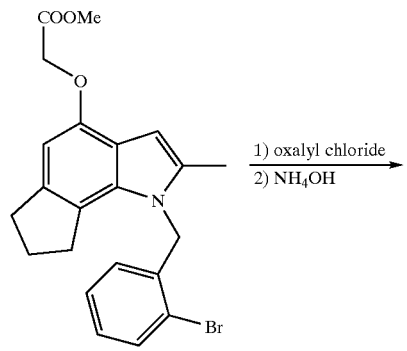

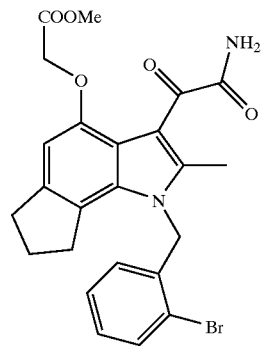

A solution of 2-[(2-methyl-1-(2-bromobenzyl)-1,6,7,8-tetrahydrocyclopent[g]indol-4-yl)oxy]acetic acid methyl ester (1.06 g, 2.47 mmol) in methylene chloride (10 mL) was cooled in an ice/methanol bath and treated with oxalyl chloride (1 mL) for 45 min. The mixture was concentrated in vacuo, dissolved in methylene chloride, and concentrated in vacuo. The residue was dissolved in a minimum of methylene chloride and treated with concentrated ammonium hydroxide (1 mL) for 30 min. The mixture was acidified with 1 N hydrochloric acid. The organic layer was dried (magnesium sulfate), filtered, and concentrated in vacuo. The residue was triturated (1:1 methylene chloride/hexanes) to provide 1.03 g (84%) of the title compound as a tan solid: mp 213–215° C. $^1$H NMR (DMSO-d$_6$) δ 7.74 (m, 1H), 7.67 (bs, 1H), 7.38 (bs, 1H), 7.26 (m, 2H), 6.51 (s, 1H), 6.17 (m, 1H), 5.48 (s, 2H), 4.72 (s, 2H), 3.71 (s, 3H), 2.80 (m, 4H), 2.42 (s, 3H), 1.93 (quintet, J=7.3 Hz, 2H); IR (KBr, cm$^{-1}$) 3375, 1759, 1724, 1646.

TOS MS ES$^+$ exact mass calculated for C$_{24}$H$_{24}$BrN$_2$O$_5$ (p+1): m/z=499.0869. Found: 499.0841.

Example 17

2-[[3-(2-Amino-1,2-dioxoethyl)-2-methyl-1-(2-bromobenzyl)-1,6,7,8-tetrahydrocyclopent[g]indol-4-yl]oxy]acetic acid

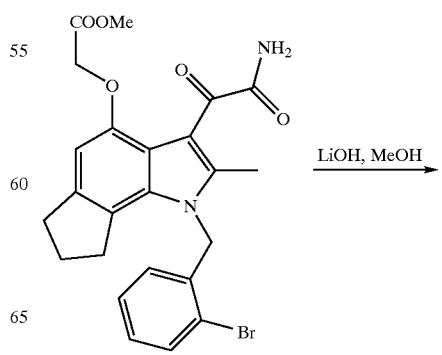

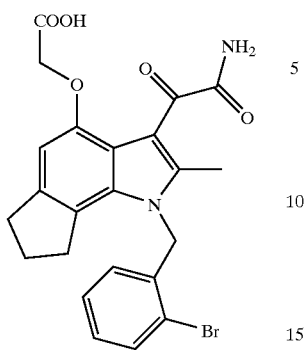

Preparation of 2-[[3-(2-amino-1,2-dioxoethyl)-2-methyl-1-(2-bromobenzyl)-1,6,7,8-tetrahydrocyclopent[g]indol-4-yl]oxy]acetic acid.

A solution of 2-[[3-(2-amino-1,2-dioxoethyl)-2-methyl-1-(2-bromobenzyl)-1,6,7,8-tetrahydrocyclopent[g]indol-4-yl]oxy]acetic acid methyl ester (106 mg, 0.21 mmol) in methanol (3 mL) was treated with 1 N lithium hydroxide solution (1 mL). The solution was heated to reflux then allowed to cool to room temperature. The mixture was diluted with water and acidified with 1 N hydrochloric acid. The resulting precipitate was collected via vacuum filtration and washed carefully with ethyl acetate to provide 36 mg (35%) of the title compound as a tan solid: mp 261–262° C. (dec). $^1$H NMR (DMSO-$d_6$) δ 12.88 (bs, 1H), 7.72 (m, 2H), 7.43 (bs, 1H), 7.26 (m, 2H), 6.46 (s, 1H), 6.18 (m, 1H), 5.48 (s, 2H), 4.62 (s, 2H), 2.80 (m, 4H), 2.43 (s, 3H), 1.93 (quintet, J=7.3 Hz, 2H); IR (KBr, cm$^{-1}$) 3431, 1735, 1628, 1213.

TOS MS ES$^+$ exact mass calculated for $C_{23}H_{22}BrN_2O_5$ (p+1): m/z=485.0712. Found: 485.0713.

Example 18

2-[[3-(2-Amino-1,2-dioxoethyl)-2-methyl-1-(2-phenylbenzyl)-1,6,7,8-tetrahydrocyclopent[g]indol-4-yl]oxy]acetic acid methyl ester

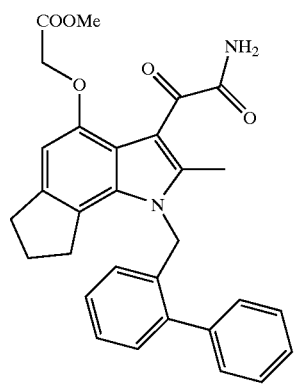

Preparation of 2-[[3-(2-amino-1,2-dioxoethyl)-2-methyl-1-(2-phenylbenzyl)-1,6,7,8-tetrahydrocyclopent[g]indol-4-yl]oxy]acetic acid methyl ester. A mixture of 2-[[3-(2-amino-1,2-dioxoethyl)-2-methyl-1-(2-bromobenzyl)-1,6,7,8-tetrahydrocyclopent[g]indol-4-yl]oxy]acetic acid methyl ester (200 mg, 0.400 mmol), phenylboronic acid (49 mg, 0.40 mmol), cesium carbonate (260 mg, 0.800 mmol), and tetrakis(triphenylphosphine)palladium(0) (14 mg, 0.0012 mmol) in dioxane (20 mL) was sparged with nitrogen for 5 min then heated at 100° C. for 6 h. The mixture was allowed to cool to room temperature and filtered through a pad of silica gel that was subsequently washed with acetone. The filtrate was concentrated in vacuo. Reverse-phase chromatography (C18, water/acetonitrile) of the residue provided 61 mg (31%) of the title compound. $^1$H NMR (CDCl$_3$) δ 7.49 (t, J=7.0 Hz, 2H), 7.42 (t, J=7.3 Hz, 1H), 7.37 (d, J=7.0 Hz, 2H), 7.29 (m, 2H), 7.17 (m, 1H), 6.56 (bs, 1H), 6.48 (d, J=8.0 Hz, 1H), 6.44 (s, 1H), 5.42 (bs, 1H), 5.26 (s, 2H), 4.68 (s, 2H), 3.76 (s, 3H), 2.86 (t, J=7.3 Hz, 4H), 2.34 (s, 3H), 2.01 (quintet, J=7.0 Hz, 2H); MS FD+ m/e 496 (p); IR (KBr, cm$^{-1}$) 3461, 1757, 1699, 1642.

Example 19

2-[[3-(2-Amino-1,2-dioxoethyl)-2-methyl-1-(2-phenylbenzyl)-1,6,7,8-tetrahydrocyclopent[g]indol-4-yl]oxy]acetic acid

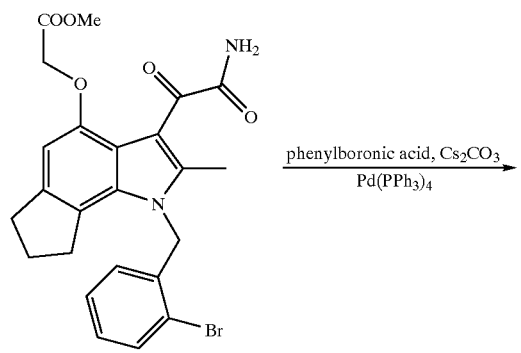

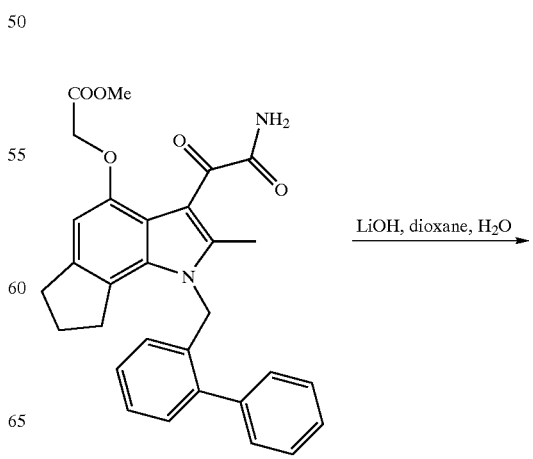

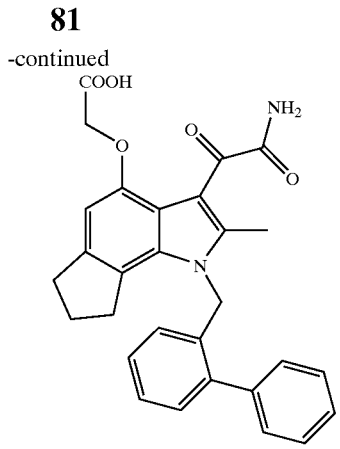

Preparation of 2-[[3-(2-amino-1,2-dioxoethyl)-2-methyl-1-(2-phenylbenzyl)-1,6,7,8-tetrahydrocyclopent[g]indol-4-yl]oxy]acetic acid. A slurry of 2-[[3-(2-amino-1,2-dioxoethyl)-2-methyl-1-(2-phenylbenzyl)-1,6,7,8-tetrahydrocyclopent[g]indol-4-yl]oxy]acetic acid methyl ester (18 mg, 0.036 mmol) in dioxane (3 mL) was warmed until a clear solution was produced. The mixture was treated with 1 N lithium hydroxide solution (0.5 mL) and warmed briefly. After 2 h the solution was adjusted to pH 3 and the resulting precipitate collected via vacuum filtration to provide 6 mg (34%) of the title compound. MS ES+ m/e 483 (p+1).

Example 20

2-[[3-(2-amino-1,2-dioxoethyl)-1-[2-(5-bromothiophen-2-yl)benzyl]-2-methyl-1,6,7,8-tetrahydrocyclopent[g]indol-4-yl]oxy]acetic acid methyl ester

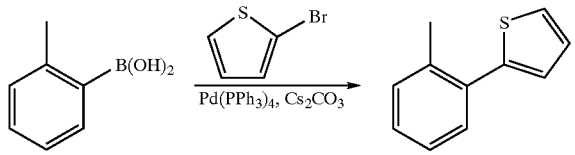

A. Preparation of 2-o-tolylthiophene. A mixture of 2-methylphenylboronic acid (1.4 g, 10 mmol), 2-bromothiophene (0.47 mL, 10 mmol), tetrakis(triphenylphosphine)palladium(0) (350 mg, 0.30 mmol), cesium carbonate (6.6 g, 20 mmol), and water (3 drops) in dioxane (75 mL) was heated at 95–100° C. for 2 h. The mixture was cooled to room temperature, diluted with hexane, and washed twice with water. The resulting organic solution was filtered through a pad of silica gel and concentrated in vacuo to provide 1.61 g (93%) of the title compound as a yellow oil. $^1$H NMR (CDCl$_3$) δ 7.41 (dd, J=7, 2 Hz, 1H), 7.34 (dd, J=2, 7 Hz, 1H), 7.25 (m, 3H), 7.09 (m, 2H), 2.43 (s, 3H).

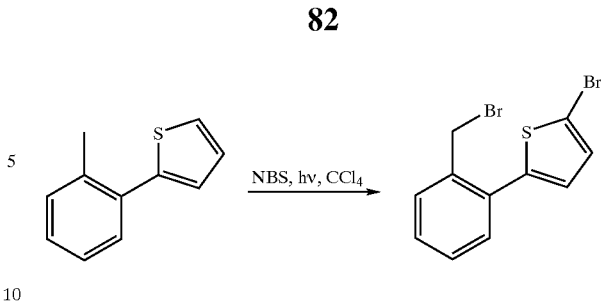

B. Preparation of 2-bromo-5-(2-bromomethylphenyl)thiophene. A mixture of 2-o-tolylthiophene (1.4 g, 8.0 mmol) and N-bromosuccinimide (7.0 g, 40 mmol) in carbon tetrachloride (20 mL) was stirred and irradiated with a heat lamp for 2 h. To this mixture was added 2,2'-azobisisobutyronitrile (~10 mg) and irradiation continued for 6 h. The resulting mixture was filtered through a pad of silica gel and concentrated in vacuo to provide 975 mg (36%) of the title compound as a light yellow oil. $^1$H NMR (CDCl$_3$) δ 7.49 (d, J=8 Hz, 1H), 7.34 (m, 3H), 7.06 (s, 2H), 4.56 (s, 2H).

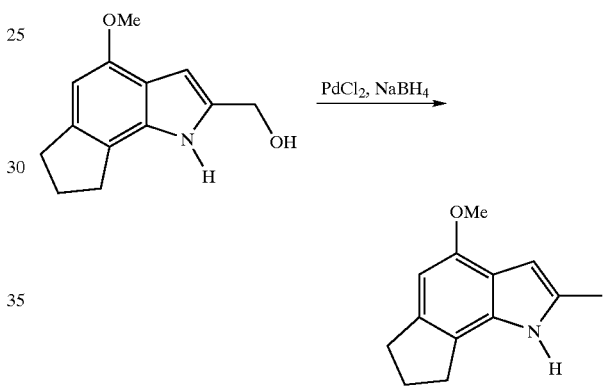

C. Preparation of 2-methyl-4-methoxy-1,6,7,8-tetrahydrocyclopent[g]indole. A solution of 2-hydroxymethyl-4-methoxy-1,6,7,8-tetrahydrocyclopent[g]indole (1.0 g, 4.6 mmol) and methanol (10 mL) in tetrahydrofuran (100 mL) was treated with palladium(II) chloride (1.4 g, 8.0 mmol) and sodium borohydride (520 mg, 14 mmol) at room temperature for 40 min. The mixture was filtered and concentrated in vacuo. The purple residue was dissolved in methylene chloride and passed through a pad of silica gel. Concentration of the filtrate provided 620 mg (67%) of the title compound as a crystalline solid. $^1$H NMR (CDCl$_3$) δ 7.65 (bs, 1H), 6.44 (s, 1H), 6.27 (s, 1H), 3.90 (s, 3H), 2.98 (t, J=7 Hz, 2H), 2.92 (t, J=7 Hz, 2H), 2.41 (s, 3H), 2.18 (quintet, J=7 Hz, 2H); MS ES+ m/e 202 (p+1); IR (CHCl$_3$, cm$^{-1}$) 3473, 2953, 1508.

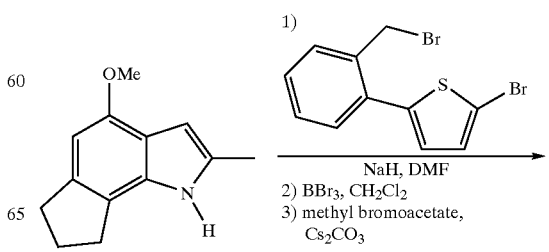

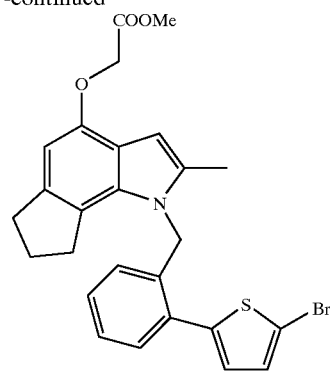

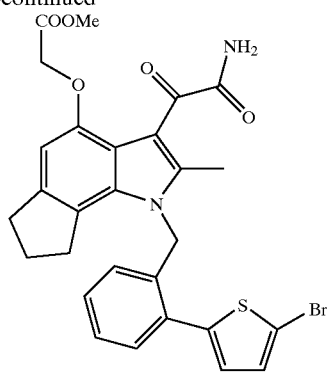

D. Preparation of 2-[(1-[2-(5-bromothiophen-2-yl)benzyl]-2-methyl-1,6,7,8-tetrahydrocyclopent[g]indol-4-yl)oxy]acetic acid methyl ester. To a solution of 2-methyl-4-methoxy-1,6,7,8-tetrahydrocyclopent[g]indole (517 mg, 2.57 mmol) in N,N-dimethylformamide (10 mL) was added a dispersion of 60% sodium hydride in mineral oil (120 mg). After gas evolution had ceased, a solution of 2-bromo-5-(2-bromomethylphenyl)thiophene (975 mg, 3.85 mmol) in N,N-dimethylformamide (5 mL) was added over 2–3 min. The resulting mixture was stirred for 108 h, diluted with water, and extracted with a 1:1 mixture of ether/hexane. The organic phase was washed twice with water, concentrated in vacuo, dissolved in methylene chloride, and passed through a pad of silica gel. The filtrate was concentrated in vacuo and the residue dissolved in methylene chloride (10 mL), cooled to 0° C., and treated with boron tribromide (0.11 mL, 2.0 mmol). The mixture was allowed to warm to room temperature and stir for 2 h. Methanol (2 mL) was added followed by saturated sodium bicarbonate solution (~30 mL). The resulting mixture was extracted twice with methylene chloride. The combined organic layers were dried (magnesium sulfate), filtered, and concentrated in vacuo. The residue was immediately dissolved in N,N-dimethylformamide (5 mL) and treated with cesium carbonate (490 mg, 1.5 mmol) and methyl bromoacetate (0.14 mL, 1.5 mmol) at room temperature for 18 h. The mixture was diluted with water, stirred for 30 min, and the resulting solid collected via vacuum filtration. Chromatography (silica gel, hexane/methylene chloride) provided 187 mg (14%) of the title compound as a beige solid. $^1$H NMR (CDCl$_3$) δ 7.36 (d, J=7 Hz, 1H), 7.23 (t, J=8 Hz, 1H), 7.13 (t, J=8 Hz, 1H), 7.10 (d, J=4 Hz, 1H), 6.86 (d, J=4 Hz, 1H), 6.45 (s, 1H), 6.33 (s, 1H), 6.32 (d, J=7 Hz, 1H), 5.41 (s, 2H), 4.75 (s, 2H), 3.81 (s, 3H), 2.85 (m, 4H), 2.22 (s, 3H), 2.01 (quintet, J=7 Hz, 2H); MS ES+ m/e 509, 511 (p+1).

E. Preparation of 2-[[3-(2-amino-1,2-dioxoethyl)-1-[2-(5-bromothiophen-2-yl)benzyl]-2-methyl-1,6,7,8-tetrahydrocyclopent[g]indol-4-yl]oxy]acetic acid methyl ester. A solution of 2-[(1-[2-(5-bromothiophen-2-yl)benzyl]-2-methyl-1,6,7,8-tetrahydrocyclopent[g]indol-4-yl)oxy]acetic acid methyl ester (180 mg, 0.35 mol) in methylene chloride (5 mL) was treated with oxalyl chloride (~1 mL) at room temperature for 90 min. The resulting mixture was concentrated in vacuo and the residue dissolved in methylene chloride (5 mL). This solution was treated with 34% ammonia hydroxide solution (~1 mL). The resulting mixture was placed on top of a silica gel column and chromatographed (methylene chloride/acetone) to provide 65 mg (32%) of the title compound as a brown powder. $^1$H NMR (DMSO-d$_6$) δ 7.63 (bs, 1H), 7.45 (d, J=8 Hz, 1H), 7.32 (m, 3H), 7.25 (m, 2H), 6.44 (s, 1H), 6.23 (d, J=8 Hz, 1H), 5.54 (s, 2H), 4.68 (s, 2H), 3.67 (s, 3H), 2.74 (t, J=7 Hz, 2H), 2.64 (m, 2H), 2.39 (s, 3H), 1.86 (quintet, J=7 Hz, 2H); TOS MS ES$^+$ exact mass calculated for C$_{28}$H$_{26}$BrN$_2$O$_5$S (p+1): m/z = 581.0746. Found: 581.0761.

Example 21

2-[[3-(2-amino-1,2-dioxoethyl)-2-methyl-1-[2-(5-bromothiophen-2-yl)benzyl]-1,6,7,8-tetrahydrocyclopent[g]indol-4-yl]oxy]acetic acid

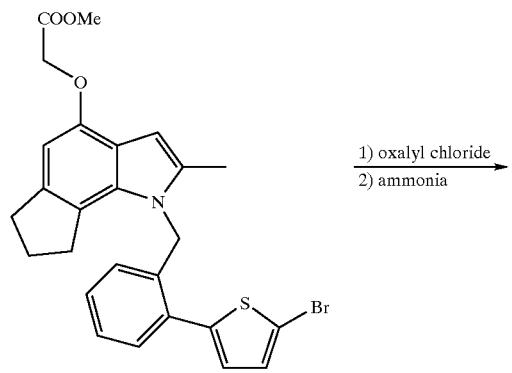

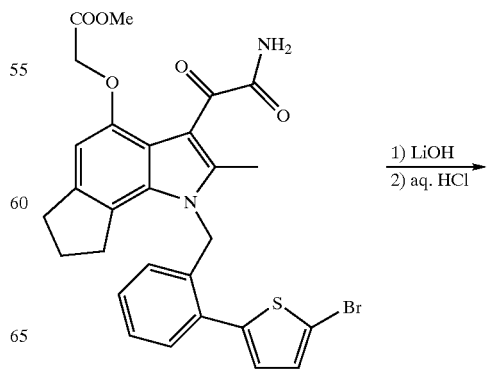

-continued

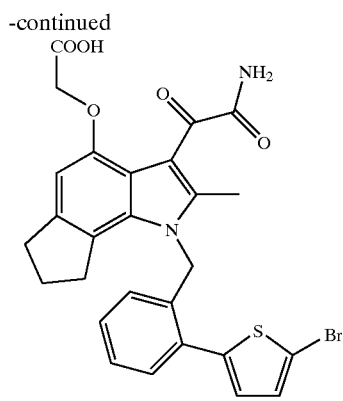

A mixture of 2-[[3-(2-amino-1,2-dioxoethyl)-2-methyl-1-[2-(5-bromothiophen-2-yl)benzyl]-1,6,7,8-tetrahydrocyclopent[g]indol-4-yl]oxy]acetic acid methyl ester (50 mg, 0.086 mmol) in dioxane (5 mL) was warmed until a clear solution was obtained. This solution was treated with 1M lithium hydroxide solution (1 mL) at room temperature for 90 min. The pH was adjusted to ~3 with hydrochloric acid. The mixture was diluted with water and stirred for 15 min. The resulting precipitate was collected via vacuum filtration to provide 25 mg (51%) of the title compound as a green solid. TOS MS ES+ exact mass calculated for $C_{27}H_{24}BrN_2O_5S$ (p+1): m/z=567.0589. Found: 567.0603.

We claim:

1. A cycloalkylfused indole compound of formula (I), or a pharmaceutically acceptable salt, solvate or prodrug thereof;

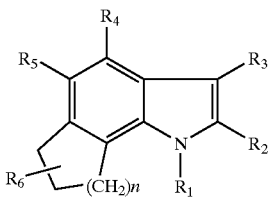

(I)

wherein;

n is 1, 2 or 3;

$R_1$ is selected from group (a), (b), or (c) wherein;
 (a) is $C_2$–$C_{20}$ alkyl, $C_2$–$C_{20}$ haloalkyl, $C_2$–$C_{20}$ alkenyl, $C_2$–$C_{20}$ alkynyl, carbocyclic radical, or heterocyclic radical, or
 (b) is a member of (a) substituted with one or more independently selected from hydrogen, ($C_1$–$C_8$) alkyl, ($C_2$–$C_8$)alkenyl, ($C_2$–$C_8$) alkynyl, ($C_7$–$C_{12}$) aralkyl, ($C_7$–$C_{12}$)alkaryl, ($C_3$–$C_8$)cycloalkyl, ($C_3$–$C_8$)cycloalkenyl, phenyl, toluyl, xylenyl, biphenyl, ($C_1$–$C_8$)alkoxy, ($C_2$–$C_8$)alkenyloxy, ($C_2$–$C_8$)alkynyloxy, ($C_2$–$C_{12}$)alkoxyalkyl, ($C_2$–$C_{12}$) alkoxyalkyloxy, ($C_2$–$C_{12}$)alkylcarbonyl, ($C_2$–$C_{12}$) alkylcarbonylamino, ($C_2$–$C_{12}$)alkoxyamino;
 (c) is the group -(L)-$R_{80}$; where, -(L)- is a divalent linking group of 1 to 12 atoms selected from carbon, hydrogen, oxygen, nitrogen, and sulfur; wherein the combination of atoms in -(L)- are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where $R_{80}$ is a group selected from (a) or (b)

$R_2$ is hydrogen, or a group containing 1 to 10 non-hydrogen atoms plus any required hydrogen atoms;

$R_3$ is -($L_3$)- Z, here -($L_3$)- is a divalent linker group selected from a bond or a divalent group selected from:

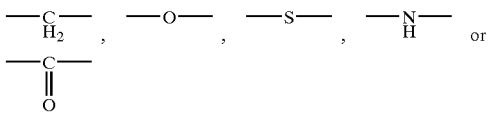

and Z is selected from an oxime amide or oxime thioamide group represented by the formulae,

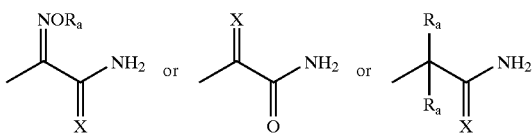

wherein X is oxygen or sulfur, $R_a$ is independently selected from hydrogen, $C_1$–$C_8$ alkyl, aryl, $C_1$–$C_8$ alkaryl, $C_1$–$C_8$ alkoxy, aralkyl and —CN;

$R_4$ is the group, hydrogen, $CONH_2$, $CONHR^{4b}$ or -(La)-(acidic group) wherein -($L_a$)-, is an acid linker having an acid linker length of 1 to 8;

or the group -($L_h$)-(N-hydroxyfunctional amide group); wherein -($L_h$)-, is an N-hydroxyfunctional amide linker having a N-hydroxyfunctional amide linker length of 1 to 8; and wherein a N-hydroxyfunctional amide group is represented by the formula:

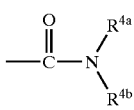

wherein $R^{4a}$ is selected from the group consisting of OH, ($C_1$–$C_6$)alkoxy, and aryloxy; and wherein $R^{4b}$ is hydrogen or an organic substituent selected from the group consisting of ($C_1$–$C_8$)alkyl, aryl, ($C_7$–$C_{14}$) aralkyl, ($C_7$–$C_{14}$)alkaryl, ($C_3$–$C_8$)cycloalkyl, ($C_1$–$C_8$) alkoxyalkyl and these groups substituted with halogen, —$CF_3$, —OH, ($C_1$–$C_8$)alkyl, amino, carbonyl, and —CN;

or $R_4$ is the group -(Lc)- (acylamino acid group)- wherein the "acylamin acid group" is represented by the formula:

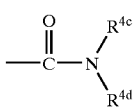

wherein $R^{4c}$ is selected from the group consisting of H, ($C_1$–$C_6$)alkyl, ($C_1$–$C_6$)alkoxy, heteroaryl and aryl, —$CF_3$; and wherein $NR^{4d}$ is an amino acid residue of either a natural or unnatural amino acid with the nitrogen atom being part of the amino group of the amino acid, $R_5$ is selected from hydrogen, $(C_1-C_8)$alkyl, $(C_2-C_8)$ alkenyl, $(C_2-C_8)$ alkynyl, $(C_7-C_{12})$aralkyl, $(C_7-C_{12})$ alkaryl, $(C_3-C_8)$cycloalkyl, $(C_3-C_8)$cycloalkenyl, phenyl, toluyl, xylenyl, biphenyl, $(C_1-C_8)$alkoxy, $(C_2-C_8)$alkenyloxy, $(C_2-C_8)$alkynyloxy, $(C_2-C_{12})$ alkoxyalkyl, $(C_2-C_{12})$alkoxyalkyloxy, $(C_2-C_{12})$ alkylcarbonyl, $C_2-C_{12})$alkylcarbonylamino, $(C_2-C_{12})$ alkoxyamino; and $R_6$ is a multiple or single independently selected from hydrogen, $(C_1-C_8)$alkyl, $(C_2-C_8)$alkenyl, $(C_2-C_8)$ alkynyl, $(C_7-C_{12})$aralkyl, $(C_7-C_{12})$alkaryl, $(C_3-C_8)$ cycloalkyl, $(C_3-C_8)$cycloalkenyl, phenyl, toluyl, xylenyl, biphenyl, $(C_1-C_8)$alkoxy, $(C_2-C_8)$alkenyloxy, $(C_2-C_8)$alkynyloxy, $C_2-C_{12})$alkoxyalkyl, $(C_2-C_{12})$ alkoxyalkyloxy, $C_2-C_{12})$alkylcarbonyl, $(C_2-C_{12})$ alkylcarbonylamino, $(C_2-C_{12})$alkoxyamino.

2. The compound of claim 1 wherein $R_2$, is hydrogen, $(C_1-C_4)$alkyl, $(C_2-C_4)$alkenyl, —O—$(C_1-C_3$ alkyl), —S—$(C_1-C_3$ alkyl), $(C_3-C_4)$cycloalkyl, —CF$_3$, halo, —NO$_2$, —CN, or —SO$_3$.

3. The compound of claim 1 wherein the n is 1.

4. The compound of claim 1 wherein n is 2.

5. The compound of claim 1 wherein the N-hydroxyfunctional amide linker group, -($L_h$)-, or the acid linker -($L_a$)-, or the acylamino acid linker -($L_c$)-, for $R_4$ is selected from a gr up represented by the formula;

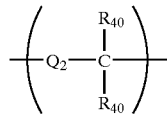

where $Q_2$ is selected from the group —(CH$_2$)—, —O—, —NH—, —C(O)—, and —S—, and each $R_{40}$ is independently selected from hydrogen, $(C_1-C_8)$alkyl, aryl, $(C_1-C_8)$ alkaryl, $(C_1-C_8)$ alkoxy, aralkyl, and halo.

6. The compound of claim 1 wherein the N-hydroxyfunctional amide linker group, -($L_h$)-, or the acid linker -($L_a$)-, or the acylamino acid linker -($L_c$)-, for $R_4$ is a divalent group independently selected from,

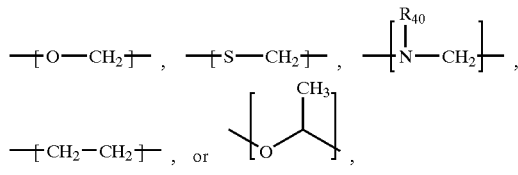

where $R_{40}$, $R_{41}$, $R_{42}$, and $R_{43}$ are independently selected from hydrogen, $C_1-C_8$ alkyl.

7. The compound of claim 1 wherein for $R_3$, Z is the group represented by the formula;

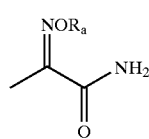

and the linking group -($L_3$)- is a bond; and $R_a$ is hydrogen, methyl, ethyl, propyl, isopropyl, phenyl or benzyl.

8. The compound of claim 1 wherein for $R_3$, Z is the group represented by the formula;

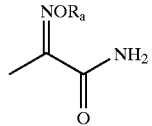

and the linking group -($L_3$)- is a bond; and $R_a$ is hydrogen.

9. The compound of claim 1 wherein for $R_3$, Z is the group represented by the formula:

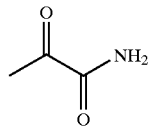

and the linking group -($L_3$)- is a bond.

10. The compound of claim 1 wherein for $R_3$, Z is the group represented by the formula:

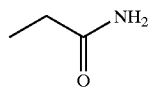

and the linking group -($L_3$)- is a bond.

11. The compound of claim 1 wherein for $R_3$ the divalent linking group -($L_3$)- is a bond.

12. The compound of claim 1 wherein $R_4$ is the group, -($L_c$)-(N-hydroxyfunctional amide group) and wherein the (N-hydroxyfunctional amide group) is:

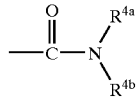

and $R^{4a}$ is independently selected from the group consisting of hydrogen, —OH, $(C_1-C_6)$alkoxy, and aryloxy; and wherein $R^{4b}$ is independently selected from the group consisting of H, $(C_1-C_6)$alkyl, arylalkyl, heteroaryl and aryl.

13. The compound of claim 1 wherein $R_4$ is the group, -($L_c$)-(acylamino acid group) and wherein the (acylamino acid group) is:

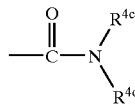

and $R^{4c}$ is selected from the group consisting of H, $(C_1-C_6)$ alkyl, $(C_1-C_6)$alkoxy, heteroaryl and aryl; and wherein $NR^{4d}$ is an amino acid residue of an amino acid with the nitrogen atom being part of the amino group of the amino acid.

14. The compound of claim 1 wherein $R_4$ is the group, -($L_a$)-(acidic group) and wherein the (acidic group) is selected from the group consisting of —COOH, —COONa, and -COOK.

15. A compound of according to formula I selected from the group consisting of:

2-[[3-(2-Amino-1,2-dioxoethyl)-2-ethyl-1-benzyl-1,6,7,8-tetrahydrocyclo-pent[g]indol-4-yl]oxy]acetic acid methyl ester;

2-[[3-(2-Amino-1,2-dioxoethyl)-2-ethyl-1-benzyl-1,6,7,8-tetrahydrocyclo-pent[g]indol-4-yl]oxy]acetic acid;

2-[[3-(2-Amino-1,2-dioxoethyl)-2-methyl-1-benzyl-1,6,7,8-tetrahydrocyclo-pent[g]indol-4-yl]oxy]acetic acid methyl ester;

2-[[3-(2-Amino-1,2-dioxoethyl)-2-methyl-1-benzyl-1,6,7,8-tetrahydrocyclo-pent[g]indol-4-yl]oxy]acetic acid;

2-[4-(2-Benzenesulfonylamino-2-oxoethoxy)-1-benzyl-2-methyl-1,6,7,8-tetrahydro-1-aza-as-indacen-3-yl]-2-oxoacetamide;

2-[[3-(2-Amino-1,2-dioxoethyl)-2-methyl-1-(3-fluorobenzyl)-1,6,7,8-tetrahydrocyclopent[g]indol-4-yl]oxy]acetic acid methyl ester;

2-[[3-(2-Amino-1,2-dioxoethyl)-2-methyl-1-(3-fluorobenzyl)-1,6,7,8-tetrahydrocyclopent[g]indol-4-yl]oxy]acetic acid hydrate;

2-[[3-(2-Amino-1,2-dioxoethyl)-2-methyl-1-(2-fluorobenzyl)-1,6,7,8-tetrahydrocyclopent[g]indol-4-yl]oxy]acetic acid;

2-[[3-(2-Amino-1,2-dioxoethyl)-2-methyl-1-(4-fluorobenzyl)-1,6,7,8-tetrahydrocyclopent[g]indol-4-yl]oxy]acetic acid methyl ester;

2-[[3-(2-Amino-1,2-dioxoethyl)-1-benzyl-2-ethyl-6,7,8,9-tetrahydro-1H-benz[g]indol-4-yl]oxy]acetic acid methyl ester;

2-[[3-(2-Amino-1,2-dioxoethyl)-1-benzyl-2-ethyl-6,7,8,9-tetrahydro-1H-benz[g]indol-4-yl]oxy]acetic acid;

2-[[3-(2-Amino-1,2-dioxoethyl)-1-benzyl-2-methyl-6,7,8,9-tetrahydro-1H-benz[g]indol-4-yl]oxy]acetic acid methyl ester;

2-[[3-(2-Amino-1,2-dioxoethyl)-1-benzyl-2-methyl-6,7,8,9-tetrahydro-1H-benz[g]indol-4-yl]oxy]acetic acid;

2-[[3-(2-Amino-1,2-dioxoethyl)-2-methyl-1-(2-bromobenzyl)-1,6,7,8-tetrahydrocyclopent[g]indol-4-yl]oxy]acetic acid methyl ester;

2-[[3-(2-Amino-1,2-dioxoethyl)-2-methyl-1-(2-bromobenzyl)-1,6,7,8-tetrahydrocyclopent[g]indol-4-yl]oxy]acetic acid;

2-[[3-(2-Amino-1,2-dioxoethyl)-2-methyl-1-(2-phenylbenzyl)-1,6,7,8-tetrahydrocyclopent[g]indol-4-yl]oxy]acetic acid methyl ester; and 2-[[3-(2-Amino-1,2-dioxoethyl)-2-methyl-1-(2-phenylbenzyl)-1,6,7,8-tetrahydrocyclopent[g]indol-4-yl]oxy]acetic acid, or a pharmaceutically acceptable salt, solvate or prodrug thereof.

16. A cycloalkylfused indole compound represented by the formulae (C1), (C2), (C3), (C4), (C5), (C6), (C7), (C8), (C9), (C10), (C11), or (C12);

(C1)

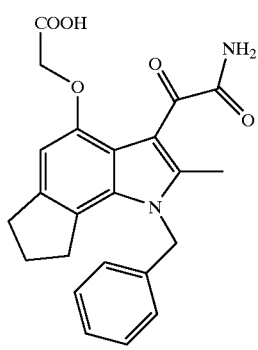

(C2)

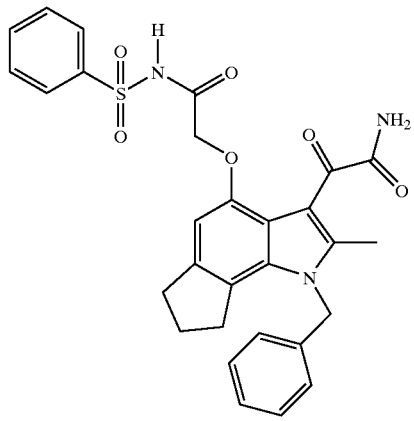

(C3)

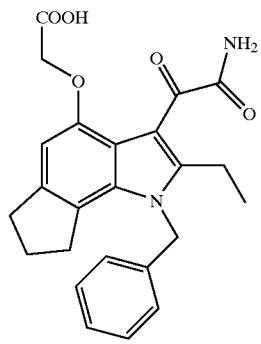

(C4)

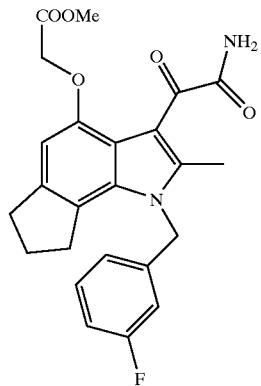

(C5)

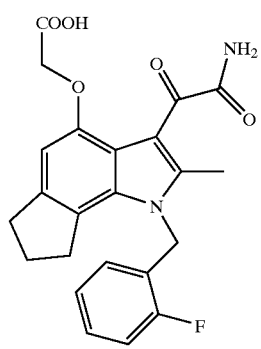

91
-continued
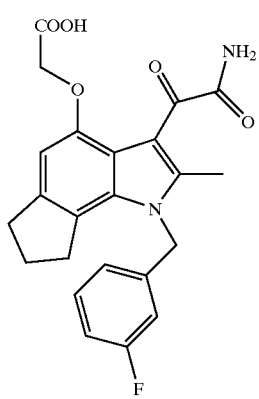
(C6)
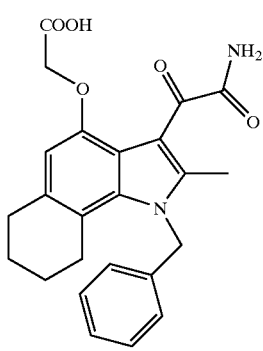
(C7)
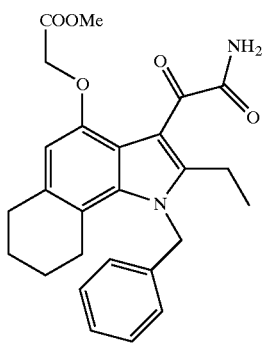
(C8)
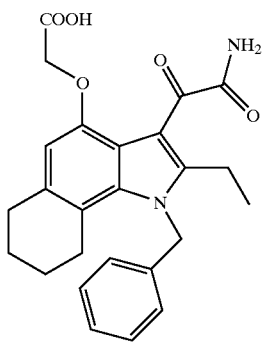
(C9)
92
-continued
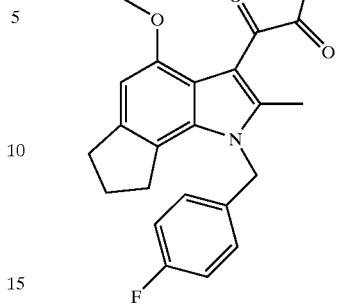
(C10)
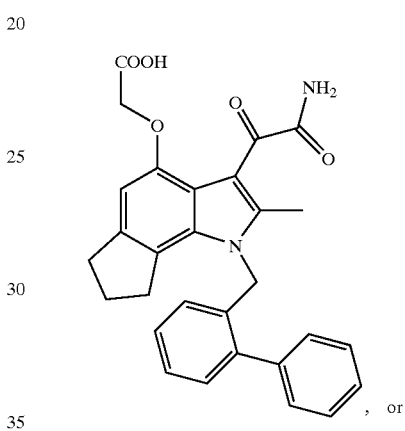
(C11)
, or
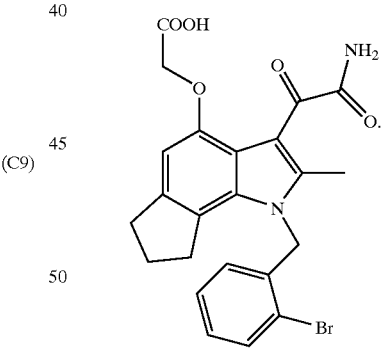
(C12)
17. A pharmaceutical formulation comprising a cycloalkylfused indole compound of claim 1 together with a pharmaceutically acceptable carrier or diluent.
* * * * *